(12) United States Patent
Godfrey et al.

(10) Patent No.: US 10,557,134 B2
(45) Date of Patent: Feb. 11, 2020

(54) PROTECTION OF BARCODES DURING DNA AMPLIFICATION USING MOLECULAR HAIRPINS

(71) Applicants: TRUSTEES OF BOSTON UNIVERSITY, Boston, MA (US); ONTARIO INSTITUTE FOR CANCER RESEARCH MARS CENTRE, Toronto (CA)

(72) Inventors: Tony Edward Godfrey, Chestnut Hill, MA (US); Anders Torbjoern Staahlberg, Kaallered (SE); Paul Krzyzanowski, Toronto (CA)

(73) Assignees: TRUSTEES OF BOSTON UNIVERSITY, Boston, MA (US); ONTARIO INSTITUTE FOR CANCER RESEARCH, Toronto, ON (CA)

( * ) Notice: Subject to any disclaimer, the term of this patent is extended or adjusted under 35 U.S.C. 154(b) by 228 days.

(21) Appl. No.: 15/552,618

(22) PCT Filed: Feb. 24, 2016

(86) PCT No.: PCT/US2016/019264
§ 371 (c)(1),
(2) Date: Aug. 22, 2017

(87) PCT Pub. No.: WO2016/138080
PCT Pub. Date: Sep. 1, 2016

(65) Prior Publication Data
US 2018/0051277 A1 Feb. 22, 2018

Related U.S. Application Data
(60) Provisional application No. 62/120,183, filed on Feb. 24, 2015.

(51) Int. Cl.
C12P 19/34 (2006.01)
C12N 15/10 (2006.01)
(Continued)

(52) U.S. Cl.
CPC ....... *C12N 15/1065* (2013.01); *C12Q 1/6806* (2013.01); *C12Q 1/6855* (2013.01); *C12Q 1/6874* (2013.01)

(58) Field of Classification Search
None
See application file for complete search history.

(56) References Cited

U.S. PATENT DOCUMENTS 5,935,793 A   8/1999   Wong
5,981,176 A   11/1999  Wallace
(Continued)

FOREIGN PATENT DOCUMENTS

CN   103866009 A    6/2014
WO   2001/092579 A2  12/2001
(Continued)

OTHER PUBLICATIONS

Singh et al., Multilocus sequence typing of *Salmonella* strains by high-throughput sequencing of selectively amplified target genes, 2012, vol. 88, pp. 127-133. (Year: 2012).*
(Continued)

*Primary Examiner* — Kenneth R Horlick
(74) *Attorney, Agent, or Firm* — Nixon Peabody, LLP

(57) ABSTRACT

Described herein are approaches for the improved detection, identification, and/or quantification of target nucleic acids. These approaches provide a means of detecting, identifying, and/or quantifying rare target nucleic acid molecules, including DNA and RNA molecules, from the same sample, and in the same reaction, by using "hairpin barcode primers," as the term is defined herein, to incorporate unique
(Continued)

barcodes into target nucleic acids in a PCR pre-amplification step.

21 Claims, 20 Drawing Sheets

Specification includes a Sequence Listing.

(51) Int. Cl.
 *C12Q 1/6806* (2018.01)
 *C12Q 1/6855* (2018.01)
 *C12Q 1/6874* (2018.01)

(56) References Cited

U.S. PATENT DOCUMENTS

| | | | |
|---|---|---|---|
| 6,309,829 | B1 | 10/2001 | Livak |
| 6,451,525 | B1 | 9/2002 | Blasband |
| 7,517,977 | B2 | 4/2009 | Wangh |
| 7,833,716 | B2 * | 11/2010 | Becker .................. C12Q 1/6848 435/6.12 |
| 8,728,766 | B2 | 5/2014 | Casbon |
| 2004/0137458 | A1 | 7/2004 | Archambault et al. |
| 2014/0120529 | A1 | 5/2014 | Andersen et al. |
| 2014/0155274 | A1 | 6/2014 | Xie et al. |
| 2014/0242586 | A1 * | 8/2014 | Whitman ............. C12Q 1/6853 435/6.11 |

FOREIGN PATENT DOCUMENTS

| | | |
|---|---|---|
| WO | 2007/005649 A2 | 1/2007 |
| WO | 2009/030100 A1 | 3/2009 |
| WO | WO2014/052487 | 4/2014 |
| WO | 2014/071361 A1 | 5/2014 |

OTHER PUBLICATIONS

Lou et al, "High-throughput DNA sequencing errors are reduced by orders of magnitude using circle sequencing." Proc Natl Acad Sci U S A. Dec. 3, 2013;110(49):19872-7.

Cibulskis et al., "Sensitive detection of somatic point mutations in impure and heterogeneous cancer samples", Nat Biotechnol 31(3) 213-219 (2013).

Flaherty et al., "Ultrasensitive detection of rare mutations using next-generation targeted resequencing", Nucleic Acids Res 40(1) e2 (2012).

Forshew et al., "Noninvasive identification and monitoring of cancer mutations by targeted deep sequencing of plasma DNA", Sci Transl Med 4(136) 136ra68 (2012).

Kaboev et al., "PCR hot start using primers with the structure of molecular beacons (hairpin-like structure)", Nucleic Acids Res 28(1) E94 (2000).

Kinde et al., "Detection and quantification of rare mutations with massively parallel sequencing", Proc Natl Acad Sci USA 108(23) 9503-9535 (2011).

Li et al., "A new approach for detecting low-level mutations in next-generation sequence data", Genome Biol 13(5) R34 (2012).

McCloskey et al., "Encoding PCR products with batch-stamps and barcodes", Biochem Genet 45(11-12) 761-767 (2007).

Schmitt et al., "Detection of ultra-rare mutations by next-generation sequencing", Proc Natl Acad Sci USA 109(36) 14508-14513 (2012).

Schmittgen et al., "Real-time PCR quantification of precursor and mature microRNA", Methods 44(1) 31-38 (2008).

Tong et al., "Detection of restriction enzyme-digested target DNA by PCR amplification using a stem-loop primer: application to the detection of hypomethylated fetal DNA in maternal plasma", Clin Chem 53(11) 1906-1914 (2007).

* cited by examiner

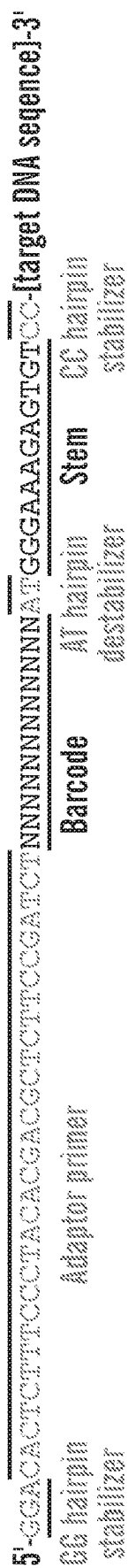
FIG. 6A
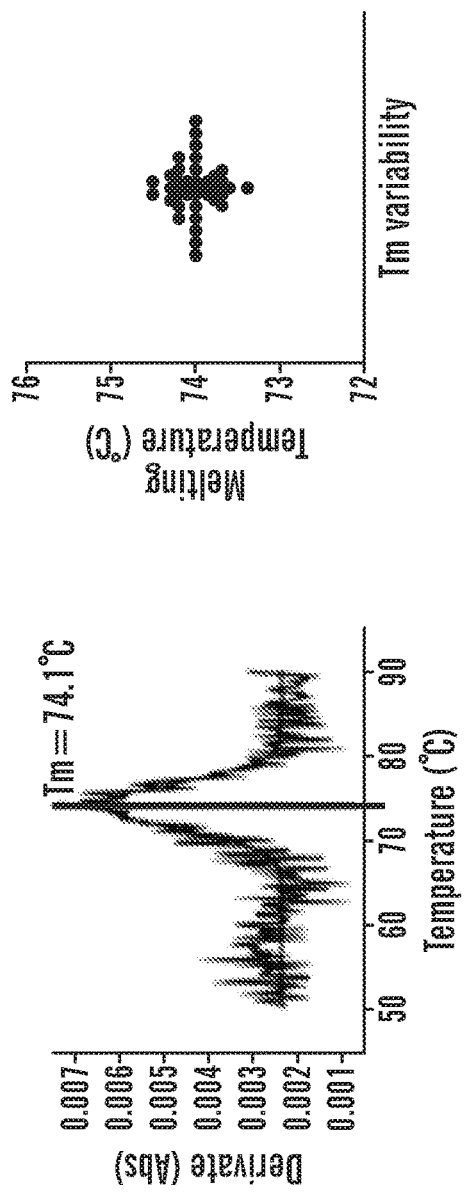
FIG. 6C
FIG. 6D
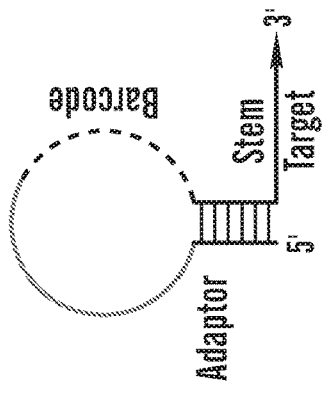
FIG. 6B

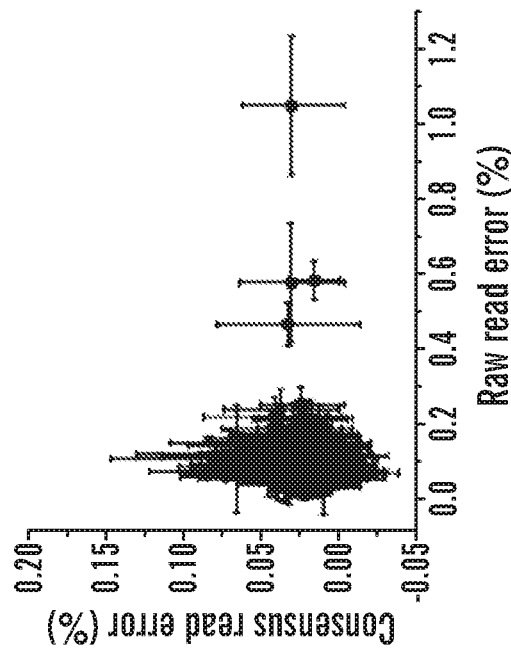
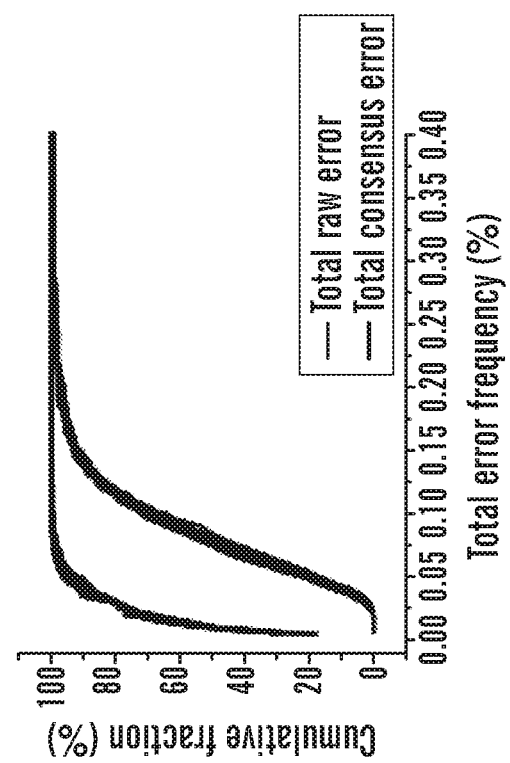
FIG. 9B
FIG. 9A

SEQUENCE LISTING

<160> NUMBER OF SEQ ID NOS: 127

<210> SEQ ID NO 1
<211> LENGTH: 85
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (36)..(47)
<223> OTHER INFORMATION: a, c, t, g, unknown or other

<400> SEQUENCE: 1

```
ggacactctt tccctacacg acgctcttcc gatctnnnnn nnnnnnnatg ggaaagagtg    60
tcccttgctt acctcgctta gtgct                                         85
```

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

```
gtcccagaaa tatgggtggc ata                                           23
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
gatcttccag atagccctgg ac                                            22
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
cctccaccac ctcctcaaac                                               20
```

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
ctgttcctat gggttcattt ccaaga                                        26
```

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
tgttgatgaa gtcatcgaca tcca                                          24
```

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcaaggtttg tctacagaaa tgaaagca                                28

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggatgcatgt cttccgtcca                                         20

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aggtaataac ataccagttt tcccctct                                28

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
actcaccgca caaccatcat                                         20

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
actatactta caaagccatc cattgcc                                 27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgctgttcct cggaaagtct at                                      22

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttgttcctca aactttacag aggag                            25

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctactgttg gattgattcg aaatctt                          27

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggtgattac agcggcatga                                  20

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tttacctcta ttgttggatc atattcgtcc a                     31

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcctgctgaa aatgactgaa tataaacttg                       30

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggatccatcg tattcacacc tttcaatt                         28

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgatatagg catcaaagca tccattttg                        29

```
<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttacagagta acagactagc tagagac                                          27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catacattcg aaagaccta gccttag                                           27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtaagtgtta ctcaagaagc agaaagg                                          27

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agttccctca gccgttacct                                                  20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccgcagatcc gttggaagta                                                  20

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccgctgcaga acaagcttc                                                   19
```

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
aacgcttgct tctcctgtct t          21

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ggtgatagcc gccggttc          18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
gtggtgaggc tccccttt          18

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gacctcaggc ggctcatag          19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
acaacctccg tcatgtgctg          20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
agacctcagg cggctcatag          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ggtggcaagt ggctcctgac                                               20

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
cttgcttacc tcgcttagtg ct                                            22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cctggagtct tccagtgtga tg                                            22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
cttcatctgg acctgggtct tc                                            22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ccaggcattg aagtctcatg ga                                            22

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gcaccttcct gaatagcttt ccaa                                          24

<210> SEQ ID NO 38

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tccactctct ctcttttcag cagta                                           25

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcatttactg cagcttgctt aggt                                            24

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aacaataaac tggagtacac aaggca                                          26

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gatattgcca ccctccagaa tcc                                             23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gacaacttac catcttcccc aga                                             23

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gagtccacca tgaagccaca                                                 20

<210> SEQ ID NO 44
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcacctactc actaactttt ctgttcct                                          28

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
catcagtcag cagcctggta                                                   20

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gccaggaagc tcgcctaat                                                    19

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acactacctc cactggtgag t                                                 21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgtgaacatc ccgagctagg a                                                 21

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccacccatgg acgtacgg                                                     18

<210> SEQ ID NO 50
<211> LENGTH: 30
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 50
acagataggt ataggagtct atgtgcattt                                        30

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gcctgctgaa aatgactgaa tataaacttg tg                                     32

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctgtatcgt caaggcactc tt                                                22

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tcaagtggtg gtcagtacag acata                                             25

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cttatctccg gccctgcatt ta                                                22

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agcacttacc tgtgactcca taga                                              24

<210> SEQ ID NO 56
<211> LENGTH: 27
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 56
gtggaagatc aatccatttt ttgttgt                                          27

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgattgagga tcttttcttc acggtt                                           26

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tctgtcctta ttttggatat ttctcccaat g                                     31

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtgccacata gtgcgtgtt                                                   19

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
atggcaaagg gtgcgttaaa c                                                21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ggcctcgact tccttcttga                                                  20

<210> SEQ ID NO 62
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 62
gcttgcggat gagctcgta                                                    19

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
actgggacgg aacagctttg                                                   20

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gattcctcac tgattgctct taggt                                             25

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cctcaacaag atgttttgcc aactg                                             25

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtggaaggaa atttgcgtgt gga                                               23

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gtaccaccat ccactacaac tacatgtgta a                                      31

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 68
actgggacgg aacagctttg					20

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gactgtacca ccatccacta caac					24

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctggtcctct gactgctctt t					21

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggtttccgtc tgggcttctt					20

<210> SEQ ID NO 72
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (36)..(47)
<223> OTHER INFORMATION: a, c, t, g, unknown or other

<400> SEQUENCE: 72
ggacactctt tccctacacg acgctcttcc gatctnnnnn nnnnnnnatg ggaaagagtg		60 tcc					63

<210> SEQ ID NO 73
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gtgactggag ttcagacgtg tgctcttccg atct					34

<210> SEQ ID NO 74

```
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aatgatacgg cgaccaccga gatctacact ctttccctac acgacgctct tccgatct        58

<210> SEQ ID NO 75
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(30)
<223> OTHER INFORMATION: a, c, t, g, unknown or other

<400> SEQUENCE: 75
caagcagaag acggcatacg agatnnnnnn gtgactggag ttcagacgtg tgctcttccg       60
atct                                                                   64

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gatcggaaga gcacacgtct gaactccagt cac                                   33

<210> SEQ ID NO 77
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
acactctttc cctacacgac gctcttccga tct                                   33

<210> SEQ ID NO 78
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78 atcacg                                                                  6

<210> SEQ ID NO 79
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
```

```
cgatgt                                                              6

<210> SEQ ID NO 80
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80 ttaggc                                                              6

<210> SEQ ID NO 81
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81 tgacca                                                              6

<210> SEQ ID NO 82
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82 acagtg                                                              6

<210> SEQ ID NO 83
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83 gccaat                                                              6

<210> SEQ ID NO 84
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84 cagatc                                                              6

<210> SEQ ID NO 85
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
``` acttga                                                                    6

<210> SEQ ID NO 86
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86 gatcag                                                                    6

<210> SEQ ID NO 87
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87 tagctt                                                                    6

<210> SEQ ID NO 88
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88 ggctac                                                                    6

<210> SEQ ID NO 89
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89 cttgta                                                                    6

<210> SEQ ID NO 90
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90 agtcaa                                                                    6

<210> SEQ ID NO 91
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91 agttcc                                                                    6

```
<210> SEQ ID NO 92
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92 atgtca                                                                    6

<210> SEQ ID NO 93
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93 ccgtcc                                                                    6

<210> SEQ ID NO 94
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94 gtagag                                                                    6

<210> SEQ ID NO 95
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95 gtccgc                                                                    6

<210> SEQ ID NO 96
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96 gtgaaa                                                                    6

<210> SEQ ID NO 97
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97 gtggcc                                                                    6
```

```
<210> SEQ ID NO 98
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98 gtttcg                                                                    6

<210> SEQ ID NO 99
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99 cgtacg                                                                    6

<210> SEQ ID NO 100
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100 gagtgg                                                                    6

<210> SEQ ID NO 101
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101 ggtagc                                                                    6

<210> SEQ ID NO 102
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102 actgat                                                                    6

<210> SEQ ID NO 103
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103 atgagc                                                                    6
```

```
<210> SEQ ID NO 104
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104 attcct                                                                       6

<210> SEQ ID NO 105
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105 caaaag                                                                       6

<210> SEQ ID NO 106
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106 caacta                                                                       6

<210> SEQ ID NO 107
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107 caccgg                                                                       6

<210> SEQ ID NO 108
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108 cacgat                                                                       6

<210> SEQ ID NO 109
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109 cactca                                                                       6

<210> SEQ ID NO 110
```

```
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110 caggcg                                                                       6

<210> SEQ ID NO 111
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111 catggc                                                                       6

<210> SEQ ID NO 112
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112 catttt                                                                       6

<210> SEQ ID NO 113
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113 ccaaca                                                                       6

<210> SEQ ID NO 114
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114 cggaat                                                                       6

<210> SEQ ID NO 115
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115 ctagct                                                                       6

<210> SEQ ID NO 116
<211> LENGTH: 6
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116 ctatac                                                                   6

<210> SEQ ID NO 117
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117 ctcaga                                                                   6

<210> SEQ ID NO 118
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118 gacgac                                                                   6

<210> SEQ ID NO 119
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119 taatcg                                                                   6

<210> SEQ ID NO 120
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120 tacagc                                                                   6

<210> SEQ ID NO 121
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121 tataat                                                                   6

<210> SEQ ID NO 122
<211> LENGTH: 6
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 122 tcattc                                                                  6

<210> SEQ ID NO 123
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123 tcccga                                                                  6

<210> SEQ ID NO 124
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124 tcgaag                                                                  6

<210> SEQ ID NO 125
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125 tcggca                                                                  6

<210> SEQ ID NO 126

<400> SEQUENCE: 126

000

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 127

His His His His His His
1               5
```

PROTECTION OF BARCODES DURING DNA AMPLIFICATION USING MOLECULAR HAIRPINS

CROSS-REFERENCE TO RELATED APPLICATIONS

This application is a 35 U.S.C. § 371 National Phase Entry Application of International Application No. PCT/US2016/019264 filed Feb. 24, 2016, which designated the U.S., and which claims benefit under 35 U.S.C. § 119(e) of U.S. Provisional Application Ser. No. 62/120,183 filed Feb. 24, 2015, the contents of each of which are incorporated herein by reference in entireties.

GOVERNMENT SUPPORT PARAGRAPH

This invention was made with Government Support under Contract No. CA172999 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 17, 2017, is named 701586-082152-SL.txt and is 29,736 bytes in size.

FIELD OF THE INVENTION

The invention generally relates to methods for the detection, identification, and/or quantification of target nucleic acids in a sample.

BACKGROUND

Next-generation sequencing (NGS) is now widely used in cancer research and is also becoming an important clinical tool. Using targeted libraries, NGS can interrogate specific genome regions at extremely high depth and therefore identify rare mutations even in relatively heterogeneous clinical samples such as cytology samples or bodily fluids.

However, mutant detection levels are still limited by the error rate inherent in current NGS protocols, such that reliable detection of mutant fractions below 1-2% remains challenging. While this is adequate for many applications, there are a number of very exciting avenues of cancer research that require even more sensitive approaches. Perhaps the best example of this is the detection of mutations in bodily fluids such as plasma, urine, sputum and others where DNA from a few cancer cells is present in a vast excess of normal cell DNA. Applications such as cancer diagnosis, monitoring response to therapy and monitoring the evolution of tumor heterogeneity via liquid biopsy (plasma) all require detection of mutations at frequencies below 0.1%. Recently developed experimental methods combined with new algorithms for variant calling are capable of achieving this sensitivity but require large amounts of relatively good quality DNA, or can only analyze very limited genomic regions (single PCR amplicons).

SUMMARY OF THE INVENTION

Described herein are approaches for the detection, identification, and/or quantification of target nucleic acids, including, but not limited to, rare target nucleic acids found in bodily fluids, such as plasma, urine, sputum, etc. These approaches provide a means of detecting, identifying, and/or quantifying target nucleic acid molecules, including DNA and RNA molecules, using stem-loop or hairpin primers comprising unique ID (UID) or barcode sequences and adaptor sequences, termed herein as "hairpin barcode primers" that are "hidden," "protected," or "sequestered" during the first few cycles of PCR amplification, thus allowing for multiplexing while reducing non-specific PCR priming. These approaches also allow the efficient generation of libraries for a variety of applications, such as, for example, next generation sequencing.

Accordingly, described herein, in part, are novel approaches for the amplification, detection and/or quantification of a plurality of target nucleic acid sequences based on using hairpin barcode primers, each specific for one of the target nucleic acids being detected and comprising a unique sequence that serves as a barcode or unique identifier for a given target nucleic acid. The unique design and structure of the hairpin barcode primers described herein "hides" the barcode and adaptor sequences when the temperature is at or below the "closed annealing temperature," during the initial cycles of amplification. By hiding the barcode and adaptor sequences in a hairpin structure, mispriming of target sequences with the barcode sequences is inhibited or prevented, and hence the formation of non-specific PCR products is inhibited, even when the starting sample has small amounts of the target nucleic acid(s). In some embodiments of these methods and approaches, further approaches can be taken to reduce formation of non-specific products, such as the use of non-conventional nucleotides in the hairpin barcode primers, reducing the hairpin barcode primer concentrations, using high-fidelity polymerases during the amplification steps.

Accordingly, provided herein, in some aspects, are methods for amplifying a target nucleic acid in a sample comprising: (a) contacting a sample comprising a target nucleic acid with a target-specific hairpin barcode forward primer and a target-specific reverse primer, wherein the hairpin barcode forward primer comprises, in a 5' to 3' direction: a 5' stem sequence, an adaptor sequence, a barcode sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature; (b) amplifying the target nucleic acid by performing 2-5 cycles of PCR pre-amplification on the target nucleic acid, wherein the 2-5 cycles of PCR pre-amplification have an annealing temperature less than or equal to the closed annealing temperature of the hairpin barcode forward primer, to generate a plurality of pre-amplification target nucleic acids; (c) contacting the plurality of pre-amplification target nucleic acids with an adaptor-specific forward primer and an adaptor-specific reverse primer; and (d) amplifying the pre-amplification target nucleic acid by performing at least 10 cycles of PCR amplification on the pre-amplification target nucleic acids, wherein at least 3 of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

In some aspects, provided herein are methods for amplifying a target nucleic acid in a sample comprising: (a) contacting a sample comprising a target nucleic acid with a target-specific hairpin barcode forward primer and a target-specific reverse primer, wherein the hairpin barcode forward primer comprises, in a 5' to 3' direction: a 5' stem sequence, an adaptor sequence, a barcode sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature; and (b) amplifying the target nucleic acid by performing 2-5 cycles of PCR pre-amplification on the target nucleic acid, wherein the 2-5 cycles of PCR pre-amplification have an annealing temperature less than or equal to the closed annealing temperature of the hairpin barcode forward primer, to generate a plurality of pre-amplification target nucleic acids.

In some embodiments of these aspects and all such aspects described herein, the method further comprises a step (c) of contacting the plurality of pre-amplification target nucleic acids with an adaptor-specific forward primer and an adaptor-specific reverse primer; and a step (d) of amplifying the pre-amplification target nucleic acid by performing at least 10 cycles of PCR amplification on the pre-amplification target nucleic acids, wherein at least 3 of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

In some embodiments of these aspects and all such aspects described herein, the method further comprises a step (c) of contacting the plurality of pre-amplification target nucleic acids with an adaptor-specific forward primer and an adaptor-specific reverse primer; and a step (d) of amplifying the pre-amplification target nucleic acid by performing at least 10 cycles of PCR amplification on the pre-amplification target nucleic acids, wherein all of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

In some embodiments of these aspects and all such aspects described herein, the 3' stem sequence is 12-15 nucleotides.

In some embodiments of these aspects and all such aspects described herein, the 3' stem sequence and the adaptor sequence each comprise sequence complementary to each other and the complementary sequences hybridize to each other at a closed annealing temperature and do not hybridize to each other at an open annealing temperature.

In some embodiments of these aspects and all such aspects described herein, the 3' stem sequence and the adaptor sequence comprise 10-12 nucleotides of sequence completely complementary to each other.

In some embodiments of these aspects and all such aspects described herein, the hairpin barcode forward primer further comprises at least two destabilizing nucleotides 3' of the barcode sequence.

In some embodiments of these aspects and all such aspects described herein, the closed annealing temperature is equal to or less than 60° C.

In some embodiments of these aspects and all such aspects described herein, the open annealing temperature is at least 65° C.

In some embodiments of these aspects and all such aspects described herein, the barcode sequence is 6-18 nucleotides.

In some embodiments of these aspects and all such aspects described herein, the barcode sequence is 14 nucleotides.

In some embodiments of these aspects and all such aspects described herein, the hairpin barcode forward primer comprises one or more non-conventional nucleotides.

In some embodiments of these aspects and all such aspects described herein, the target-specific reverse primer is a hairpin barcode reverse primer, wherein the hairpin barcode reverse primer comprises, in a 5' to 3' direction: a 5' stem sequence, an adaptor sequence, a barcode sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature.

In some embodiments of these aspects and all such aspects described herein, the method further comprises a step of detecting or sequencing the plurality of target nucleic acid amplicons.

Also provided herein, in some aspects, are methods of pre-amplifying a target nucleic acid in a sample comprising: (a) contacting a sample comprising a target nucleic acid with a target-specific hairpin barcode forward primer and a target-specific reverse primer, wherein the hairpin barcode forward primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other, and the complementary sequences hybridize to each other under a closed annealing temperature and do not hybridize to each other at an open annealing temperature; and (b) pre-amplifying the target nucleic acid by performing at least one cycle of PCR pre-amplification on the target nucleic acid, wherein the at least one cycle of PCR pre-amplification has an annealing temperature less than or equal to the closed annealing temperature of the hairpin barcode forward primer, thereby generating a plurality of pre-amplification target nucleic acids.

In some aspects, provided herein are methods of amplifying a target nucleic acid in a sample comprising: (a) contacting a sample comprising a target nucleic acid with a target-specific hairpin barcode forward primer and a target-specific reverse primer, wherein the hairpin barcode forward primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other, and the complementary sequences hybridize to each other under a closed annealing temperature and do not hybridize to each other at an open annealing temperature; (b) pre-amplifying the target nucleic acid by performing at least one cycle of PCR pre-amplification on the target nucleic acid, wherein the at least one cycle of PCR pre-amplification has an annealing temperature less than or equal to the closed annealing temperature of the hairpin barcode forward primer, to generate a plurality of pre-amplification target nucleic acids; (c) contacting the plurality of pre-amplification target nucleic acids with an adaptor-specific forward primer and an adaptor-specific reverse primer; and (d) amplifying the pre-amplification target nucleic acid by performing at least 10 cycles of PCR amplification on the pre-amplification target nucleic acids, wherein the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

In some embodiments of these aspects and all such aspects described herein, the sequence to be protected comprises a barcode sequence.

In some embodiments of these aspects and all such aspects described herein, the sequence to be protected comprises an adaptor sequence.

In some embodiments of these aspects and all such aspects described herein, the sequence to be protected comprises, in the 5' to 3' direction, a barcode sequence and an adaptor sequence.

In some embodiments of these aspects and all such aspects described herein, the 3' stem sequence is 5-20 nucleotides.

In some embodiments of these aspects and all such aspects described herein, the 3' stem sequence is 12-15 nucleotides.

In some embodiments of these aspects and all such aspects described herein, the 3' stem sequence and the adaptor sequence each comprise sequence complementary to each other, and the complementary sequences are hybridized to each other at a closed annealing temperature and do not hybridize to each other at an open annealing temperature.

In some embodiments of these aspects and all such aspects described herein, the 3' stem sequence and the adaptor sequence comprise 10-12 nucleotides of sequence completely complementary to each other.

In some embodiments of these aspects and all such aspects described herein, the hairpin barcode forward primer further comprises at least two destabilizing nucleotides 3' of the barcode sequence.

In some embodiments of these aspects and all such aspects described herein, the at least two destabilizing nucleotides are T and A.

In some embodiments of these aspects and all such aspects described herein, the closed annealing temperature is equal to or less than 60° C.

In some embodiments of these aspects and all such aspects described herein, the open annealing temperature is at least 65° C.

In some embodiments of these aspects and all such aspects described herein, the barcode sequence is 6-18 nucleotides.

In some embodiments of these aspects and all such aspects described herein, the barcode sequence is 14 nucleotides.

In some embodiments of these aspects and all such aspects described herein, the hairpin barcode forward primer comprises one or more non-conventional nucleotides.

In some embodiments of these aspects and all such aspects described herein, the target-specific reverse primer is a hairpin barcode reverse primer, wherein the hairpin barcode reverse primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other and the complementary sequences hybridize to each other under a closed annealing temperature, and do not hybridize to each other at an open annealing temperature.

In some embodiments of these aspects and all such aspects described herein, the method further comprises a step of detecting or sequencing the plurality of target nucleic acid amplicons.

In some embodiments of these aspects and all such aspects described herein, the concentration of target-specific hairpin barcode primer used is less than or equal to 100 nM.

In some embodiments of these aspects and all such aspects described herein, the concentration or unit amount of a DNA polymerase used for pre-amplifying or amplifying is 4-10 fold lower than the concentration or unit amount recommended by the manufacturer.

DEFINITIONS

As used herein, the terms "sample" or "nucleic acid sample" refer to any substance containing or presumed to contain a nucleic acid, and includes, for example, cellular extracts, tissue extracts, or fluid extracts, or any polynucleotide(s) purified or isolated from such cellular, tissue, or fluid extracts, including, but not limited to, plasma, serum, sputum, skin, spinal fluid, lymph fluid, synovial fluid, urine, tears, blood cells, organs, tumors, whole blood, bone marrow, amniotic fluid, hair, semen, anal secretions, vaginal secretions, perspiration, saliva, buccal swabs, and also to samples of in vitro cell culture constituents (including, but not limited to, conditioned medium resulting from the growth of cells (including prokaryotic and eukaryotic cells) in cell culture medium, recombinant cells, and cell components). Samples can comprise cellular or tissue explants obtained from an individual or organism during a medical procedure or intervention, such as a surgical procedure or biopsy. Nucleic acid samples from environmental sources are also included among "samples" to which the methods described herein can be applied. It will be appreciated that target polynucleotides can be isolated from such samples using any of a variety of procedures known in the art. It will be appreciated that target polynucleotides can be cut or sheared prior to analysis, including the use of such procedures as mechanical force, sonication, restriction endonuclease cleavage, or any method known in the art. In general, the target polynucleotides of the present teachings will be single stranded, though in some embodiments the target polynucleotide can be double stranded, and a single strand can result from denaturation. In some embodiments of the methods described herein, there is no separate isolation step, and the methods are directly performed on a sample of interest, such as, for example, cellular extracts or lysates, tissue extracts or lysates, or fluid extracts.

As used herein, "isolated" or "purified" when used in reference to a polynucleotide means that a naturally occurring sequence has been removed from its normal cellular environment or is in a non-natural environment. Thus, an "isolated" or "purified" sequence can be in a cell-free solution or placed in a different cellular environment. The term "purified" does not imply that the sequence is the only polynucleotide present, but that it is essentially free (about 90-95%, up to 99-100% pure) of non-polynucleotide material naturally associated with it.

As used herein, the terms "nucleic acid," "polynucleotide," and "oligonucleotide" generally refer to any polyribonucleotide or poly-deoxyribonucleotide, and includes unmodified RNA, unmodified DNA, modified RNA, and modified DNA. Polynucleotides include, without limitation, single- and double-stranded DNA and RNA polynucleotides.

The term polynucleotide, as it is used herein, embraces chemically, enzymatically or metabolically modified forms of polynucleotides, as well as the naturally occurring chemical forms of DNA and RNA found in or characteristic of viruses and cells, including for example, simple (prokaryotic) and complex (eukaryotic) cells. A nucleic acid polynucleotide or oligonucleotide as described herein retains the ability to hybridize to its cognate complimentary strand. A nucleic acid sample will comprise nucleic acids that serve as templates for and/or substrates for a polymerization reaction. A polynucleotide useful for the methods described herein can be an isolated or purified polynucleotide; it can be an amplified polynucleotide in an amplification reaction, or a transcribed product from an in vitro transcription reaction.

Accordingly, as used herein, the terms nucleic acid, polynucleotide and oligonucleotide also encompass primers and probes, as well as oligonucleotide fragments, and is generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including, but not limited to, abasic sites). There is no intended distinction in length between the term "nucleic acid," "polynucleotide," and "oligonucleotide," and these terms are used interchangeably. These terms refer only to the primary structure of the molecule. An oligonucleotide is not necessarily physically derived from any existing or natural sequence, but can be generated in any manner, including chemical synthesis, DNA replication, DNA amplification, reverse transcription or any combination thereof.

The terms "nucleotide" or "mononucleotide," as used herein, refer to a phosphate ester of a nucleoside, e.g., mono-, di-, tri-, and tetraphosphate esters, wherein the most common site of esterification is the hydroxyl group attached to the C-5 position of the pentose (or equivalent position of a non-pentose "sugar moiety"). The term "nucleotide" includes both a conventional nucleotide and a non-conventional nucleotide which includes, but is not limited to, phosphorothioate, phosphite, ring atom modified derivatives, and the like.

As used herein, the term "conventional nucleotide" refers to one of the "naturally occurring" deoxynucleotides (dNTPs), including dATP, dTTP (or TTP), dCTP, dGTP, dUTP, and dITP.

As used herein, the term "nonextendable nucleotide" refers to nucleotides that prevent extension of a polynucleotide chain by a polymerase. Examples of such nucleotides include dideoxy nucleotides (ddA, ddT, ddG, ddC) that lack a 3'-hydroxyl on the ribose ring, thereby preventing 3' extension by DNA polymerases. Other examples of such nucleotides include, but are not limited to, inverted bases, which can be incorporated at the 3'-end of an oligo, leading to a 3'-3' linkage, which inhibits extension by DNA polymerases.

As used herein, the term "non-conventional nucleotide" refers to a nucleotide that is not a naturally occurring nucleotide. The term "naturally occurring" refers to a nucleotide that exists in nature without human intervention. In contradistinction, the term "non-conventional nucleotide" refers to a nucleotide that exists only with human intervention, i.e., an "artificial nucleotide." A "non-conventional nucleotide" can include a nucleotide in which the pentose sugar and/or one or more of the phosphate esters is replaced with a respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. A non-conventional nucleotide can show a preference of base pairing with another non-conventional or "artificial" nucleotide over a conventional nucleotide (e.g., as described in Ohtsuki et al. 2001, Proc. Natl. Acad. Sci., 98: 4922-4925, hereby incorporated by reference). The base pairing ability may be measured by the T7 transcription assay as described in Ohtsuki et al. (supra). Other non-limiting examples of "non-conventional" or "artificial" nucleotides can be found in Lutz et al. (1998) Bioorg. Med. Chem. Lett., 8: 1149-1152); Voegel and Benner (1996) Helv. Chim. Acta 76, 1863-1880; Horlacher et al. (1995) Proc. Natl. Acad. Sci., 92: 6329-6333; Switzer et al. (1993), Biochemistry 32:10489-10496; Tor and Dervan (1993) J. Am. Chem. Soc. 115: 4461-4467; Piccirilli et al. (1991) Biochemistry 30: 10350-10356; Switzer et al. (1989) J. Am. Chem. Soc. 111: 8322-8323, all of which are hereby incorporated by reference. A "non-conventional nucleotide" can also be a degenerate nucleotide or an intrinsically fluorescent nucleotide.

Because mononucleotides are reacted to make poly- and oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring, and as the "3' end" if its 3' oxygen is not linked to a 5' phosphate of a subsequent mononucleotide pentose ring. As used herein, a nucleic acid sequence, even if internal to a larger oligonucleotide, also can be said to have 5' and 3' ends. As used herein, a nucleic acid sequence, such as a hairpin barcode primer, can comprise smaller portions or sub-sequences, and the positions of each of these portions relative to each other can be described as "5' of" or "3' of" another portion, and the order of portions or sub-sequences can be described as being in the 5' to 3' direction. In addition, when two different, non-overlapping oligonucleotides anneal or hybridize to different regions of the same linear complementary target nucleic acid sequence, and the 3' end of the first oligonucleotide points toward the 5' end of the other, second oligonucleotide, the former can be called the "upstream" oligonucleotide and is considered "5' of" the second oligonucleotide, and the latter the "downstream" oligonucleotide and is "3' of" the first oligonucleotide.

As used herein, "complementary" refers to the ability of a single strand of a polynucleotide (or portion thereof) to hybridize to an anti-parallel polynucleotide strand (or portion thereof) by contiguous base-pairing, i.e., hydrogen bonding, between the nucleotides of the anti-parallel polynucleotide single strands, thereby forming a double-stranded polynucleotide comprising the complementary strands. A first polynucleotide is said to be "completely complementary" to a second polynucleotide strand or portion thereof if each and every nucleotide of the first polynucleotide forms a hydrogen-bonded base-pair with nucleotides within the complementary region of the second polynucleotide. A first polynucleotide or portion thereof is not completely complementary (i.e., "partially complementary") to the second polynucleotide, or portion thereof, if at least one nucleotide in the first polynucleotide does not base pair with the corresponding nucleotide in the second polynucleotide. As understood by one of skill in the art, when a DNA molecule is said to be "complementary" to an RNA sequence, any C, G, or A nucleotides on the RNA molecule is base-paired with the complementary G, C, and T, respectively, on the DNA molecule, while any U nucleotides on the RNA molecule are base-paired with A nucleotides on the DNA molecule. As understood by one of skill in the art, when a DNA molecule is said to be "complementary" to another DNA sequence, any C, G, T, or A nucleotides on the first DNA molecule is base-paired with the complementary G, C, A, and T nucleotides, respectively, on the second DNA molecule. In cases where there is partial complementarity, at least one C, G, T/U, or A nucleotide in the first polynucleotide does not base pair with the corresponding G, C, A, T/U nucleotide in the second polynucleotide.

The degree of complementarity between polynucleotide strands has significant effects on the efficiency and strength of annealing or hybridization between polynucleotide strands. This is of particular importance in extension and amplification reactions, such as those described herein, which depend upon binding and annealing between polynucleotide strands. Accordingly, an oligonucleotide primer, such as a hairpin barcode primer, or a portion thereof, is "complementary" to a strand of a target nucleic acid or to another nucleic acid sequence, if at least 50% (preferably, at least 60%, more preferably at least 70%, at least 80%, still more preferably at least 90% or more, up to and including 100%) of the nucleotides of the primer, or a portion thereof, form base-pairs with nucleotides on the target polynucleotide or to another nucleic acid sequence. Generally, the 3' terminal nucleotide of a primer must base pair with a corresponding nucleotide on a given target polynucleotide for a template-dependent polymerase enzyme to extend the primer. It is understood that a primer or oligonucleotide molecule that is said to be "specific for" a target nucleic acid sequence comprises at least a portion of sequence that is completely complementary to or has a high degree of complementarity to a portion of the sequence of the target nucleic acid.

As used herein, the terms "target nucleic acid," "target RNA," "target DNA," "target oligonucleotide," and "target polynucleotide," refer to a nucleic acid of interest, e.g., a nucleic acid of a particular nucleotide sequence one wishes to amplify, detect and/or quantify in a sample using the approaches described herein. The target polynucleotide can be obtained from any source, and can comprise any number of different compositional components. For example, the target can be nucleic acid (e.g. DNA or RNA), transfer RNA, sRNA, and can comprise nucleic acid analogs or other nucleic acid mimic. The target can be methylated, non-methylated, or both. The target can be bisulfate-treated and non-methylated cytosines converted to uracil. Further, it will be appreciated that "target polynucleotide" can refer to the target polynucleotide itself, as well as surrogates thereof, for example amplification products, and native sequences. In some embodiments, the target polynucleotide is a nucleic acid sequence comprising a rare mutation. The terms can refer to a single-stranded or double-stranded polynucleotide molecule (e.g., RNA, DNA, as the case may be), or a specific strand thereof, to which, for example, an oligonucleotide primer that is "specific for" the target nucleic acid anneals or hybridizes. A target nucleic acid as used herein has at least a portion of sequence that is complementary to a target-specific oligonucleotide molecule, such as hairpin barcode primer.

As used herein, an "oligonucleotide primer" refers to a polynucleotide molecule (i.e., DNA, RNA, artificial nucleotides or a combination thereof) capable of annealing to a portion of a sequence of a target nucleic acid, and providing a 3' end substrate for a polymerase enzyme to produce an enzymatic extension product that is complementary to the nucleic acid to which the polynucleotide is annealed. An oligonucleotide primer can refer to more than one primer and can be naturally occurring, as in, for example, a purified restriction digest, or can refer to a molecule produced synthetically. An oligonucleotide primer can act as a point of initiation for the synthesis of a strand complementary to a sequence of a target nucleic acid, when placed under conditions in which primer extension can be catalyzed. A primer is preferably single-stranded for maximum efficiency in amplification. The conditions for initiation and extension usually include the presence of four different deoxyribonucleoside triphosphates (dNTPs) and a polymerization-inducing agent, such as a DNA polymerase or a reverse transcriptase, in a suitable buffer ("buffer" includes constituents that are cofactors for the enzymatic reactions, and/or which affect pH, ionic strength, etc.) and at a suitable temperature. "Primers" useful in the methods described herein, such as hairpin barcode primers and adaptor primers, are generally less than or equal to 150 nucleotides in length, less than or equal to 140 nucleotides in length, less than or equal to 130 nucleotides in length, less than or equal to 120 nucleotides in length, less than or equal to 110 nucleotides in length, less than or equal to 100 nucleotides in length, less than or equal to 90 nucleotides in length, less than or equal to 80 nucleotides in length, less than or equal to 70 nucleotides in length, less than or equal to 60 nucleotides in length, less than or equal to 50 nucleotides in length, less than or equal to 40 nucleotides in length, less than or equal to 30 nucleotides in length, less than or equal to 20 nucleotides in length, but preferably at least 15 nucleotides in length. In the case of hairpin barcode primers, as described herein, the length is typically in the range of between 50-150 nucleotides, between 60-140 nucleotides, between 50-120 nucleotides, between 60-120 nucleotides, between 60-110 nucleotides, and between 65-100 nucleotides. In the case of adaptor primers, as described herein, the length is typically in the range of between 15-50 nucleotides, between 15-45 nucleotides, between 15-40, between 15-35 nucleotides, and between 15-30 nucleotides.

The term "primer site" or "primer binding site" refers to the segment of the sequence of a target nucleic acid sequence to which a primer hybridizes, i.e., the primer is specific for or complementary to the primer binding site. In other words, a "target-specific sequence" as the term is used herein will bind to the primer binding site of the target nucleic acid. It is preferred, in some embodiments, that a primer oligonucleotide anneals or hybridizes to a target nucleic acid under stringent conditions. That is, in some embodiments, a primer oligonucleotide hybridizes to a target nucleic acid under stringent conditions. By "stringent conditions" is meant that the conditions under which hybridization or annealing is occurring permit only hybridization between nucleic acid sequences that are highly complementary, e.g., only a primer "specific for" the target nucleic acid will hybridize under stringent conditions. Stringent conditions can be achieved, for example, by increasing the temperature of and/or decreasing the salt concentrations in a reaction mixture.

As used herein, the terms "hybridizing" or "annealing" refer to the hydrogen-bonded base-pairing interaction of one oligonucleotide or polynucleotide with another oligonucleotide or polynucleotide (typically an antiparallel or complementary polynucleotide) that results in formation of a duplex, typically termed a "hybridization complex" or a "hybridized duplex." More specifically, when two sequences are said to "hybridize," as the term is used herein, each sequence is in opposite or reverse orientation with respect to the other sequence, e.g., a 5' to 3' sequence anneals to a complementary sequence that is 3' to 5' with respect to the first sequence. The ability of two oligonucleotide sequences to hybridize is a function of not only the complementarity of the two sequences, but also includes such factors as the temperature under which the two sequences are contacted (higher temperatures inhibit annealing of oligonucleotides), the pH and concentrations and identities of the salt(s) in the reaction mixture, and the concentrations of the respective oligonucleotides. It is not a requirement that two oligonucleotides have 100% complementarity over their full length to achieve hybridization. However, the greater the degree of complementarity, the greater the ability of two sequences to hybridize under what are termed "stringent hybridization conditions." Hybridization conditions useful in the methods described herein are well known to those of skill. Hybridization can be performed at elevated temperatures (such as 40-85° C. or 40-80° C.) to provide conditions under which only perfectly matched or substantially identical sequences can form a double-stranded complex. Hybridization can be preceded by brief exposure to denaturing temperature conditions (such as heating to 80-90° C.) to relax secondary structures in short RNA fragments, or to separate strands of pre-existing complexes, e.g., during a PCR amplification, as used in the methods described herein.

As noted above, an indication that two nucleic acid sequences are highly complementary is that the two molecules hybridize specifically to each other under stringent conditions. The phrase "hybridizing specifically to" refers to the binding, duplexing, or hybridizing of a molecule only to a particular nucleotide sequence under stringent conditions. "Stringent hybridization conditions" in the context of nucleic acid hybridization experiments are sequence dependent, and are different under different environmental parameters. Longer sequences hybridize specifically at higher temperatures. The $T_m$ is the temperature (under defined ionic strength and pH) at which 50% of the strands capable of forming a duplex structure are actually involved in such a structure. For DNA-DNA hybrids longer than 50 nucleotides at a pH between 5 and 9, for example, the $T_m$ can be approximated from the equation of Meinkoth and Wahl, *Anal. Biochem.*, 138:267 (1984), which is hereby incorporated by reference in its entirety: $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$ and/or hybridization conditions can be adjusted by one of skill in the art to permit annealing to sequences of the desired complementarity. For RNA-RNA hybrids, the $T_m$ can be approximated from the equation: $T_m$=79.8+18.5(log M)+58.4(XG+XC)+11.8(XG+XC)2−820/L−0.35F, where XG+XC are the mole fractions of G and C respectively in the oligonucleotide, L is the length of the shortest strand in the duplex, and F is the molar concentration of formamide. For DNA-RNA hybrids, the $T_m$ can be approximated from the equation: $T_m$=79.8+18.5 log M+58.4(XG+XC)+11.8 (XG+XC)2−820/L−0.50F, where XG+XC are the mole fractions of G and C respectively in the oligonucleotide, L is the length of the shortest strand in the duplex, and F is the molar concentration of formamide.

Generally, stringent conditions are selected to be about 5° C. lower than the thermal melting point ($T_m$) for the specific sequence and its complement at a defined ionic strength and pH. However, highly stringent conditions can utilize a hybridization at 1, 2, 3, or 4° C. lower than the thermal melting point ($T_m$). Using the equation, hybridization, and desired T, those of ordinary skill will understand that variations in the stringency of hybridization are inherently described. An extensive guide to the hybridization of nucleic acids is found in Tijssen, *Laboratory Techniques in Biochemistry and Molecular Biology Hybridization with Nucleic Acid Probes*, Part I Chapter 2 "Overview of Principles of Hybridization and the Strategy of Nucleic Acid Probe Assays," Elsevier, New York (1993), which is hereby incorporated by reference in its entirety.

Accordingly, as used herein, a "hairpin barcode primer" refers to a polynucleotide, preferably a DNA polynucleotide, preferably single-stranded, of specific sequence length, comprising in the 5' to 3' direction: a 5' stem sequence, a sequence to be protected, such as an adaptor sequence and/or a barcode sequence, a 3' stem sequence, and a 3' target-specific sequence, such that the 5' stem sequence and the 3' stem sequence each comprise sequence complementary to each other, and the complementary sequences of the 5' and 3' stem sequences hybridize to each other under a closed annealing temperature to generate a "stem" and do not hybridize to each other at an open annealing temperature, as those terms are defined herein. When the 5' and 3' stem sequences hybridize to each other and form a stem, the hairpin barcode primer forms a "hairpin" or "stem-loop" at the 5' end of the primer, which is not available for extension by a polymerase during an extension step or amplification reaction, and the primer is said to be in a "closed configuration." Illustrative hairpin barcode primers are depicted, for example, in the drawings. Upon extension of a hairpin barcode primer during the pre-amplification PCR, "extended hairpin barcode primers" are generated, comprising the hairpin barcode primer with a sequence complementary to the target nucleic acid sequence, which form part of the plurality of pre-amplification target nucleic acids, as the term is defined herein. In some embodiments of the methods described herein, the sequence to be protected in the closed configuration comprises an adaptor sequence and/or a barcode sequence. In some embodiments of the methods described herein, only a forward primer of a given primer pair is designed as a hairpin barcode primer. In some embodiments of the methods described herein, only a reverse primer of a given primer pair is designed as a hairpin barcode primer. In some embodiments of the methods described herein, both a forward primer and a reverse primer of a given primer pair are designed as hairpin barcode primers.

The terms "5' stem sequence" or "5' stem portion" refers to the sequence of a hairpin barcode primer that is complementary to and hybridizes with the 3' stem sequence, when the primer is in the closed configuration, i.e., when the temperature is at or below the closed annealing temperature for a given hairpin barcode primer. Typically, the 5' stem sequence is between 5-20 bases long, between 6-19 bases long, between 6-18 bases long, between 7-17 bases long, between 7-16 bases long, between 8-16 bases long, etc. In some embodiments, the 5' stem sequence comprises two or more guanine nucleotides. In some embodiments, the 5' stem sequence comprises two or more cytosine nucleotides. In some embodiments of the methods described herein, the 5' stem sequence comprises a portion of the adaptor sequence. In some embodiments, the 5' stem sequence comprises two 5'guanine nucleotides, also referred to herein as a "GG hairpin stabilizer."

The terms "3' stem sequence" or "3' stem portion" refers to the sequence of a hairpin barcode primer that is complementary to and hybridizes with the 5' stem sequence, and, in some embodiments, to a portion of the adaptor sequence, when the primer is in the closed configuration, i.e., when the temperature is at or below the closed annealing temperature for a given hairpin barcode primer. Typically, the 3' stem sequence is between 5-20 bases long, between 6-19 bases long, between 6-18 bases long, between 7-17 bases long, between 7-16 bases long, between 8-16 bases long, etc. In some embodiments of the methods described herein, the 3' stem sequence is complementary to a portion of the adaptor sequence. In some such embodiments, the 3' stem sequence is complementary to at least 8 nucleotides or bases, at least 9 nucleotides or bases, at least 10 nucleotides or bases, at least 11 nucleotides or bases, at least 12 nucleotides or bases, at least 13 nucleotides or bases, at least 14 nucleotides or bases, at least 15 nucleotides or bases, of the adaptor sequence. In some embodiments, the 3' stem sequence comprises two or more guanine nucleotides. In some embodiments, the 3' stem sequence comprises two or more cytosine nucleotides. In some embodiments, the 3' stem sequence comprises two 3'cytosine nucleotides, also referred to herein as a "CC hairpin stabilizer."

The term "hairpin," or "stem-loop" refers to the partially double-stranded region or structure of the stem-loop primer that forms when the primer is in the closed configuration, and hides or protects or sequesters the sequence to be protected, such as the barcode sequence, i.e., when the 3' stem sequence is hybridized to the 5' stem sequence, and, in some embodiments, to a portion of the adaptor sequence. Generally, the length of the hairpin or stem-loop structure is typically in the range of between 30-150 nucleotides, between 30-140 nucleotides, between 30-130 nucleotides, between 30-120 nucleotides, between 30-110 nucleotides, between 30-100 nucleotides, between 30-100 nucleotides, and between 30-90 nucleotides. In some embodiments, the hairpin or stem-loop structure is between 30-100 nucleotides long. Those in the art will appreciate that loops shorter and longer than the ranges described herein can be identified in the course of routine methodology and without undue experimentation, and that such shorter and longer loops are contemplated by the present teachings. In some embodiments, the loop can comprise an identifying portion, also known as a "barcode," "unique identifier (UID)," or "zipcode."

The terms "adaptor sequence" or "adaptor portion" refers to the portion of a hairpin barcode primer that comprises common sequence found in all hairpin barcode primers, regardless of the target nucleic acid, which allows subsequent amplification of target nucleic acids using a common set of adaptor-specific primers. Typically, the adaptor sequence is between 5-40 bases long, between 5-30 bases long, between 10-30 bases long, between 10-20 bases long, between 15-40 bases long, between 15-30 bases long, between 20-40 bases long, between 20-30 bases long, between 12-15 bases long, etc. In some embodiments of the methods described herein, the 5' portion of the adaptor sequence is complementary to the 3' stem sequence. In some such embodiments, the adaptor sequence is complementary to at least 5 nucleotides or bases, at least 6 nucleotides or bases, at least 7 nucleotides or bases, at least 8 nucleotides or bases, at least 9 nucleotides or bases, at least 10 nucleotides or bases, at least 11 nucleotides or bases, at least 12 nucleotides or bases, at least 13 nucleotides or bases, at least 14 nucleotides or bases, at least 15 nucleotides or bases, of the 3' stem sequence. In some embodiments, an adaptor sequence can comprise one or more restriction sites for enzymatic digestion with a restriction enzyme.

The terms "barcode sequence," "barcode portion," "unique identifier (UID) sequence," "UID portion," and "zipcode sequence" refer to a sequence to be protected within a hairpin barcode primer, specifically the loop portion of the hairpin, that is typically unique and/or typically random, that becomes associated with a particular target nucleic acid sequence upon the hairpin barcode primer being extended and amplified. Under closed annealing temperatures the barcode sequence is hidden or protected or sequestered within the hairpin loop structure of the hairpin barcode primer, and does not get added to target nucleic acid (or sequence complementary to the target nucleic acid). However, when a hairpin barcode primer is in an open configuration, upon annealing to its target nucleic acid sequence, extension of the hairpin barcode primer results in a sequence comprising the barcode and a sequence complementary to the target nucleic acid sequence, such that upon subsequent amplification cycles, target nucleic acid amplicons each comprise a unique barcode sequence or a sequence complementary to the barcode sequence. Typically a barcode sequence is between 6 and 18 nucleotides. In some embodiments, the barcode sequence is 14 nucleotides. In some embodiments, the barcode sequence is 12 nucleotides. In some embodiments, the barcode sequence is 10 nucleotides. In some embodiments, where both the forward and reverse primers are hairpin barcode primers, for example, the barcode sequence is 7 nucleotides. Descriptions of barcodes can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

The terms "3' target-specific portion" or "3' target-specific portion" refers to the single stranded portion of a hairpin barcode primer that is complementary to a target polynucleotide. The 3' target-specific sequence is located downstream or 3' from the 3' stem sequence of the primer, and when the hairpin barcode primer is in the closed configuration, the 3' target-specific sequence is not part of the hairpin or stem-loop. Generally, the 3' target-specific sequence of a hairpin barcode primer is between 10-30 nucleotides long, between 15-30 nucleotides long, and between 15-25 nucleotides long. In some embodiments, the hairpin barcode primer is a forward primer, i.e., hairpin barcode forward primer, such that during an extension or amplification reaction, the hairpin barcode forward primer binds in the first round of the extension or amplification cycle. In some embodiments, both the forward and reverse primers are hairpin barcode primers, as the term is defined herein.

A "polymerase," as used herein, refers to an enzyme that catalyzes polynucleotide synthesis by addition of nucleotide units to a nucleotide chain using DNA or RNA as a template. The term refers to either a complete enzyme as it occurs in nature, or an isolated, active catalytic domain, or fragment. Generally, the polymerase enzyme initiates synthesis at the 3'-end of a primer or oligonucleotide, such as a hairpin barcode primer, annealed or hybridized to a target sequence, and proceeds in the 5'-direction along the target nucleic acid to synthesize a strand complementary to the target nucleic acid until synthesis terminates.

As used herein, the term "thermostable nucleic acid polymerase" refers to an enzyme that is relatively stable to heat when compared, for example, to nucleotide polymerases from *E. coli*, and which catalyzes the template-dependent polymerization of nucleoside triphosphates. A "thermostable nucleic acid polymerase," as the term is used herein, retains enzymatic activity for polymerization and exonuclease activities when subjected to the repeated heating and cooling cycles used in PCR. Preferably, a "thermostable nucleic acid polymerase" has optimal activity at a temperature above 45° C. A representative thermostable polymerase enzyme isolated from *Thermus aquaticus* (Taq) is described in U.S. Pat. No. 4,889,818 and methods for using it in conventional PCR are described in Saiki et al., 1988, Science 239:487 and Gelfand, "Taq DNA Polymerase" in PCR Technology; Principles and Applications for DNA Amplification, Erlich, Ed., Stockton Press, N.Y. (1989), Chapter 2). Thermostable polymerases useful for e.g., PCR and related methods are well known to those of skill in the art and are widely available.

As used herein, "extending" refers to any enzyme-catalyzed, in vitro method for synthesizing a new strand of polynucleotide or elongating an existing polynucleotide or oligonucleotide (e.g., a hairpin barcode primer hybridized to a target nucleic acid) in a template-dependent manner. The act of extending according to the methods described herein, can be a component of amplification, which increases the number of copies of a polynucleotide template sequence with the use of a polymerase. Extending a polynucleotide results in the incorporation of nucleotides into a polynucleotide (including nucleotides complementary to those in the template that comprise a unique identifier sequence, such as a barcode), thereby forming an extended polynucleotide molecule complementary to the polynucleotide template. The extended polynucleotide molecule can be used as a template for PCR amplification or as a template to transcribe polynucleotide molecules. Optionally the transcription can be performed in the presence of labeled nucleotides or ribonucleotides, further facilitating detection and/or quantification. In some embodiments, to prevent extension of a polynucleotide that would be undesirable, the polynucleotide can include a non-extendable base at its 3'-end such as a dideoxy nucleotide or inverted base. Extension can be performed at an elevated temperature to preserve specificity of hybridization, ensuring that only perfectly matched, i.e., completely complementary, sequences are extended by the polymerase.

The term "amplification reaction" refers to an in vitro process for providing multiple copies of a target sequence of nucleic acid, i.e., where more than one copy of a target nucleic acid sequence is made. "Amplifying" refers to a step of subjecting nucleic acids in a solution to conditions sufficient to allow for amplification of a target nucleic acid polynucleotide, if all of the components of the reaction are intact. Components of an amplification reaction include, e.g., primer pairs (a "forward primer" and a "reverse primer"), a polynucleotide template, polymerase, nucleotides, and the like. The term "amplifying" typically refers to an "exponential" increase in the number of copies of a target nucleic acid. However, "amplifying" as used herein can also refer to linear increases in the number of copies of a select target sequence of nucleic acid. Accordingly, the term "amplification reaction mixture" refers to an aqueous solution comprising the various reagents used to amplify a target nucleic acid. These include components such as enzymes, aqueous buffers, salts, amplification primers, target nucleic acid, and nucleoside triphosphates. Depending upon the context, the mixture can be either a complete or incomplete amplification reaction mixture. In some embodiments of the aspects described herein, an amplification reaction is a PCR reaction.

"Polymerase chain reaction" or "PCR" refers to a method whereby a specific segment or subsequence of a target nucleic acid, is amplified in a geometric progression, using repeated cycles of forward and reverse primer annealing, primer extension, and thermal strand separation. PCR is well known to those of skill in the art; see, e.g., U.S. Pat. Nos. 4,683,195 and 4,683,202; and PCR Protocols: A Guide to Methods and Applications, Innis et al., eds, 1990; Sambrook and Russell, MOLECULAR CLONING, A LABORATORY MANUAL (3rd ed. 2001); and CURRENT PROTOCOLS IN MOLECULAR BIOLOGY (Ausubel et al., eds., John Wiley & Sons, Inc. 1994-1997, 2001 version).

"Multiplex amplification" refers to amplification of multiple different target nucleic acid sequences in the same reaction (see, e.g., PCR PRIMER, A LABORATORY MANUAL (Dieffenbach, ed. 1995) Cold Spring Harbor Press, pages 157-171). "Multiplex amplification," as used herein, refers to amplification of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30 or more targets, e.g., at least 50, at least 100, at least 250, at least 500, at least 750, at least 1000, at least 5000 or more, targets.

The term "RT primer site," as used herein, refers to the sequence within a target RNA sequence to which a reverse-transcription primer used for cDNA synthesis is complementary and/or hybridizes. An RT primer site preferably comprises at least 8 nucleotides, more preferably at least 15 nucleotides, within the target RNA.

As used herein, a "corresponding cDNA molecule" refers to a cDNA molecule produced by reverse transcription of a particular target RNA molecule, i.e., the target RNA molecule to which it corresponds.

As used herein, "label" or "detectable label" refers to any moiety or molecule that can be used to provide a detectable (preferably quantifiable) signal. A "labeled nucleotide" (e.g., a NTP or dNTP), or "labeled polynucleotide", is one linked to a detectable label. The term "linked" encompasses covalently and non-covalently bonded, e.g., by hydrogen, ionic, or Van der Waals bonds. Such bonds can be formed between at least two of the same or different atoms or ions as a result of redistribution of electron densities of those atoms or ions. Labels can provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. A nucleotide useful in the methods described herein can be labeled so that the transcribed product can incorporate the labeled nucleotide and becomes detectable. A fluorescent dye is a preferred label according to the methods described herein. Suitable fluorescent dyes include fluorochromes such as Cy5, Cy3, rhodamine and derivatives (such as Texas Red), fluorescein and derivatives (such as 5-bromomethyl fluorescein), Lucifer Yellow, IAE-DANS, 7-Me.sub.2N-coumarin-4-acetate, 7-OH-4-CH.sub.3-coumarin-3-acetate, 7-NH.sub.2-4-CH.sub.3-coumarin-3-acetate (AMCA), monobromobimane, pyrene trisulfonates, such as Cascade Blue, and monobromorimethyl-ammoniobimane (see for example, DeLuca, Immunofluorescence Analysis, in Antibody As a Tool, Marchalonis et al., eds., John Wiley & Sons, Ltd., (1982), which is incorporated herein by reference).

It is intended that the term "labeled nucleotide", as used herein, also encompasses a synthetic or biochemically derived nucleotide analog that is intrinsically fluorescent, e.g., as described in U.S. Pat. Nos. 6,268,132 and 5,763,167, Hawkins et al. (1995, Nucleic Acids Research, 23: 2872-2880), Seela et al. (2000, Helvetica Chimica Acta, 83: 910-927), Wierzchowski et al. (1996, Biochimica et Biophysica Acta, 1290: 9-17), Virta et al. (2003, Nucleosides, Nucleotides & Nucleic Acids, 22: 85-98), the entirety of each is hereby incorporated by reference. By "intrinsically fluorescent", it is meant that the nucleotide analog is spectrally unique and distinct from the commonly occurring conventional nucleosides in their capacities for selective excitation and emission under physiological conditions. For the intrinsically fluorescent nucleotides, the fluorescence typically occurs at wavelengths in the near ultraviolet through the visible wavelengths. Preferably, fluorescence will occur at wavelengths between 250 nm and 700 nm and most preferably in the visible wavelengths between 250 nm and 500 nm.

The terms "detectable label" or "label" include a molecule or moiety capable of generating a detectable signal, either by itself or through the interaction with another label. The "label" can be a member of a signal generating system, and thus can generate a detectable signal in context with other members of the signal generating system, e.g., a biotin-avidin signal generation system, or a donor-acceptor pair for fluorescent resonance energy transfer (FRET) (Stryer et al., 1978, Ann. Rev. Biochem., 47:819; Selvin, 1995, Methods Enzymol., 246:300). In one aspect, a "label" does not require another moiety or member to generate a signal.

As used herein, the term "comprising" or "comprises" is used in reference to compositions, methods, and respective component(s) thereof, that are useful to an embodiment, yet open to the inclusion of unspecified elements, whether useful or not.

As used herein, the term "consisting essentially of" refers to those elements for a given embodiment. The term permits the presence of elements that do not materially affect the basic and novel or functional characteristic(s) of that embodiment of the invention.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The practice of the methods described herein will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Polynucleotide Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995). The practice of the methods described herein can also involve techniques and compositions as disclosed in U.S. Pat. Nos. 5,965,409; 5,665,547; 5,262,311; 5,599,672; 5,580,726; 6,045,998; 5,994,076; 5,962,211; 6,217,731; 6,001,230; 5,963,456; 5,246,577; 5,126,025; 5,364,521; 4,985,129; as well as in U.S. patent application Ser. Nos. 10/113,034; 10/387,286; 10/719,185; 10/600,201; 10/752,123 and 10/719,746. All patents, patent applications, and publications mentioned herein, both supra and infra, are hereby incorporated by reference in their entireties.

BRIEF DESCRIPTION OF THE DRAWINGS

FIGS. 6A-6D depicts an embodiment of SiMSen-Seq. FIG. 6A. Sequence composition of hairpin protected barcode primer. Different sequence elements are indicated by color. FIG. 6B. Schematic design and structure of hairpin protected barcode primer. FIG. 6C. Melting curve analysis of hairpin protected barcode primer using a temperature controlled spectrophotometer. The derivative of the absorption over time is shown. The melting temperature (Tm) where 50% of primers are in an open configuration is indicated. FIG. 6D. Thirty-six different hairpin protected barcode primers were evaluated (Mean=70.01, SD±0.24).

FIG. 8A. Electropherogram of a purified final library targeting one DNA sequence using the Fragment Analyzer. FIG. 8B. Electropherogram of a purified final library targeting 31 DNA sequences using the Fragment Analyzer. FIG. 8C. Relative raw read depth of 31 multiplexed amplicons were analyzed. DNA from tumor cell line CP-A was used.

FIGS. 9A-9D demonstrate that SiMSen-Seq reduces PCR induced errors and enables rare mutant molecule detection. FIG. 9A. Cumulative plot of total raw and consensus reads. Data of 5 amplicons covering 417 nucleotides and 12 replicates using the same CP-A DNA source are shown. The average raw read depth was $2.3*10^6$ per amplicon and the average consensus read depth was 7700 per amplicon when 30 raw reads with the same barcode was applied as cutoff. FIG. 9B. Corresponding 95% confidence intervals of total consensus and raw read errors. FIG. 9C. Dot plot of total read errors for 13 amplicons and 1042 nucleotides. The average raw read depth was $5.5*10^5$ per amplicon and the average consensus read depth was 4700 per amplicon when 10 raw reads with the same barcode was applied as cutoff. The amplicons are ranked by consensus read depth (FIG. 11) and the nucleotides within each amplicon are ranked by their total consensus read error. Consensus reads without any observed errors for a given nucleotide are plotted with half the value of the lowest detected read error. FIG. 9D. Rare mutation detection in TP53. Number of variants per nucleotide is shown with corresponding variant allele frequency on the right side y-axis. Pooled plasma DNA from more than 10 individuals and DNA from a clonal derived cell line (CP-A) were analyzed with SiMSen-Seq (n=3-4). Primary tumor DNA with known mutations (marked *) were spiked into the plasma DNA using different mutated DNA concentrations using 10-fold dilution.

FIG. 13A. Total consensus versus raw read error for 1042 nucleotides in 13 amplicons. FIG. 13B. Distribution of average read errors for total raw and consensus reads. Raw read errors above 1% are not shown.

DETAILED DESCRIPTION

Figure 1:
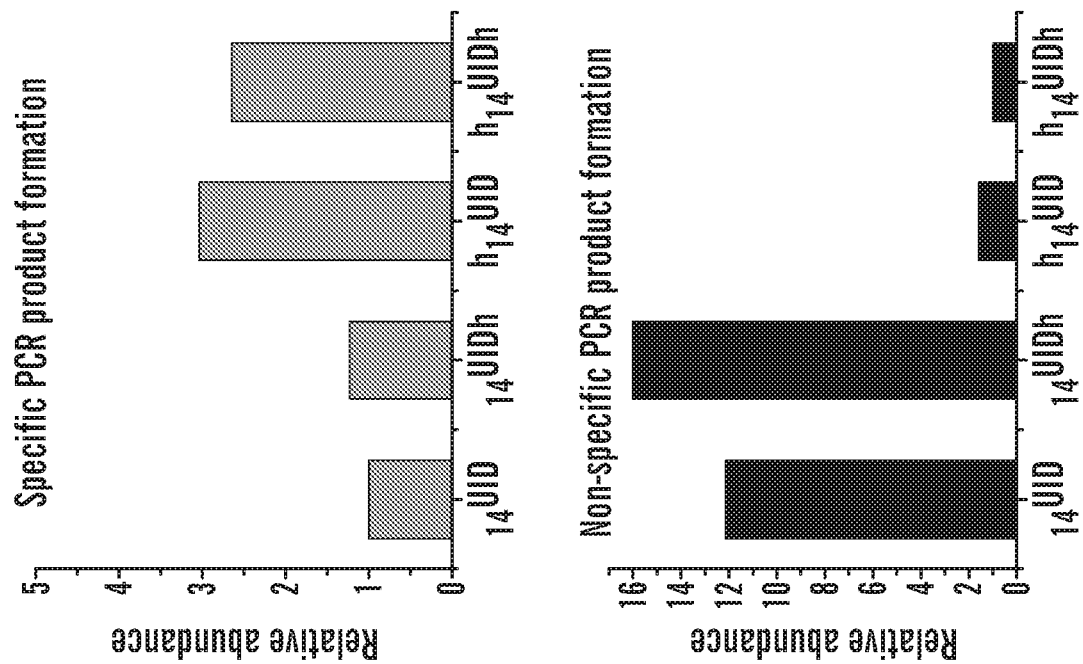
FIG. 1 demonstrates that including hairpin primers increases specific PCR product and reduces non-specific PCR product formation. Gel: Arrows indicate nonspecific product. Box indicates multiplexed PCR products. −ve=no template control. Histogram Quantification by qPCR. Upper=specific product, lower=nonspecific product.
Figure 1:
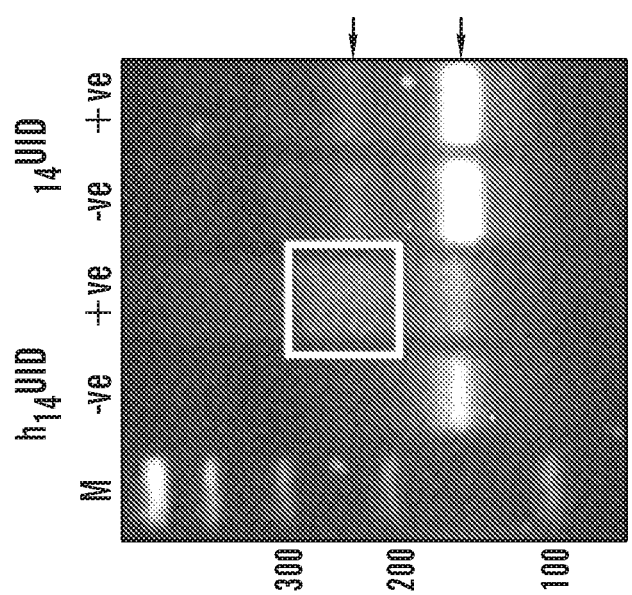

Described herein are approaches for the amplification, detection, and/or quantification of rare target nucleic acid sequences in a biological sample. These methods permit the detection and quantification of individual species of target DNA sequences and/or RNA sequences in a nucleic acid sample, in both single and multiplex format, that permit the amplification and/or determination of the presence of and/or amounts of two or more such target nucleic acid sequences, including rare target nucleic acids, in a single reaction, through the use of hairpin barcode primers that prevent mispriming, and reduce non-specific PCR products, as described herein. The methods described herein reduce and prevent mispriming events during PCR amplification by "hiding," "sequestering," or "protecting," the barcode in a stem-loop hairpin during initial PCR cycles, i.e., the hairpin barcode primer is in a closed configuration, thereby allowing specific target amplification products to form during the initial PCR cycles. This is followed by subsequent PCR amplification cycles where the hairpin barcode primer is in an open configuration, thereby allowing the barcode and adaptor sequences to be added to the specific pre-amplification target products generated during the initial PCR cycles.

Next-generation sequencing (NGS) is widely used in cancer research and is also an important clinical tool. Using targeted libraries, NGS can interrogate specific genome regions at extremely high depth and therefore identify rare mutations even in relatively heterogeneous clinical samples, such as cytology samples or bodily fluids. However, mutant detection levels are still limited by the error rate inherent in current NGS protocols, such that reliable detection of mutant fractions below 1-2% remains challenging. While this is adequate for many applications, there are a number of avenues of cancer research that require even more sensitive approaches. Perhaps one of the best examples of this is the detection of mutations in bodily fluids such as plasma, urine, sputum and other samples, where DNA from a few cancer cells is present in a vast excess of normal cellular DNA. Applications such as cancer diagnosis, monitoring response to therapy, and monitoring the evolution of tumor heterogeneity via liquid biopsy (plasma) all require detection of mutations at frequencies below 0.1%.

Recently developed experimental methods combined with new algorithms for variant calling are capable of achieving this sensitivity, but require large amounts of relatively good quality DNA, or can only analyze very limited genomic regions (single PCR amplicons). When dealing with plasma as an example, typical DNA yields are only 5-10 ng/ml of plasma and the DNA is highly fragmented. In this setting, one typically wishes to interrogate several kilobases of target sequence from different mutation hotspot regions across the genome. Prior to the methods described herein, there was no easy way to do this with a mutation detection sensitivity of under 0.1%.

For cancer diagnosis, or for monitoring clonal evolution of tumors in response to therapy using liquid biopsies, for example, the ability to interrogate several kilobases of DNA for very rare mutations that may occur at any base within the target sequences is needed. Furthermore, the ability to do this starting with relatively small amounts of DNA available from these sample types is required. A tool with this capability would find numerous applications in clinical cancer research and diagnostics. Rare mutation detection with NGS requires very high read depths (for example, a 0.1% mutant would give only one mutant read with a relatively high read depth of 1000×) and this rapidly becomes expensive, even though sequencing costs continue to fall. The major challenge for rare mutation detection with NGS is distinguishing a true mutant signal from background error or noise. Errors in NGS originate from base misincorporations introduced during library preparation and solid-phase amplification on the sequencer, base misincorporation during sequencing, and base calling errors during detection/image analysis. Depending on the library preparation method, sequencing platform and variant calling algorithm, error rates of 0.05-3% are typically reported depending on the specific mutation type. For single base point mutations, which are the most common mutations in cancer, error rates are typically on the higher side at ~1-3%.

Described herein, in some aspects, are methods that can be used, in part, for NGS library construction and data analysis, that permit highly sensitive mutation detection in several kilobases of target sequence when starting with as little as 2 ng-50 ng of DNA. These methods are based, in part, on incorporation of unique barcode ID's (UID's) or barcodes using hairpin barcode primers into target molecules in a PCR pre-amplification step, thus allowing for high level multiplexing and can achieve <0.05% mutation detection in a >100-plex reaction covering ~2.5 Kb of DNA.

Most NGS approaches rely, in part, on addition of unique ID's (UID's), often referred to as barcodes or indexes, onto the target DNA molecules. By barcoding each individual target DNA strand with a UID (typically a random oligonucleotide sequence of variable length), all sequence reads originating from one target strand can be grouped into "super-families" based on the UID. If the original target contained a mutation, all reads in the super-family will also contain that mutation. Occasional sequencing errors will occur in reads in super-families from wild type targets (and at other bases within a mutant super-family) but can be discounted because they are not represented in the majority of reads. This approach is therefore able to distinguish and eliminate most sources of sequencing errors, with the exception of PCR-induced errors that occur in the very first PCR cycle. This is mitigated by the use of high-fidelity polymerases and the requirement to see the same mutant in more than one super-family. Using this strategy alone or in combination with additional computational modifications, mutation detection rates of <0.1% are readily achievable.

However, there are important limitations with the existing approaches. For example, most are based on ligation of barcoded adapters and, while this allows for target selection and generation of complex sequencing libraries, it requires relatively large amounts of DNA (~500 ng and 3 μg in published reports). Some alternative approaches incorporate barcodes using a small number of initial PCR cycles with primers that include the UID sequence plus an adapter sequence for subsequent amplification. These methods have only been reported with single amplicons, and multiplexing multiple amplicons remains a challenge. Furthermore, these protocols require polyacrylamide gel purification of the PCR product prior to sequencing.

As described herein, we have determined that the major hurdle to multiplexing using barcode primers is that relatively long, non-specific PCR products are formed during the initial PCR cycles and that these products out-compete the desired, specific products during the second round of PCR. These products are primer concatamers, typically referred to as primer dimers. In the case of methods involving barcode primers, these products are longer than in a typical PCR because the barcode primers themselves are required to be long (52-70 bp). The increased length of the primer dimers is problematic as it becomes hard to separate them from the desired PCR products using standard, bead-based library clean-up methods, leading to the need for PAGE gel purification methods, for example.

Accordingly, described herein are methods and approaches to address the current limitations in rare mutation detection from sub-optimal samples. Provided herein, in some aspects, are multiplex PCR-based approaches for barcode incorporation that can target several kilobases of DNA. These methods use stem-loop or hairpin barcode primers designed to "hide" or "sequester" or "protect" the degenerate barcode sequence during the first one to three, for example, PCR cycles, referred to herein as "PCR pre-amplification cycles," thus greatly reducing non-specific product formation. In addition, in some embodiments, the barcode labeling step is performed in a picoliter digital PCR format to further reduce non-specific PCR priming. In some embodiments, another strategy to increase specific product yield is to perform a size-selection clean-up to remove non-specific product after the barcode PCR pre-amplification, prior to the adapter primer PCR amplification. Following clean-up, a second round of PCR amplification can be performed using the adapter primers and the most effective clean-up approach can be determined by, for example, gel electrophoresis, quantitative PCR, and/or library sequencing on a MiSeq. In some embodiments, another strategy to increase specific product yield is to evaluate the use of picoliter droplet PCR (dPCR) during library construction. In the droplet PCR workflow, the complete 25-50 μl PCR reaction mix is first converted into 5-10 million, 5 picoliter droplets, each now comprising an independent PCR reaction. dPCR is performed as usual following which the droplets are broken and the aqueous phase can be used directly for downstream applications. With input DNA amounts in the 50-100 ng range (15-30,000 copies of each target), >90% of the droplets contain no target DNA, while those that do contain DNA only have a single copy of one target on a fragment of DNA. Thus, the target complexity is greatly reduced in each droplet compared with the original PCR reaction mix and this reduces non-specific PCR product. This can be particularly helpful in the barcode PCR cycles when formation of non-specific product is initiated. However, an additional advantage of dPCR is the lack of competition between different PCR amplicons, as each droplet only contains one target. This allows each PCR reaction to achieve maximal yield and can result in more uniform depth of sequence coverage if used in the second round of PCR with adapter primers, in some embodiments.

The components and steps of the methods described herein are provided in more detail below.

Samples

For the methods described herein, a nucleic acid sample, such as a sample comprising multiple target DNA molecules and/or target RNA molecules, e.g., mRNA, microRNA, tRNA, etc., is provided that is suspected to or presumed to contain, comprise, or be comprised by the particular target nucleic acid sequences of interest, i.e., specific, target nucleic acid species or sequence, such as rare cancer mutations. Such a sample includes, for example, cellular extracts, tissue extracts, or fluid extracts, or any polynucleotide(s) purified or isolated from such cellular, tissue, or fluid extracts, including, but not limited to, plasma, serum, sputum, skin, spinal fluid, lymph fluid, synovial fluid, urine, tears, blood cells, organs, tumors, whole blood, bone marrow, amniotic fluid, hair, semen, anal secretions, vaginal secretions, perspiration, saliva, buccal swabs. and also to samples of in vitro cell culture constituents (including, but not limited to, conditioned medium resulting from the growth of cells (including prokaryotic and eukaryotic cells) in cell culture medium, recombinant cells, and cell components). Samples can comprise cellular or tissue explants obtained from an individual or organism during a medical procedure or intervention, such as a surgical procedure or biopsy. Nucleic acid samples from environmental sources are also included among "samples" to which the methods described herein can be applied. It will be appreciated that target polynucleotides can be isolated from samples using any of a variety of procedures known in the art. It will be appreciated that target polynucleotides can be cut or sheared prior to analysis, including the use of such procedures as mechanical force, sonication, restriction endonuclease cleavage, or any method known in the art. In general, the target polynucleotides of the present teachings will initially be single stranded, though in some embodiments the target polynucleotide can be double stranded, and a single strand can result from denaturation.

In some embodiments of the methods described herein, there is no separate isolation step, and the methods are directly performed on a sample of interest, such as, for example, cellular extracts or lysates, tissue extracts or lysates, or fluid extracts.

In some embodiments of the methods described herein, there will need to be a step(s) of isolating the nucleic acid molecules comprising, e.g., multiple target DNA molecules and/or target RNA molecules, from a given sample source, to provide target nucleic acid sequences of interest in a form accessible to performing the methods described herein. Typically, cell lysis, followed by purification of the partially degraded nucleic acid molecules by standard methods known to one of skill in the art, such as phenol/chloroform extraction, electrophoresis, and/or chromatography. Often, such methods can include a step wherein the nucleic acid molecules are precipitated, e.g., with ethanol, and resuspended in an appropriate buffer for subsequent reaction steps, for example, cDNA synthesis or other reactions, as described herein.

In some embodiments of the methods described herein, the isolation steps do not comprise any step of isolating a specific type of nucleic acid, i.e., DNA or RNA, or a specific class of RNA molecule, e.g., mRNA, microRNA, tRNA, etc. In other words, in some embodiments, the isolation steps do not distinguish between different types or classes of nucleic acids, such that the nucleic acids used in subsequent steps comprise most, if not all, the types and classes of nucleic acids found in the original sample.

In other embodiments, the isolation steps can comprise one or more additional steps to further purify the nucleic acid sample. For example, step(s) to isolate or purify all or most classes of RNA molecules, but no DNA molecules, or vice versa. In other embodiments, the one or more additional steps to further purify the nucleic acid sample can be used to isolate or purify a specific class of nucleic acid, e.g., only mRNA molecules etc.

Following such isolation and/or purification steps, in those embodiments of the aspects described herein where one or more target nucleic sequences is an RNA sequence, an isolated/purified sample comprising, e.g., DNA and multiple RNA classes, multiple RNA classes, etc., is first reverse transcribed into one or more cDNAs, as described herein. In some embodiments, following the reverse transcription steps, a sample can be treated to remove the starting RNA template sequences, using any suitable method, including physical, chemical, or enzymatic means, which are known to those of skill in the art, to separate hybridized nucleic acid strands. A preferred physical means for strand separation involves heating the nucleic acid until it is completely (>99%) denatured. Typical heat denaturation involves temperatures ranging from about 80° C. to about 105° C., for times ranging from a few seconds to minutes. Such denaturing methods also kill or terminate any reverse transcriptase activity present in the sample. In some embodiments, RNA-specific degrading enzymes can be used to degrade any RNA remaining following cDNA transcription, such as RNase H.

In some preferred embodiments of the various aspects described herein, two or more target nucleic acid sequences, such as multiple target DNA molecules from one or more sample sources are analyzed in a single reaction using the methods described herein.

Primers

Isolated and/or purified nucleic acid molecules from a sample are incubated or contacted with hairpin barcode primers under hybridization conditions that permit the binding of the primers to the target nucleic acid molecules.

As used herein, a "primer" refers to any polynucleotide sequence that hybridizes to a sequence on a target nucleic acid template and serves as a substrate or point of initiation of nucleic acid synthesis, i.e., is capable of annealing to a portion of a sequence of a target nucleic acid, and providing a 3' end substrate for a polymerase enzyme to produce an enzymatic extension product that is complementary to the nucleic acid to which the polynucleotide is annealed. An oligonucleotide primer can refer to more than one primer and can be naturally occurring, as in, for example, a purified restriction digest, or can refer to a molecule produced synthetically. An oligonucleotide primer can act as a point of initiation for the synthesis of a strand complementary to a sequence of a target nucleic acid, when placed under conditions in which primer extension can be catalyzed. A primer is preferably single-stranded for maximum efficiency in amplification. The conditions for initiation and extension usually include the presence of four different deoxyribonucleoside triphosphates (dNTPs) and a polymerization-inducing agent, such as a DNA polymerase or a reverse transcriptase, in a suitable buffer ("buffer" includes constituents that are cofactors for the enzymatic reactions, and/or which affect pH, ionic strength, etc.) and at a suitable temperature.

"Primers" useful in the methods described herein, such as hairpin barcode primers and adaptor primers, are generally less than or equal to 150 nucleotides in length, less than or equal to 140 nucleotides in length, less than or equal to 130 nucleotides in length, less than or equal to 120 nucleotides in length, less than or equal to 110 nucleotides in length, less than or equal to 100 nucleotides in length, less than or equal to 90 nucleotides in length, less than or equal to 80 nucleotides in length, less than or equal to 70 nucleotides in length, less than or equal to 60 nucleotides in length, less than or equal to 50 nucleotides in length, less than or equal to 40 nucleotides in length, less than or equal to 30 nucleotides in length, less than or equal to 20 nucleotides in length, but preferably at least 15 nucleotides in length. In the case of hairpin barcode primers, as described herein, the length is typically in the range of between 50-150 nucleotides, between 60-140 nucleotides, between 50-120 nucleotides, between 60-120 nucleotides, between 60-110 nucleotides, and between 65-100 nucleotides. In the case of adaptor primers, as described herein, the length is typically in the range of between 15-50 nucleotides, between 15-45 nucleotides, between 15-40, between 15-35 nucleotides, and between 15-30 nucleotides.

The term "primer site" or "primer binding site" refers to the segment of the sequence of a target nucleic acid sequence to which a primer hybridizes, i.e., the primer comprises, in part, a sequence that is specific for or complementary to the primer binding site of the target nucleic acid sequence. In other words, a "target-specific sequence" of a primer, as the term is used herein, will bind to the primer binding site of the target nucleic acid. It is preferred, in some embodiments, that a primer oligonucleotide anneals or hybridizes to a target nucleic acid under stringent conditions. That is, in some embodiments, a primer oligonucleotide hybridizes to a target nucleic acid under stringent conditions. By "stringent conditions" is meant that the conditions under which hybridization or annealing is occurring permit only hybridization between nucleic acid sequences that are highly complementary, e.g., only a primer "specific for" the target nucleic acid will hybridize under stringent conditions. Stringent conditions can be achieved, for example, by increasing the temperature of and/or decreasing the salt concentrations in a reaction mixture.

In some aspects and embodiments, methods described herein comprise different amplification steps, such as PCR, to first amplify the target nucleic acids using hairpin barcode primers and, subsequently, amplify the pre-amplification target nucleic acids generated with adaptor-specific primers, thus forming "target nucleic acid amplicons" comprising an adaptor sequence, a barcode sequence, and the target nucleic acid sequence (or complementary sequences thereof). Such amplification steps can further comprise the use of additional oligonucleotide primer pairs, i.e., sets of "forward" and "reverse" adaptor primers, as further described herein. The length and sequences of primers for use in PCR can be designed based on principles known to those of skill in the art, see, e.g., Innis M A and Gelfand D H (1990; "Optimization of PCRs." In: PCR protocols. A guide to methods and applications. Academic Press, Inc, Chapter 1:3-12.).

Oligonucleotide primers for use in the methods described herein can be prepared using any suitable method known to those skilled in the art, such as, for example, methods using phosphotriesters and phosphodiesters. In some embodiments, one or more phosphorothioate linkages can be included in the primers. The oligonucleotide primer can also be modified at the base moiety, sugar moiety, or phosphate backbone with minor groove binders, intercalating agents and the like, so long as its ability to specifically bind template and serve as substrate for polymerase extension (for those embodiments requiring extension) are maintained.

Primers are typically designed so that all primers participating in a particular reaction, pre-amplification step, or amplification step, have melting temperatures that are within 10° C., preferably within 5° C., and most preferably within 2° C. of each other. Primers are further designed to avoid priming on themselves or another primer as templates in a reaction. It is also preferred a given set of oligonucleotide primers do not have complementarity to each other in their 3' ends.

The primers must be sufficiently complementary to their respective target nucleic acid strands to anneal or hybridize selectively and form stable duplexes. In some embodiments, oligonucleotide primers are designed to comprise a target-specific sequence that is exactly complementary to a target nucleic acid sequence. In other embodiments, base-pair mismatches or sites of non-complementarity can be included, e.g., to detect gene homologs where sequence information is lacking. In those embodiments where one or more mismatches are to be included in an oligonucleotide primer or primer set, it is preferred that the mismatches or non-complementary sites occur at the 5' end of the target-specific sequence, as the closer a mismatch is to the 3' end of a target-specific sequence, the more likely it is to prevent extension of the annealed primer.

As understood by one of skill in the art, when a DNA molecule is said to be "complementary" to an RNA sequence, any C, G, or A nucleotides on the RNA molecule is base-paired with the complementary G, C, and T, respectively, on the DNA molecule, while any U nucleotides on the RNA molecule are base-paired with A nucleotides on the DNA molecule. As understood by one of skill in the art, when a DNA molecule is said to be "complementary" to a DNA sequence, any C, G, T, or A nucleotides on the first DNA molecule is base-paired with the complementary G, C, A, and T nucleotides, respectively, on the second DNA molecule. In some embodiments of the methods described herein, a primer can comprise a 5' end sequence of "n" nucleotides that is not complementary to a target sequence and a 3' end that is highly complementary to or exactly complementary to a target nucleic acid sequence, such that extension of the primer hybridized to a target RNA or DNA sequence generates a product comprising an extra "n" nucleotides. For example, the hairpin barcode primers described herein add additional nucleotides comprising the barcode and the adaptor sequences to a target nucleic acid sequence.

In the case of an amplification reaction, primer concentrations should be sufficient to bind to the amount of target sequences that are amplified so as to provide an accurate assessment of the quantity of amplified sequence. Those of skill in the art will recognize that the amount or concentration of primer should vary according to the binding affinity of the primers as well as the quantity of sequence to be bound. Typical primer concentrations range from, for example, 1 nM to 1 µM in a reaction. In some embodiments of the methods described herein, a low concentration of a hairpin barcode primer is used, such as a concentration in the range of 1 nM-100 nM, in the range of 1 nM-75 nM, in the range of 1 nM-50 nM, in the range of 1 nM-25 nM, in the range of 5 nM-100 nM, in the range of 5 nM-75 nM, in the range of 5 nM-50 nM, in the range of 5 nM-25 nM, in the range of 10 nM-100 nM, in the range of 10 nM-75 nM, in the range of 10 nM-50 nM, in the range of 10 nM-25 nM, in the range of 25 nM-100 nM, in the range of 25 nM-75 nM, or in the range of 25 nM-50 nM.

The amplification reactions described herein are performed under conditions in which the primers hybridize to the target sequence template, i.e., RNA or DNA template, and are extended by a polymerase. As appreciated by those of skill in the art, such reaction conditions can vary, depending on the target nucleic acid of interest and the composition of the primer. Amplification reaction cycle conditions are selected so that the primers hybridize specifically to the target template sequence and are extended, if the appropriate polymerase is present, and further, when hairpin barcode primers are utilized, to remain in an open or closed configuration as required. Primers that hybridize specifically to a target template enable amplification of the target sequence preferentially in comparison to other nucleic acids that can be present in the sample that is analyzed.

Hairpin Barcode and Adaptor-Specific Primers

One key and distinguishing feature of the aspects and embodiments of the methods described herein is the use of oligonucleotides, preferably single-stranded DNA oligonucleotides, termed "hairpin barcode primers" or "hairpin UID primers" that "hide" or "sequester" or "protect" a sequence(s) to be protected, such as a barcode sequence, at specific annealing temperatures to prevent mispriming and non-specific PCR product formation, but are "open" at specific annealing temperatures to allow incorporation and replication of the sequence(s) to be sequestered, such as barcode and adaptor sequences, to a target nucleic acid or plurality of target nucleic acid species present in a sample.

As described herein, through the use of these hairpin barcode primers, target nucleic acids undergo a few cycles of a pre-amplification PCR in which the annealing temperature is less than or equal to a desired temperature, termed the "closed annealing temperature," under which conditions the hairpin barcode primers remain in a closed configuration, and the sequence(s) to be protected, such as an adaptor sequence and barcode sequence, are not available for PCR amplification, as they are hidden. In subsequent amplification reactions, the PCR cycles use annealing temperatures, termed "open annealing temperatures," that permit the hairpin barcode primer to be in an open configuration, i.e., the temperature is high enough to prevent hybridization of the 3' stem sequence to its complementary 5' stem sequence, and, in some embodiments, adaptor sequence.

Accordingly, as used herein, a "hairpin barcode primer" refers to a polynucleotide, preferably a DNA polynucleotide, preferably single-stranded, of specific sequence length, comprising in the 5' to 3' direction: a 5' stem sequence, a sequence to be protected, such as an adaptor sequence and/or a barcode sequence, a 3' stem sequence, and a 3' target-specific sequence, such that the 5' stem sequence and the 3' stem sequence each comprise sequence complementary to each other, and the complementary sequences of the 5' and 3' stem sequences hybridize to each other under a closed annealing temperature to generate a "stem" and do not hybridize to each other at an open annealing temperature, as those terms are defined herein. When the 5' and 3' stem sequences hybridize to each other and form a stem, the hairpin barcode primer forms a "hairpin" or "stem-loop" at the 5' end of the primer, which is not available for extension by a polymerase during an extension step or amplification reaction, and the primer is said to be in a "closed configuration." Illustrative hairpin barcode primers are depicted, for example, in the drawings. Upon extension of a hairpin barcode primer during the pre-amplification PCR, "extended hairpin barcode primers" are generated, comprising the hairpin barcode primer with a sequence complementary to the target nucleic acid sequence, which form part of the plurality of pre-amplification target nucleic acids, as the term is defined herein. In some embodiments of the methods described herein, the sequence to be protected in the closed configuration comprises an adaptor sequence and/or a barcode sequence. In some embodiments of the methods described herein, only a forward primer of a given primer pair is designed as a hairpin barcode primer. In some embodiments of the methods described herein, only a reverse primer of a given primer pair is designed as a hairpin barcode primer. In some embodiments of the methods described herein, both a forward primer and a reverse primer of a given primer pair are designed as hairpin barcode primers.

The terms "5' stem sequence" or "5' stem portion" refers to the sequence of a hairpin barcode primer that is complementary to and hybridizes with the 3' stem sequence, when the primer is in the closed configuration, i.e., when the temperature is at or below the closed annealing temperature for a given hairpin barcode primer. Typically, the 5' stem sequence is between 5-20 bases long, between 6-19 bases long, between 6-18 bases long, between 7-17 bases long, between 7-16 bases long, between 8-16 bases long, etc. In some embodiments, the 5' stem sequence comprises two or more guanine nucleotides. In some embodiments, the 5' stem sequence comprises two or more cytosine nucleotides. In some embodiments of the methods described herein, the 5' stem sequence comprises a portion of the adaptor sequence. In some embodiments, the 5' stem sequence comprises, in part, two 5'guanine nucleotides, also referred to herein as a "GG hairpin stabilizer."

The terms "3' stem sequence" or "3' stem portion" refers to the sequence of a hairpin barcode primer that is complementary to and hybridizes with the 5' stem sequence, and, in some embodiments, to a portion of the adaptor sequence, when the primer is in the closed configuration, i.e., when the temperature is at or below the closed annealing temperature for a given hairpin barcode primer. Typically, the 3' stem sequence is between 5-20 bases long, between 6-19 bases long, between 6-18 bases long, between 7-17 bases long, between 7-16 bases long, between 8-16 bases long, etc. In some embodiments of the methods described herein, the 3' stem sequence is complementary to a portion of the adaptor sequence. In some such embodiments, the 3' stem sequence is complementary to at least 5 nucleotides or bases, at least 6 nucleotides or bases, at least 7 nucleotides or bases, at least 8 nucleotides or bases, at least 9 nucleotides or bases, at least 10 nucleotides or bases, at least 11 nucleotides or bases, at least 12 nucleotides or bases, at least 13 nucleotides or bases, at least 14 nucleotides or bases, at least 15 nucleotides or bases, of the adaptor sequence. In some embodiments, the 3' stem sequence comprises two or more guanine nucleotides. In some embodiments, the 3' stem sequence comprises two or more cytosine nucleotides. In some embodiments, the 3' stem sequence comprises, in part, two 3'cytosine nucleotides, also referred to herein as a "CC hairpin stabilizer."

The term "hairpin," or "stem-loop" refers to the partially double-stranded region or structure of the stem-loop primer that forms when the primer is in the closed configuration, and hides or protects or sequesters the sequence to be protected, such as the barcode sequence, i.e., when the 3' stem sequence is hybridized to the 5' stem sequence, and, in some embodiments, to a portion of the adaptor sequence. Generally, the length of the hairpin or stem-loop structure is typically in the range of between 30-150 nucleotides, between 30-140 nucleotides, between 30-130 nucleotides, between 30-120 nucleotides, between 30-110 nucleotides, between 30-100 nucleotides, between 30-100 nucleotides, and between 30-90 nucleotides. In some embodiments, the hairpin or stem-loop structure is between 30-100 nucleotides long. Those in the art will appreciate that loops shorter and longer than the ranges described herein can be identified in the course of routine methodology and without undue experimentation, and that such shorter and longer loops are contemplated by the present teachings. In some embodiments, the loop can comprise an identifying portion, also known as a "barcode," "unique identifier (UID)," or "zipcode."

The terms "adaptor sequence" or "adaptor portion" refers to the portion of a hairpin barcode primer that comprises common sequence found in all hairpin barcode primers, regardless of the target nucleic acid, which allows subsequent amplification of target nucleic acids using a common set of adaptor-specific primers. Typically, the adaptor sequence is between 5-40 bases long, between 5-30 bases long, between 10-30 bases long, between 10-20 bases long, between 15-40 bases long, between 15-30 bases long, between 20-40 bases long, between 20-30 bases long, between 12-15 bases long, etc. In some embodiments of the methods described herein, the 5' portion of the adaptor sequence is complementary to the 3' stem sequence. In some such embodiments, the adaptor sequence is complementary to at least 5 nucleotides or bases, at least 6 nucleotides or bases, at least 7 nucleotides or bases, at least 8 nucleotides or bases, at least 9 nucleotides or bases, at least 10 nucleotides or bases, at least 11 nucleotides or bases, at least 12 nucleotides or bases, at least 13 nucleotides or bases, at least 14 nucleotides or bases, at least 15 nucleotides or bases, of the 3' stem sequence. In some embodiments, an adaptor sequence can comprise one or more restriction sites for enzymatic digestion with a restriction enzyme.

The terms "barcode sequence," "barcode portion," "unique identifier (UID) sequence," "UID portion," and "zipcode sequence" refer to a sequence to be protected within a hairpin barcode primer, specifically the loop portion of the hairpin, that is typically unique and/or typically random, that becomes associated with a particular target nucleic acid sequence upon the hairpin barcode primer being extended and amplified. Under closed annealing temperatures the barcode sequence is hidden or protected or sequestered within the hairpin loop structure of the hairpin barcode primer, and does not get added to target nucleic acid (or sequence complementary to the target nucleic acid). However, when a hairpin barcode primer is in an open configuration, upon annealing to its target nucleic acid sequence, extension of the hairpin barcode primer results in a sequence comprising the barcode and a sequence complementary to the target nucleic acid sequence, such that upon subsequent amplification cycles, target nucleic acid amplicons each comprise a unique barcode sequence or a sequence complementary to the barcode sequence. Typically a barcode sequence is between 6 and 18 nucleotides. In some embodiments, the barcode sequence is 14 nucleotides. In some embodiments, the barcode sequence is 12 nucleotides. In some embodiments, the barcode sequence is 10 nucleotides. In some embodiments, where both the forward and reverse primers are hairpin barcode primers, for example, the barcode sequence is 7 nucleotides. Descriptions of barcodes can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

The terms "3' target-specific portion" or "3' target-specific portion" refers to the single stranded portion of a hairpin barcode primer that is complementary to a target polynucleotide. The 3' target-specific sequence is located downstream or 3' from the 3' stem sequence of the primer, and when the hairpin barcode primer is in the closed configuration, the 3' target-specific sequence is not part of the hairpin or stem-loop. Generally, the 3' target-specific sequence of a hairpin barcode primer is between 10-30 nucleotides long, between 15-30 nucleotides long, and between 15-25 nucleotides long. In some embodiments, the hairpin barcode primer is a forward primer, i.e., hairpin barcode forward primer, such that during an extension or amplification reaction, the hairpin barcode forward primer binds in the first round of the extension or amplification cycle. In some embodiments, the hairpin barcode primer is a reverse primer. In some embodiments, both the forward and reverse primers of a given primer pair are hairpin barcode primers, as the term is defined herein.

In some embodiments, a hairpin barcode primer comprises at least two destabilizing nucleotides bases. Such destabilizing bases can be incorporated to ensure that the barcode sequence itself does not, by random chance, complement the adapter sequence (immediately 3' to the portion of the adapter sequence being used in the stem), and results in a longer, more stable stem. In some embodiments of the methods described herein, the at least two destabilizing bases are 3' of the barcode sequence and 5' of the 3' stem sequence. In some embodiments of the methods described herein, the at least two destabilizing bases comprise A and T and are referred to herein as an "AT hairpin destabilizer." For example, an exemplary AT sequence can be used as the at least two destabilizing nucleotides, such as in the following sequence:

```
                                              (SEQ ID NO: 1)
GGACACTCTTTCCCTACACGACGCTCTTCCGATCTNNNNNNNNNNNNN
ATGGGAAAGAGTGTCCCTTGCTTACCTCGCTTAGTGCT.
```

In some embodiments, the hairpin barcode primer is a forward primer, i.e., hairpin barcode forward primer, such that during an extension or amplification reaction, the hairpin barcode forward primer binds in the first round of the extension or amplification cycle. In some embodiments, both the forward and reverse primers are hairpin barcode primers, as the term is defined herein. In some embodiments of the methods described herein, only a reverse primer of a given primer pair is designed as a hairpin barcode primer. In some embodiments of the methods described herein, both a forward primer and a reverse primer of a given primer pair are designed as hairpin barcode primers.

Also provided herein are adaptor-specific primers to be used in amplification of pre-amplification target nucleic acids generated by the hairpin barcode primers described herein. Such adaptor primers, in addition to being specific for a desired adaptor sequence should have an annealing temperature equal to or greater than the open annealing temperature of the hairpin barcode primers used in the pre-amplification PCR, thereby allowing the extended hairpin barcode primers from the pre-amplification PCR to be in the open configuration and thus generating a plurality of target nucleic acid amplicons comprising the adaptor sequence and the barcode sequence and the sequence complementary to the target nucleic acid, as well as extended target nucleic acid sequences comprising the target nucleic acid, and sequences complementary to the adaptor sequence and the barcode sequence.

Numerous factors influence the efficiency and selectivity of hybridization of a given primer to the target nucleic acid. These factors, which include template or target length, nucleotide sequence and/or composition, hybridization temperature, buffer composition and potential for steric hindrance in the region to which the primer is required to hybridize, and the annealing temperatures required to keep a hairpin barcode primer in the open and closed configurations are considered when designing primers useful for the methods described herein. Particular melting temperature ($T_m$) that can be useful in predicting or maximizing specificity can be estimated using, e.g., commercial programs, including, e.g., Oligo-dT Obliged, Primer Design and other programs available on the world wide web, including Primer3 and Oligo Calculator.

Modifications of the primers that can facilitate binding and hybridization to maximize the efficiency of the methods described herein include the incorporation of positively charged or neutral phosphodiester linkages in the primers and prosthetic molecules to decrease the repulsion of the polyanionic backbones of the probe and target (see Letsinger et al., 1988, J. Amer. Chem. Soc: 110:4470); the incorporation of alkylated or halogenated bases, such as 5-bromouridine, to increase base stacking; the incorporation of ribonucleotides to force any duplexes formed into an "A" structure, which has increased base stacking; and the substitution of 2,6-diaminopurine (amino adenosine) for some, or all of the adenosines in the probe. In preparing such modified primers, one should recognize that the rate-limiting step of duplex formation is "nucleation," the formation of a single base pair, and therefore, altering the biophysical characteristic of a portion of the primer, for instance, only the 3' or 5' terminal portion, can suffice to achieve the desired result.

In some embodiments of the methods described herein, one or more locked nucleic acids (LNAs) can be used in a hairpin barcode primer. A "locked nucleic acid" is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs, for example, has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12):3185-3193). Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

In some embodiments of the methods described herein, one or more modified nucleotides can be used in a hairpin barcode primer, such as in the 3' stem sequence. Non-limiting examples of modified nucleotides contemplated for use in the hairpin barcode primers and methods described herein include inosine, xanthine, hypoxanthine, nubularine, isoguanisine, tubercidine, 2-(halo)adenine, 2-(alkyl)adenine, 2-(propyl)adenine, 2 (amino)adenine, 2-(aminoalkyll) adenine, 2 (aminopropyl)adenine, 2 (methylthio) N6 (isopentenyl)adenine, 6 (alkyl)adenine, 6 (methyl)adenine, 7 (deaza)adenine, 8 (alkenyl)adenine, 8-(alkyl)adenine, 8 (alkynyl)adenine, 8 (amino)adenine, 8-(halo)adenine, 8-(hydroxyl)adenine, 8 (thioalkyl)adenine, 8-(thiol)adenine, N6-(isopentyl)adenine, N6 (methyl)adenine, N6,N6 (dimethyl) adenine, 2-(alkyl)guanine, 2 (propyl)guanine, 6-(alkyl) guanine, 6 (methyl)guanine, 7 (alkyl)guanine, 7 (methyl) guanine, 7 (deaza)guanine, 8 (alkyl)guanine, 8 (alkenyl) guanine, 8 (alkynyl)guanine, 8-(amino)guanine, 8 (halo) guanine, 8-(hydroxyl)guanine, 8 (thioalkyl)guanine, 8-(thiol)guanine, N (methyl)guanine, 2-(thio)cytosine, 3 (deaza) 5 (aza)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl)cytosine, 5 (propynyl) cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl) uracil, 5 (guanidiniumalkyl)uracil, 5 (1,3-diazole-1-alkyl) uracil, 5-(cyanoalkyl)uracil, 5-(dialkylaminoalkyl)uracil, 5 (dimethylaminoalkyl)uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo) uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl) pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio) pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio) pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 (aminocarbonylethylenyl)-2,4-(dithio)pseudouracil, 1 (aminoalkylaminocarbonylethylenyl)-pseudouracil, 1 (aminoalkylaminocarbonylethylenyl)-2(thio)-pseudouracil, 1 (aminoalkylaminocarbonylethylenyl)-4 (thio)pseudouracil, 1 (aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5 nitroindole, 3 nitropyrrole, 6-(aza)

pyrimidine, 2 (amino)purine, 2,6-(diamino)purine, 5 substituted pyrimidines, N2-substituted purines, N6-substituted purines, O6-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof.

Nucleic Acid Polymerases

"Nucleic acid polymerases," as used herein, refer to a broad class of enzymes that catalyze the polymerization of individual nucleotides, e.g., deoxyribonucleotides and ribonucleotides, into a nucleic acid strand or polynucleotide in a template-dependent manner. Nucleic acid polymerases generally useful herein include reverse transcriptases, DNA polymerases, RNA polymerases, and mutant or altered forms of any of the foregoing. In some embodiments of the aspects described herein, the enzyme having polymerase activity can comprise a hybrid protein. The term "hybrid protein" is used herein to describe a protein that comprises amino acid residues from more than one parent sequence. Examples of hybrid polymerase proteins and methods of generating hybrid proteins are disclosed in WO2004011605, the contents of which are herein incorporated in their entirety by reference. Such polymerases are therefore non-naturally occurring variants of polymerases.

At least five families of DNA-dependent naturally occurring DNA polymerases are known, although most fall into three families designated A, B and C. There is little or no structural or sequence similarity among the various families. As used herein, a "DNA polymerase" refers to any naturally occurring or recombinant enzyme that catalyzes the polymerization of deoxyribonucleotides into a polynucleotide DNA strand in a template-dependent manner. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases, α, δ, and ε, are implicated in nuclear replication, and a family A polymerase, polymerase γ, is used for mitochondrial DNA replication. Other types of DNA polymerases include phage polymerases.

Endogenous or naturally occurring DNA polymerases are critical for DNA replication, in which the polymerase reads an intact DNA strand as a template, and uses it as template to synthesize the new strand. The newly polymerized molecule is complementary to the template strand, and identical to the template's original partner strand. DNA polymerases can add free nucleotides only to the 3' end of the newly-forming strand, to a preexisting 3'-OH group. Therefore, DNA polymerases require a primer, such as the hairpin barcode primers described herein, to provide a 3'-OH end substrate at which it can add a first nucleotide. This polymerase activity results in elongation of the new strand in a 5'-3' direction. No known DNA polymerase is able to synthesize a new chain de novo.

Nucleic acid polymerases for use in the methods described herein are preferably thermostable. Among the advantages conferred by the thermostability of certain polymerases, such as Taq (*Thermus aquaticus*) DNA polymerase, is the ability to withstand the repeated heating and cooling inherent to PCR amplification reactions, and to synthesize nucleic acid strands at high temperatures. Such high temperatures prevent or do not permit hybridization of mismatched primers, and do not permit or reduce formation of regions of local secondary structure, thus increasing the efficiency and success of the synthesis.

It is preferred that DNA polymerases for use in the methods described herein have low error rates or high fidelity. As used herein, the "error rate" of a DNA polymerase refers to the number of incorrect, i.e., non-complementary base pairs, a DNA polymerase adds to a sequence being synthesized per 10000 nucleotides added per replication cycle. For example, the error rate of Taq polymerase was initially estimated at $2\times10^{-4}$ nucleotides/cycle (Saiki et al., 1988). Typically, polymerases with 3' to 5' exonuclease activity have low error rates, but can sometimes have decreased yields. Accordingly, in some embodiments, a polymerase for use in the methods described herein has 3' to 5' exonuclease activity. In other embodiments, the polymerase has no 3' to 5' exonuclease activity.

A wide variety of DNA polymerases can be used in the methods described herein. Suitable DNA polymerases for use in the subject methods may or may not be thermostable. DNA polymerases and their properties are described in detail in, among other places, DNA Replication 2nd edition, Kornberg and Baker, W. H. Freeman, New York, N.Y. (1991). Known conventional and/or thermostable DNA polymerases useful in the methods described herein include, but are not limited to, *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475: 32), *Thermus aquaticus* (Taq) DNA polymerase (Chien et al., 1976, J. Bacteoriol, 127: 1550), *Thermus flavus* (Tfl) polymerase (Kaledin, A. S. et al. (1981) Biokhimiia 46, 1576-84), Vent☐ polymerase, Pfu polymerase, DNA polymerases derived from thermophilic microorganisms, and *E. coli* DNA polymerase I (Lecomte and Doubleday, 1983, Polynucleotides Res. 11:7505). In some embodiments, the DNA polymerase lacks 5'-nuclease activity. Examples of such polymerases include Klenow fragment of DNA polymerase 1, Stoeffel fragment of Taq polymerase, Pfu polymerase or Vent polymerase. In some embodiments, a thermoactivated DNA polymerase typically referred to as "hot-start" DNA polymerase can be used to perform extension at elevated temperatures. In addition, any mutants, variants, or fragments maintaining polymerase activity and thermostability, are also contemplated for use in the methods described herein.

In some embodiments of the methods described herein, the polymerase used is selected from Takara PRIME STAR GXL polymerase I, Clontech's ADVANTAGE HD Polymerase, NEB Q5® High-Fidelity DNA Polymerases NEB PHUSION® High-Fidelity DNA Polymerases, Thermo-Fisher PLATINUM® Taq DNA Polymerase High Fidelity, ThermoFisher ACCUPRIME™ Pfx DNA Polymerase, ThermoFisher ACCUPRIME™ Taq DNA Polymerase High Fidelity, Promega Pfu DNA Polymerase, and Qiagen HOTSTAR HIFIDELITY Polymerase. In some embodiments of the methods described herein, a polymerase used in a PCR pre-amplification step is selected from Takara PRIME STAR GXL polymerase I, Clontech's ADVANTAGE HD Polymerase, NEB Q5® High-Fidelity DNA Polymerases NEB PHUSION® High-Fidelity DNA Polymerases, ThermoFisher PLATINUM® Taq DNA Polymerase High Fidelity, ThermoFisher ACCUPRIME™ Pfx DNA Polymerase, ThermoFisher ACCUPRIME™ Taq DNA Polymerase High Fidelity, Promega Pfu DNA Polymerase, and Qiagen HOTSTAR HIFIDELITY Polymerase. In some embodiments of the methods described herein, a polymerase used in a PCR pre-amplification step is selected from Takara PRIME STAR GXL polymerase I and ThermoFisher ACCUPRIME™ Taq DNA Polymerase High Fidelity.

In some embodiments of the methods described herein, a low or lower concentration or units of a DNA polymerase is used than is typically used or recommended by the manufacturer when performing PCR amplification, to further reduce non-specific PCR product formation. In some such embodiments, a low or lower concentration or units of a DNA polymerase is used than is typically used or recommended by the manufacturer in a PCR pre-amplification step. As used herein, "low concentration of DNA polymerase" refers to a concentration or units of DNA polymerase that is at least 2-20 fold lower than that the concentration or units recommended by the manufacturer, at least 2-15 fold lower than the concentration or units recommended by the manufacturer, at least 2-10 fold lower than the concentration or units recommended by the manufacturer, at least 4-20 fold lower than the concentration or units recommended by the manufacturer, at least 4-15 fold lower than the concentration or units recommended by the manufacturer, at least 4-10 fold lower than the concentration or units recommended by the manufacturer, at least 5-20 fold lower than the concentration or units recommended by the manufacturer, at least 5-15 fold lower than the concentration or units recommended by the manufacturer, or at least 5-10 fold lower than the concentration or units recommended by the manufacturer. In some embodiments of the methods described herein, the concentration or units of DNA polymerase used, for example in a PCR pre-amplification step(s), is between 4-10 fold lower than the concentration or units recommended by the manufacturer.

Nucleic Acid Amplification

The methods described herein relate to the use of hairpin barcode primers and adaptor-specific primers to amplify target nucleic acid molecules to detect and identify the presence and/or amount of one or more target nucleic acid sequences in the sample, even when such target nucleic acid molecules are in very low amounts in a given sample.

Accordingly, provided herein, in some aspects, are methods for amplifying a target nucleic acid in a sample comprising: (a) contacting a sample comprising a target nucleic acid with a target-specific hairpin barcode forward primer and a target-specific reverse primer, wherein the hairpin barcode forward primer comprises, in a 5' to 3' direction: a 5' stem sequence, an adaptor sequence, a barcode sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature; (b) amplifying the target nucleic acid by performing 2-5 cycles of PCR pre-amplification on the target nucleic acid, wherein the 2-5 cycles of PCR pre-amplification have an annealing temperature less than or equal to the closed annealing temperature of the hairpin barcode forward primer, to generate a plurality of pre-amplification target nucleic acids; (c) contacting the plurality of pre-amplification target nucleic acids with an adaptor-specific forward primer and an adaptor-specific reverse primer; and (d) amplifying the pre-amplification target nucleic acid by performing at least 10 cycles of PCR amplification on the pre-amplification target nucleic acids, wherein at least 3 of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

Provided herein, in some aspects, are methods for amplifying a target nucleic acid in a sample comprising: (a) contacting a sample comprising a target nucleic acid with a target-specific hairpin barcode forward primer and a target-specific reverse primer, wherein the hairpin barcode forward primer comprises, in a 5' to 3' direction: a 5' stem sequence, an adaptor sequence, a barcode sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature; and (b) amplifying the target nucleic acid by performing 2-5 cycles of PCR pre-amplification on the target nucleic acid, wherein the 2-5 cycles of PCR pre-amplification have an annealing temperature less than or equal to the closed annealing temperature of the hairpin barcode forward primer, to generate a plurality of pre-amplification target nucleic acids.

In some embodiments of these aspects, the methods further comprises a step (c) of contacting the plurality of pre-amplification target nucleic acids with an adaptor-specific forward primer and an adaptor-specific reverse primer; and a step (d) of amplifying the pre-amplification target nucleic acid by performing at least 10 cycles of PCR amplification on the pre-amplification target nucleic acids, wherein at least 3 of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

In some embodiments of these aspects, the methods further comprises a step (c) of contacting the plurality of pre-amplification target nucleic acids with an adaptor-specific forward primer and an adaptor-specific reverse primer; and a step (d) of amplifying the pre-amplification target nucleic acid by performing at least 10 cycles of PCR amplification on the pre-amplification target nucleic acids, wherein all of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

Provided herein, in some aspects, are methods for amplifying a target nucleic acid in a sample comprising: (a) contacting a sample comprising a target nucleic acid with a target-specific hairpin barcode forward primer and a target-specific reverse primer, wherein the hairpin barcode forward primer comprises, in a 5' to 3' direction: a 5' stem sequence, a sequence to be protected, such as a barcode sequence and/or an adaptor sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature; and (b) amplifying the target nucleic acid by performing at least one cycle of PCR pre-amplification on the target nucleic acid, wherein the at least one cycle of PCR pre-amplification has an annealing temperature less than or equal to the closed annealing temperature of the hairpin barcode forward primer, to generate a plurality of pre-amplification target nucleic acids.

In some embodiments of these aspects, the methods further comprises a step (c) of contacting the plurality of pre-amplification target nucleic acids with an adaptor-specific forward primer and an adaptor-specific reverse primer; and a step (d) of amplifying the pre-amplification target nucleic acid by performing at least 10 cycles of PCR amplification on the pre-amplification target nucleic acids, wherein at least 3 of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

In some embodiments of these aspects, the methods further comprises a step (c) of contacting the plurality of pre-amplification target nucleic acids with an adaptor-specific forward primer and an adaptor-specific reverse primer; and a step (d) of amplifying the pre-amplification target nucleic acid by performing at least 10 cycles of PCR amplification on the pre-amplification target nucleic acids, wherein all of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

The most common procedure for DNA amplification, the polymerase chain reaction (PCR) technique, is disclosed in U.S. Pat. Nos. 4,683,202; 4,683,195; 4,800,159; and 4,965,188. The PCR method is also described in Saiki et al., 1985, Science 230:1350.

PCR provides an in vitro method for the enzymatic synthesis of specific nucleic acid sequences that uses two oligonucleotide primers that hybridize to opposite strands and flank the region of interest in the target nucleic acid sequence, i.e., a "forward" and "reverse" primer, or "primer pair." A repetitive series of reaction steps involving template denaturation, primer annealing, and the extension of the annealed primers by a DNA polymerase results in the exponential accumulation of a specific target nucleic acid fragment, the termini of which are defined by the 5' ends of the oligonucleotide primers. PCR is capable of producing a selective enrichment of a specific DNA sequence by a factor of at least $10^9$.

In a typical PCR protocol, a nucleic acid sample having a target nucleic acid sequence to be amplified is denatured by heating the sample. In the presence of a nucleic acid polymerase and excess nucleoside triphosphates, oligonucleotide primers that hybridize specifically to the target sequence can prime new nucleic acid synthesis. Generally, oligonucleotide primers are added in vast excess compared to the nucleic acid to be amplified. Under the appropriate conditions, oligonucleotide primers hybridize to opposite strands of a denatured double-stranded nucleic acid sequence and are oriented with their 3' ends facing each other on the two strands, so that synthesis by a nucleic acid polymerase that catalyzes growth of new strands in the 5' to 3' direction extends across the segment of nucleic acid between these primers.

One round of synthesis results in new strands of indeterminate length which, like the parental strands, can hybridize to the primers upon denaturation and annealing. These products accumulate only arithmetically with each subsequent cycle of denaturation, annealing to primers, and synthesis. However, the second cycle of denaturation, annealing, and synthesis produces two single-stranded products that together compose a discrete double-stranded product that is exactly the length between the primer ends. Each strand of this discrete product comprises sequence that is complementary to one of the two primers and can therefore participate as a template in subsequent cycles. A PCR primer that is extended via PCR amplification can also be referred to herein as an extended product thereof, for example, a hairpin barcode extended product thereof. The amount of this product doubles with every subsequent cycle of synthesis, denaturation, and annealing, accumulating exponentially so that 30 cycles theoretically result in a $2^{28}$-fold (270 million-fold) amplification of the target nucleic acid product.

A typical PCR amplification cycle comprises three steps, "denaturation," "annealing" or "hybridizing," and "extension." As used herein, "denaturation" or "nucleic acid melting" refers to the separation or unwinding of double-stranded nucleic acids and separation into single-stranded strands through the breaking of hydrogen bonding between complementary bases. Both terms are used herein to refer to the process as it occurs when a mixture is heated to a specific temperature, although "denaturation" can also refer to the separation of nucleic acid strands induced by chemicals like urea. It is critical that complete strand separation occur during the denaturation step. Higher temperatures required for complete denaturation are associated with high GC content in the nucleic acids. A typical temperature for the denaturing step in a typical PCR cycle is at least 92° C., at least 93° C., at least 94° C., at least 95° C., at least 96° C., at least 97° C., at least 98° C., at least 99° C., or higher. The duration of the denaturing step in a typical PCR cycle is approximately 30 seconds.

The "annealing" or "hybridization" step of a PCR cycle refers to the step wherein the primers and/or probes stably anneal to the template. Primers with relatively low GC content (<50%) can require temperatures lower than 55° C. for full annealing. On the other hand, this can also increase the quantity of nonspecific products. For primers with high GC content, higher annealing temperatures can be tolerated. Methods for optimization of primer annealing are known to one of skill in the art. As with denaturation, the time for this step is based mainly on the time it takes to reach the proper temperature, because the primers are in such excess that the annealing reaction occurs very quickly.

As used herein, a "closed annealing temperature" refers to a temperature at or below which a given hairpin barcode primer, or plurality of hairpin barcode primers used in a given PCR mixture, can both anneal to a target nucleic acid and maintain the hairpin barcode primer, or plurality of hairpin barcode primers in the closed configuration. In other words, temperatures at which the given hairpin barcode primer, or plurality of hairpin barcode primers, or extended products thereof, comprises a stem and loop structure and the adaptor and barcode sequences are not available to bind to non-target sequences and create primer dimers. A "closed annealing temperature" is typically at or below 60° C., at or below 59° C., at or below 58° C., at or below 57° C., at or below 56° C., at or below 56° C., or at or below 55.

As used herein, an "open annealing temperature" refers to a temperature at or above which a given hairpin barcode primer, or plurality of hairpin barcode primers, or extended products thereof used in a given PCR mixture, can both anneal to a target nucleic acid and maintain the hairpin barcode primer, or plurality of hairpin barcode primers, or extended products thereof, in the open configuration. In other words, temperatures at which the given hairpin barcode primer, or plurality of hairpin barcode primers do not comprise a stem and loop structure and the primer is in an extended or open configuration. An "open annealing temperature" is typically at least or above 65° C., at least or above 66° C., at least or above 67° C., at least or above 68° C., at least or above 69° C., or at least or above 70° C.

The "extension" step of a PCR cycle refers to the step where the polymerase activity of a polymerase adds nucleotides to the 3'-OH of an annealed primer, thereby generating a strand complementary to the template nucleic acid. The extension temperature is chosen to be close to the optimal temperature of the polymerase being used, but is also chosen to be one at which the primers are prevented from dissociating. For example, 72° C. is close to the optimal temperature for Taq DNA polymerase (~75° C.), but is a low enough temperature to prevent annealed primers from dissociating from the nucleic acid template. Indeed, when Taq DNA polymerase is used, primer extension typically can begin during annealing, because Taq DNA polymerase is partially active at 55° C. and even lower temperatures (Gelfand, 1989). The duration of the extension step depends mainly on the length of the sequence to be amplified. Typically, a duration of 1 min per kb of target nucleic acid product length is sufficient. In some embodiments, a series of PCR cycles can end with a final and separate extension step that is longer, for example, 5-10 minutes to ensure completion of target nucleic acid product synthesis.

As used herein, "PCR pre-amplification" refers to the cycles of PCR where the annealing temperature of the annealing step of a PCR cycle is less than or equal to the closed annealing temperature of the hairpin barcode primer, and generates a plurality of pre-amplification target nucleic acids. Typically, PCR pre-amplification comprises at least one cycle, at least two cycles, at least three cycles, at least four cycles, at least five cycles, at least six cycles, at least seven cycles, at least eight cycles, at least nine cycles, and no more than ten cycles where the annealing step of a PCR cycle is less than or equal to the closed annealing temperature of the hairpin barcode primer. In some embodiments of the methods described herein, PCR pre-amplification comprises 1-5, or 2-5 cycles.

Unless otherwise specified or qualified, in the methods described herein "PCR amplification" refers to the cycles of PCR following the PCR pre-amplification where the annealing temperature of the annealing step of at least some of the PCR cycles is greater than or equal to the open annealing temperature of the hairpin barcode primer, or plurality thereof, or extended products thereof, and generates a plurality of target nucleic acid amplicons. Typically, PCR amplification comprises at least 10 cycles, at least 15 cycles, at least 20 cycles, at least 25 cycles, at least 30 cycles, at least 35 cycles, or more cycles where the annealing step of at least three of the PCR cycles is greater than or equal to the open annealing temperature of the hairpin barcode primer. For example, a gradient PCR amplification can be used for some cycles where the temperature is slowly reduced from 80-72 degrees so that the stem remains open and adapter primers can bind before the stem closes, if the stem melting temperature is 74° C. In some embodiments, the extension step of a PCR cycle can comprise a temperature of 72° C. for several minutes followed by a second extension hold at 76° C. for 30 seconds. This can be used to improve complete extension from the reverse primer in cases where the stem reannealed at 72° C., for example.

In some embodiments of the methods described herein, if each of the hairpin barcode primers used in the pre-amplification PCR cycles, or subsets thereof, comprise a common adaptor sequence, then the PCR amplification cycles can be accomplished using universal forward and reverse adaptor-specific primers complementary to the adaptor sequence of the hairpin barcode primer(s) used in the pre-amplification PCR.

In some embodiments of the aspects described herein, the pre-amplification PCR cycles and the PCR amplification cycles are performed in the same reaction tube or vessel. In some embodiments of the aspects described herein, an aliquot of the reaction mixture generated from the pre-amplification PCR cycles is used in the PCR amplification cycles. In some embodiments of the aspects described herein, a clean-up step and/or a step of adding an enzymatic protease occurs between pre-amplification PCR with the hairpin barcode primers and subsequent PCR amplification.

An exemplary, non-limiting example of a pre-amplification PCR and the subsequent PCR amplification and typical reaction parameters used with the methods described herein follows. A 5-50 ul PCR reaction is set up with a final concentration of each hairpin barcode primers and reverse PCR primer of 40 nM, using a regular high fidelity PCR mastermix, such as AccuPrime SuperMix I (400 uM dNTPS, 40 mM Tris-HCL (pH8.4), 100 mM KCl, 3 mM MgCl$_2$, AccuPrime Taq DNA Polymerase, thermostable AccuPrime protein, and stabilizers). Pre-amplification PCR is performed using the following cycling conditions: 3 min of preincubations at 95° C. followed by 2-5 cycles of (95° C. 10 sec, 60° C. 4 min, 72° C. 30 sec). After PCR, the reaction is held at 60-65° C. for 15 min, while the tubes are opened and 20-250 ul of 1×TE buffer containing 0.2 ug/ul (final concentration) of heat-sensitive protease (*Streptomyces griseus*) is added to effectively kill the reaction. Finally the protease is inactivated at 80° C. for 15 min and cooled down to 4° C. until the PCR amplification step. The dilution at 60° C. is optimal and can be performed on ice with TE buffer alone, depending on starting DNA concentration and number of PCR cycles.

Adapter PCR or amplification PCR is next performed directly using an aliquot of the hairpin barcode primer pre-amplification PCR reaction mixture. The amplification PCR reaction is set up in a 20-100 ul volume containing 400 nM adapter primers using a regular high fidelity PCR mastermix, like AccuPrime SuperMix I (400 uM dNTPS, 40 mM Tris-HCL (pH8.4), 100 mM KCl, 3 mM MgCl2, AccuPrime Taq DNA Polymerase, thermostable AccuPrime protein, and stabilizers). Amplification PCR is performed using the following cycling conditions: 3 min of preincubation at 95° C. followed by 25 cycles of (95° C. 10 sec, 65° C. 5 sec, 72° C. 30 sec). Excess primers and small, non-specific PCR products are then removed using standard approaches and quantified prior to sequencing on, for example, Illumina sequencers.

In some embodiments of these aspects and all such aspects described herein, labels or tags can be used to further aid in the detection and discrimination of the target nucleic acid amplicons generated using the methods described herein. Thus, in such embodiments, label-specific detection methods can also be used to identify target nucleic acid amplicons that correspond to specific target nucleic acid sequences, in addition to the barcode sequence. Typically, a fluorescent molecule or dye is used as a label. Examples of fluorescence labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein and derivatives, such as 5-bromomethyl fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine 6G, Rhodamine Green, Rhodamine Red, Rhodol Green, 2',4', 5',7'-Tetra-bromosulfone-fluorescein, Tetramethyl-rhodamine (TMR), Carboxytetramethylrhodamine (TAMRA), Texas Red, Texas Red-X, LuciferYellow, IAEDANS, 7-Me$_2$N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethyl-ammoniobiman. Other examples of fluorescent dyes for use as detectable labels in the methods described herein, can be found at, among other places, U.S. Pat. Nos. 5,750, 409; 5,366,860; 5,231,191; 5,840,999; 5,847,162; 4,439, 356; 4,481,136; 5,188,934; 5,654,442; 5,840,999; 5,750, 409; 5,066,580; 5,750,409; 5,366,860; 5,231,191; 5,840, 999; 5,847,162; 5,486,616; 5,569,587; 5,569,766; 5,627, 027; 5,321,130; 5,410,030; 5,436,134; 5,534,416; 5,582, 977; 5,658,751; 5,656,449; 5,863,753; PCT Publications WO 97/36960; 99/27020; 99/16832; European Patent EP 0 050 684; Sauer et al, 1995, J. Fluorescence 5: 247-261; Lee et al., 1992, Nucl. Acids Res. 20: 2471-2483; and Tu et al., 1998, Nucl. Acids Res. 26: 2797-2802, the contents of each of which are herein incorporated in their entireties by reference.

In addition, base-linked fluorophores and quenchers are well-known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). In some cases, base-linked fluorophores are incorporated into primers by post-synthesis modification of oligonucleotides that were synthesized with reactive groups linked to bases. The fluorophores can be attached, for example, to the 3' OH of the sugar or the base.

The literature includes references providing exhaustive lists of fluorescent and chromogenic molecules and their relevant optical properties (see, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, Ed., Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949). Further, the literature provides ample guidance for derivatizing label molecules for covalent attachment via common reactive groups that can be added to an oligonucleotide (see, e.g., Haugland (supra); U.S. Pat. Nos. 3,996,345; and 4,351,760).

Methods for detecting and quantifying the amplified PCR products are well known in the art and any of them can be used in the methods described herein. Examples of such methods and systems include real-time PCR with detection of amplified nucleic acid with fluorescent dyes binding to double stranded DNA, such as SYBR Green or ethidium bromide, Real-time PCR with molecular beacons (detecting binding of fluorescently labeled probes to adjacent sequence in amplified PCR products), Real-Time PCR using a 5'-nuclease assay with Taqman probes (Applied BioSystems, Foster City, Calif.), involving Real-Time PCR thermocyclers such as the Lightcycler system from Roche (Indianapolis, Ind.), Applied Biosystems 7900HT, 7300, 7500 Real-time PCR systems (Foster City, Calif.), 1-cycler from Bio-rad (Hercules, Calif.), Rotorgene Real-time PCR cycler from Corbett (Sydney, Australia) and others.

Amplified PCR products or target nucleic acid amplicons can also be separated and quantified by capillary electrophoresis as described below.

Electrophoretic Separation Methods

Detection or verification of the target nucleic acid amplicons comprising adaptor and barcode sequences, can be accomplished by a variety of methods.

In some embodiments of the aspects described herein, the reaction products, including target nucleic acid amplicons comprising adaptor and barcode sequences, are subjected to size analysis methods. Size separation of nucleic acids is well known, e.g., by agars or polyacrylamide electrophoresis or by column chromatography, including HPLC separation. Methods for separating and detecting the presence or amount of polynucleotides are well known in the art and any of them can be used in the methods described herein so long as they are capable of separating individual polynucleotides by at least the difference in length between the various target nucleic acid amplicons comprising adaptor and barcode sequences. It is preferred that the separation and detection permits detection of length differences as small as one nucleotide. It is further preferred that the separation and detection can be done in a high-throughput format that permits real time or contemporaneous determination of surrogate marker amplicons' abundance in a plurality of reaction aliquots taken during the cycling reaction. Useful methods for the separation and analysis of the amplified products include, but are not limited to, electrophoresis (e.g., capillary electrophoresis (CE)), chromatography (dHPLC), and mass spectrometry. A preferred approach for the aspects described herein uses capillary electrophoresis, which is both rapid and accurate, and readily achieves separation of molecules differing in size by as little as one nucleotide. Capillary electrophoresis uses small amounts of sample and is well-adapted for detection of nucleic acids by, for example, fluorescence.

Nucleic acid fragments, such as DNA fragments, have traditionally been separated and analyzed by electrophoretic methods, such as slab gel electrophoresis. Such electrophoretic techniques separate nucleic acid species based upon their size and ionic properties. In the case of slab gel electrophoretic methods, voltage applied at the ends of a gel, such as an agarose gel, generates an electric field with a strength defined by the length of the gel and the potential difference at the ends (V/cm). Nucleic acid molecules exposed to this electric field migrate toward the anode due to the negatively charged phosphates along the nucleic acid backbone. The migration velocity is limited by the frictional force imposed by the gel matrix. While charge and/or size can affect the rate at which macromolecules will pass through a gel, the charge to mass ratio is the same for DNA molecules of different lengths. It is generally the size of the DNA, therefore, that determines the rate at which it passes through the gel, thereby allowing an effective separation of DNA fragment-length mixtures by electrophoresis. It is noted that fluorescent labels can have effects on nucleic acid migration, but the influence of the label generally diminishes with increasing fragment size, particularly where labeled primers are used. Gel matrices are usually either polyacrylamide or agarose, and separations can be achieved in the presence (e.g., for ssDNA) or the absence (e.g., for dsDNA) of dissociating agents, such as urea or formamide. Such slab gel systems can analyze multiple samples in the same separation (i.e., gel(s)) at low cost, but normally take several hours to complete. The nucleic acid fragments or DNA are typically visualized with stains, UV shadowing, intercalating dyes, such as ethidium bromide, incorporated fluorescent labels, and sometimes radioactive labels.

Capillary electrophoresis (CE) is a very powerful electrophoretic method for the separation of nucleic acid fragments. CE can be performed by methods well known in the art, for example, as disclosed in U.S. Pat. Nos. 6,217,731; 6,001,230; and 5,963,456, the contents of each of which are herein incorporated in their entireties by reference. CE offers a number of advantages over slab gel separations in terms of speed, resolution, sensitivity, and data handling. This is, in part, because the CE separation occurs inside a small-diameter (50- to 100-µm) quartz capillary in the presence of high (kilovolt-level) separating voltages. Separation times are generally only a few minutes. The nucleic acid fragments can be detected, for example, by UV absorption or by fluorescent labeling, both of which eliminate the need to use mutagenic substances (e.g., ethidium bromide) or dispose of radioactive waste. The quantity of DNA required for the separation is in the nanogram range. Single-base resolution can be readily obtained on fragments up to several hundred base pairs in size. In the presence of appropriate standards, fragments can be accurately sized, based on relative electrophoretic mobility. Multicapillary automated instruments using laser fluorescence detection systems based on CE have also been developed, and are commercially available.

The separation of nucleic acid fragments by CE occurs within the walls of a capillary, such as a fused-silica capillary. Since the negatively charged nature of this surface has a dramatic impact on the resolution achieved during the separations, the vast majority of CE separations are done in "coated" capillaries whose surface has been modified to be chemically inert to nucleic acids. The capillaries are filled with a sieving matrix, and nucleic acid fragments are separated on the basis of size, analogously to slab gel separations. The sieving matrix can be a chemically cross-linked gel (static gel), such as polyacrylamide, or a flowable (non-cross-linked) polymer, such as modified cellulose or non-cross-linked polyacrylamide. Single-stranded DNA (ssDNA) fragments as small as 5 bases can be readily separated with single-base resolution. Fragments of double-stranded DNA (dsDNA) as large as 20 kb are also separated, although not with single-base-pair resolution.

The selection of the appropriate matrix can significantly affect the quality of the separation. The general rule for matrix selection is that the larger the DNA fragment, the weaker the sieving capabilities of the matrix should be. With either a cross-linked or non-cross-linked gel in the capillary, the matrix offers a frictional resistance to the movement of the DNA through the gel medium that is proportional to the size of the species. The frictional resistance can vary with the molecular weight, concentration, and chemical composition of the flowable gel polymer or the pore size in the cross-linked gel, and should be optimized for the particular size of the DNA to be separated. A detailed description of the theory of DNA motility in entangled polymer solutions can be found in Grossman (Grossman P. D. and Colburn J. C. (1992) Capillary Electrophoresis: Theory and Practice, 1sted., Academic Press, San Diego).

Cross-linked polyacrylamide is best used for the separation of synthetic oligonucleotides—both native and modified versions. However, flowable polymers can also be used for oligonucleotide analysis and for the separations of automated sequencing ladders. Where double-stranded DNA fragment analysis is required, flowable polymers are routinely used.

As used herein, "cross-linked gels" refer to fixed gels, such as polyacrylamide gel, that are polymerized inside the capillary, usually covalently bound to the capillary surface, and are not removed from the capillary between runs. Such cross-linked gels can be reused for 30 to 100 separations before losing resolution. The capillary is then discarded, since the polyacrylamide gel cannot be regenerated.

Flowable polymers have the advantage of wide fragment-separation ranges. A "flowable polymer" or "flowable polymer matrix" refers to viscous hydrophilic polymer solutions that can be pumped into a capillary, such as, but not limited to, hydroxypropyl methyl cellulose (HPMC), hydroxyethylcellulose (HEC), polyethylene oxide (PEO), or non-cross-linked linear polyacrylamide. In some embodiments, the same flowable polymer matrix can be used repeatedly when small molecules, such as synthetic oligonucleotides are being analyzed. Alternatively, the polymer can be used once, discarded, and replaced with fresh matrix prior to the next sample. This latter embodiment is preferred where larger DNA molecules are present in the samples—e.g., for fragment analysis and DNA sequencing analysis. A flowable polymer can be expelled from the capillary by pressure at the end of each electrophoretic separation; fresh matrix is then reloaded into the capillary prior to the next separation.

As noted previously, a coated capillary is usually utilized to eliminate the charge effects that are contributed by the native silica surface. With cellulose-derived polymers or some specially modified acrylamides, however, uncoated capillaries may be used, because of the strong interaction of the polymer with the inner surface of the bare fused-silica capillary, in essence forming its own coating.

Separation buffers for use in capillary electrophoretic methods are frequently variants of Tris/borate/EDTA (TBE) mixtures and are buffered at alkaline pH. Urea (e.g., 6 to 8 M) is often included in the buffer, as a denaturant, that keeps the DNA in single-stranded conformation when required, such as when analyzing ssDNA (e.g., synthetic oligonucleotides). Urea can be omitted from the buffer for analyses where secondary structure plays an important role in the separation, e.g., single-nucleotide polymorphisms or conformational polymorphisms. Samples are loaded onto the capillary by electrokinetic, or pressure, injection. Separation times range from 10 to 45 min, at voltages between 1 and 10 kV.

CE separation in its simplest form can be achieved by passing a high voltage between two buffer reservoirs that are joined by a fused silica capillary filled with liquid or gel. This results in an electric field that drives the nucleic acid molecules of interest from one end of the capillary to the other. The capillaries are preferably 20 to 80 cm long and 50 to 100 µm in internal diameter, with total volumes in the 1- to 2-ul range. The combination of high field strength and large surface-area-to-volume ratio of the capillaries results in rapid and very efficient separations of, for example, both ssDNA and dsDNA. Sample loading can be accomplished from as little as 1 with starting sample concentrations of ~1 µg/ml for UV detection and ~1 µg/ml or less for laser-induced fluorescence detection. The capillaries are preferably thin walled, which allows for dissipation of the Joule heating resulting from the high voltages (10 to 30 kV) that are necessary for high-performance electrophoretic separations. The fused-silica capillary can be coated on the outside with a polyimide layer that eliminates oxidation of the fused-silica glass and confers tensile strength to the capillary. The polyimide sheathing can be carefully removed from a small portion of the capillary to expose a section of the silica. This clear section of the capillary can be inserted into the light path of a UV or fluorescence detector, and becomes an "on-column flow cell." As the nucleic acid molecules migrate through the capillary as a result of the electric field, they pass through the detector light path and are measured by UV or fluorescence detection.

In preferred embodiments of the aspects described herein, a CE instrument for use with the methods of detecting nucleic acid molecules comprises a suitable sample injection module and a detector module, and can further comprise additional modules, such as temperature control modules, etc.

High-throughput CE apparatuses are available commercially, for example, the SCE 9610 fully automated 96-capillary electrophoresis genetic analysis system from P/ACE 5000 series and CEQ series from Beckman Instruments Inc (Fullerton, Calif.); and ABI PRISM 3100, 3130 and 3730 genetic analyzers (Applied Biosystems, Foster City, Calif.), among others. In some embodiments, the high-throughput CE apparatus and related quantitative methods used with the methods described herein are based on the methods and apparatuses described in "Scalable Transcriptional Analysis Routine Multiplexed Q_PCR Platform for Gene Expression Analysis and Molecular Diagnostics." J Mol Diag 7 44 (2005), and/or as described in U.S. Pat. Nos. 7,550,266; 7,445,893; 7,674,582; 7,081,339; 7,368,246; and in US 20040014117, the contents of each of which are herein incorporated in their entireties by reference. Near the end of the CE column, in these devices the nucleic acid fragments pass a fluorescence detector which measures signals of fluorescent labels. Accordingly, these apparatuses provide automated high-throughput for the detection of surrogate markers or surrogate marker amplicons of different sizes, as described herein.

Next Generation Sequencing Methods

"Next-generation sequencing" (NGS) techniques can benefit from the methods described herein, which allow amplification of target nucleic acid sequences and labeling with unique barcodes, with minimal primer dimer formation. NGS methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing, template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1 \times 10^6$ sequence reads can be achieved, resulting in up to 500 million base pairs (Mb) of sequence.

In the Solexa/Illumina platform (e.g., MiSeq sequencing platform), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Other exemplary next-generation sequencing systems include the Ion Torrent PGM sequencer (Life Technologies) and the Ion Torrent Proton Sequencer (Life Technologies), which are ion-based sequencing systems that sequence nucleic acid templates by detecting ions produced as a byproduct of nucleotide incorporation. Typically, hydrogen ions are released as byproducts of nucleotide incorporations occurring during template-dependent nucleic acid synthesis by a polymerase. The Ion Torrent PGM sequencer and Ion Proton Sequencer detect the nucleotide incorporations by detecting the hydrogen ion byproducts of the nucleotide incorporations.

The data obtained from the sequencing procedure, can be analyzed in a variety of manners for identification of specific amplicons present in the sample as well as identification of the number or contributors in a mixed sample. The sequencing data can also be used to identify chromosomal abnormalities in fetal genetic screening applications and analysis of biological cells (e.g., tumor cells) for characterization and treatment.

Multiplex

The methods described herein are particularly adapted to provide analysis of two or more species (i.e., a plurality, e.g., 2, 3, 4, 5, 6, 7, 9, 9, 10, 15, 20, 25, 30, 40, 50, 75, 100, 250, 1000, or more) of target nucleic acids from a single sample by using combinations of hairpin barcode primers and adaptor-specific primers for each of a plurality of target nucleic acid sequences of interest.

Kits

Also provided herein are kits for the amplification and detection of target nucleic acids using the methods described herein. A kit, as described herein, provides at least one hairpin barcode primer, a reverse primer, and an adaptor-specific primer pair, or any combination thereof. A kit can include any assemblage of components that are necessary or facilitate any method described herein. The components of the kits are not particularly limited or restricted. Kits can also include other primers necessary for any of the methods described herein, for example, one or more reverse-transcription primers, amplification primer pairs, or combinations thereof. Kits for use with the methods described herein can optionally contain written instructions describing how to use the kit and/or conduct the methods provided herein. Kits can also provide enzymes necessary for the methods described herein, e.g., reverse trancriptase, and/or DNA polymerases. In some embodiments, the DNA polymerases are thermostable polymerases.

EXAMPLES

Example 1

Even with next-generation sequencing, detection of very rare mutations in clinical samples is challenging due to background noise from sequencing errors. Approaches to overcome sequencing errors have been described but still have significant limitations. The methods described herein provide new approaches that facilitate detection of very rare mutations in clinical samples when used in combination with next-generation sequencing.

Next-generation sequencing (NGS) is now widely used in cancer research and is also an important clinical tool. Using targeted libraries, NGS can interrogate specific genome regions at extremely high depth and therefore identify rare mutations even in relatively heterogeneous clinical samples, such as cytology samples or bodily fluids. However, mutant detection levels are still limited by the error rate inherent in current NGS protocols, such that reliable detection of mutant fractions below 1-2% remains challenging. While this is adequate for many applications, there are a number of avenues of cancer research that require even more sensitive approaches. Perhaps the best example of this is the detection of mutations in bodily fluids such as plasma, urine, sputum and others where DNA from a few cancer cells is present in a vast excess of normal cell DNA. Applications such as cancer diagnosis, monitoring response to therapy and monitoring the evolution of tumor heterogeneity via liquid biopsy (plasma) all require detection of mutations at frequencies below 0.1%.

Recently developed experimental methods combined with new algorithms for variant calling are capable of achieving this sensitivity but require large amounts of relatively good quality DNA, or can only analyze very limited genomic regions (single PCR amplicons). When dealing with plasma as an example, typical DNA yields are only 5-10 ng/ml of plasma and the DNA is highly fragmented. In this setting, one typically wishes to interrogate several kilobases of target sequence from different mutation hotspot regions across the genome. Prior to the methods described herein, there was no easy way to do this with a mutation detection sensitivity of under 0.1%.

The ability of massively-parallel, next-generation DNA sequencing (NGS) to identify low prevalence mutations in heterogeneous samples has revolutionized basic and translational research in cancer and many other fields. NGS is also rapidly becoming an important platform for identifying mutations and variants in clinical samples. In many cases these samples contain admixtures of DNA from different sources, such as cancer cells, virus particles and bacteria, with normal host cell DNA. Examples include detection of heteroplasmic mutations in mitochondrial DNA genomes, detection of fetal DNA alterations in maternal plasma, detection of drug resistance mutations in viral diseases, such as AIDS and hepatitis, and detection of donor DNA in the blood of transplant patients as an indication of organ rejection. In cancer, applications of rare mutation detection include analysis of tumor heterogeneity and identification of therapy resistant clones, detection of residual disease in surgical margins or lymph nodes, detection of disease in biopsies, aspirates and cytology samples and early cancer diagnosis using blood, sputum, urine, stool or other bodily fluids.

Our group is actively working in these areas with studies to detect esophageal cancer using mutation detection in cytology samples collected using a "sponge on a string" device called EsophaCap (http://capnostics.com/home.html) and another to evaluate the detection of circulating, cell free DNA in plasma as a method for early detection and monitoring of patients with esophageal cancer. We anticipate that both studies will require detection of mutations at <0.1% mutant allele fraction. This is readily achievable using technologies such as digital PCR (e.g., RainDrop digital PCR; see for example on the worldwide web at raindancetech.com/digital-per-tech/raindropdigital-per-system/) but digital PCR interrogates mutations using assays that are highly specific not only to base location but also the specific base change.

For cancer diagnosis, or for monitoring clonal evolution of tumors in response to therapy using liquid biopsies, we need the ability to interrogate several kilobases of DNA for very rare mutations that may occur at any base within the target sequences. Furthermore, we need the ability to do this starting with relatively small amounts of DNA available from these sample types. A tool with this capability would find numerous applications in clinical cancer research and diagnostics. Rare mutation detection with NGS requires very high read depths (for example, a 0.1% mutant would give only one mutant read with a relatively high read depth of 1000×) and this rapidly becomes expensive, even though sequencing costs continue to fall. However, this is not the main issue. The major challenge for rare mutation detection with NGS is distinguishing a true mutant signal from background error or noise. Errors in NGS originate from base misincorporations introduced during library preparation and solid-phase amplification on the sequencer, base misincorporation during sequencing, and base calling errors during detection/image analysis. Depending on the library preparation method, sequencing platform and variant calling algorithm, error rates of 0.05-3% are typically reported depending on the specific mutation type. For single base point mutations, which are the most common mutations in cancer, error rates are typically on the higher side at ~1-3%.

Recently, there have been several reports of experimental and/or computational approaches to improve rare mutation detection with NGS, but none address all of the requirements discussed above. In addition, most if not all of the reported approaches still require extremely high read depths and are therefore expensive.

Described herein are methods for NGS library construction and data analysis that permit highly sensitive mutation detection in several kilobases of target sequence when starting with as little as 10-50 ng of DNA. These methods are based, in part, on incorporation of unique barcode ID's (UID's) into target molecules in a PCR pre-amplification step. While similar approaches has been previously described for single PCR amplicons, they cannot currently be performed with high level multiplexing. We address this limitation, in part, through innovative new approaches to library construction, which aim to achieve <0.05% mutation detection in a >100-plex reaction covering ~2.5 Kb of DNA.

Also provided herein are agnostic mutation enrichment approaches that can be used to enhance rare mutation detection in NGS, while reducing sequencing read depth requirements and cost. These approaches are based, in part, on formation of heteroduplexes between wild type and mutated DNA strands followed by heteroduplex recognition and binding by the MutS protein component of DNA repair to facilitate pull down of the captured heteroduplexes using magnetic beads. Enrichment can be tested in pre and post-PCR steps of library construction using both standard library construction approaches and also using the approaches described herein.

Detection of rare mutations by NGS in biopsies, cytology samples and in body fluids is becoming more and more important in both research and clinical settings. However, DNA yield from these sample types is often low and DNA can be fragmented, making library construction more challenging. Several approaches have been described to achieve rare mutation detection. These include purely computational methods, modifications to sequencing library construction or combinations of both. For example, Li et al. described a computational approach using large sets of population re-sequencing data to estimate the sequencing error profile and thereby generate a reliability score for mutation calling at each base within a target sequence. However, the ability to detect rare mutations was still limited and the authors noted the need for improved experimental protocols in addition to computational advances.

Most NGS experimental approaches reported thus far rely on addition of unique ID's (UID's), often referred to as barcodes or indexes, on to the target DNA molecules. By barcoding each individual target DNA strand with a UID (typically a random oligonucleotide sequence of variable length), all sequence reads originating from one target strand can be grouped into "super-families" based on the UID. If the original target contained a mutation, all reads in the super-family will also contain that mutation. Occasional sequencing errors will occur in reads in super-families from wild type targets (and at other bases within a mutant super-family) but can be discounted because they are not represented in the majority of reads. This approach is therefore able to distinguish and eliminate most sources of sequencing errors, with the exception of PCR induced errors that occur in the very first PCR cycle. This is mitigated by the use of high-fidelity polymerases and the requirement to see the same mutant in more than one super-family. Using this strategy alone or in combination with additional computational modifications, mutation detection rates of <0.1% are readily achievable.

However, there are important limitations with the published approaches. For example, most are based on ligation of barcoded adapters and while this allows for target selection and generation of complex sequencing libraries it requires relatively large amounts of DNA (~500 ng and 3 μg in the published reports). An alternative approach (termed Safe-Sequencing System or Safe-SeqS) incorporates UID's using a small number of initial PCR cycles with primers that include the UID sequence plus an adapter sequence for subsequent amplification. This is a very efficient way of incorporating the UID's, and can be performed with small amounts of fragmented DNA, but it has thus far only been reported with single amplicons, and multiplexing multiple amplicons remains a challenge. Furthermore, the Safe-SeqS (SS) protocol requires polyacrylamide gel purification of the PCR product prior to sequencing; a less than ideal situation in a clinical testing environment.

Described herein are methods and approaches to address the current limitations in rare mutation detection from sub-optimal samples. Provided herein, in some aspects, are multiplex PCR-based approaches for UID incorporation that can target several kilobases of DNA with a simple workflow amenable to clinical testing. These methods use stem-loop or hairpin primers designed to "hide" the degenerate UID sequence during the first few PCR cycles, thus greatly reducing non-specific product formation. In addition, the UID labeling step is performed in a picoliter digital PCR format to further reduce non-specific PCR priming.

As described herein, we have determined that the major hurdle to multiplexing the SS approach is that relatively long, non-specific PCR products are formed during the initial PCR cycles and that these products out-compete the desired, specific products during the second round of PCR. These products are primer concatamers, typically referred to as primer dimers. In the case of SS, these products are longer than in a typical PCR simply because the SS primers themselves are required to be long (52 70 bp). The increased length of the primer dimers is problematic as it becomes hard to separate them from the desired PCR products using standard, bead-based library clean-up methods (again leading to the need for PAGE gel purification in the Furthermore, we determined that the high abundance of these products is due to the presence of the random 14mers that make up the UID. This essentially makes for a very complex pool of primers and increases the likelihood of mis-priming and nonspecific products.

In some embodiments of the methods described herein, to help minimize non-specific product formation, the primer concentration to a level (50 nM) more compatible with highly multiplexed, pre-amplification strategies developed for working on single cells and low DNA inputs. This approach has the added benefit of avoiding the need for exonuclease removal of unused primers prior to the second round of PCR, as in the original SS method. With this change, we were able to demonstrate efficient formation of the desired, specific products starting with a 13-plex reaction, although non-specific products still dominated.

Figure 2:
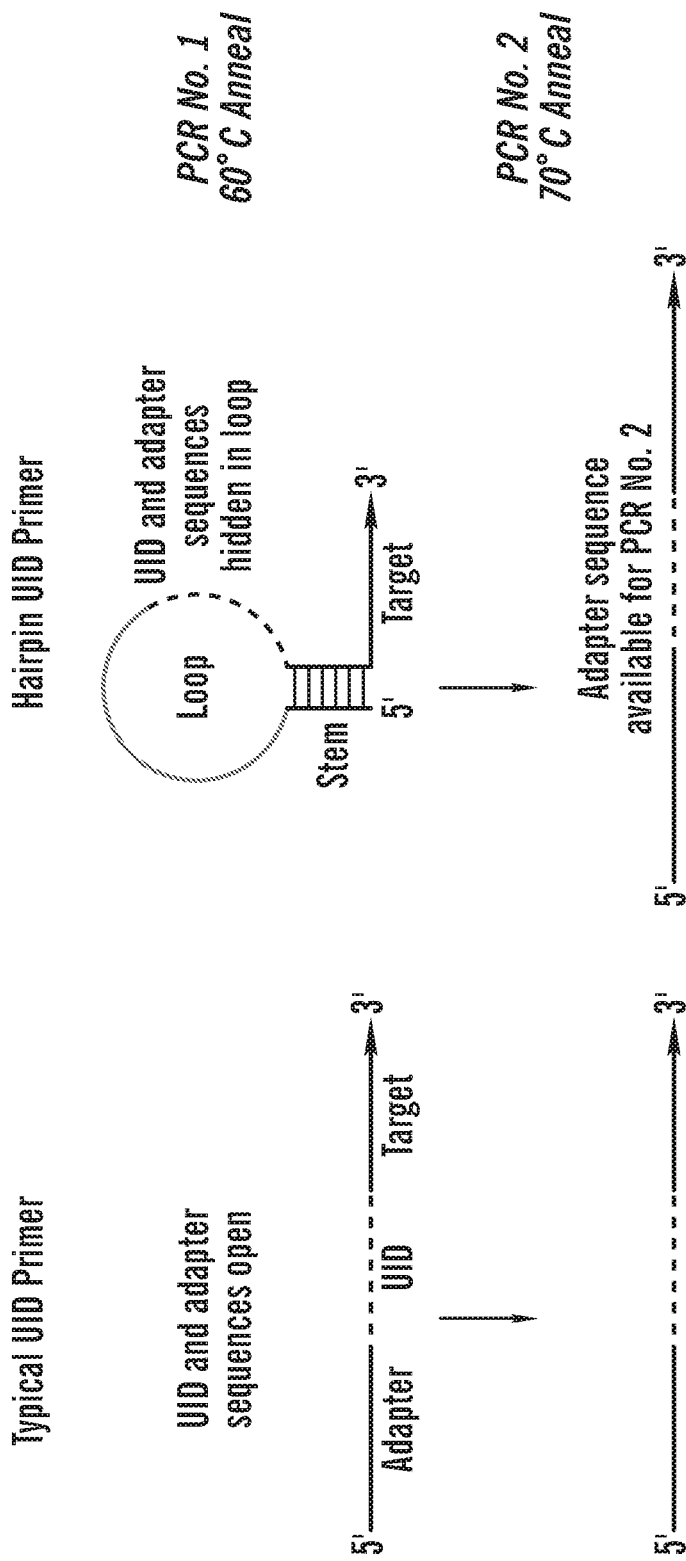
FIG. 2 demonstrates concept of stem-loop (hairpin) priming to "hide" the N14 UID in the SS primer, thus reducing mis-priming events. Hairpin is closed at 60° for PCR No. 1 and open at 70° to allow efficient PCR with adapter primers in PCR No. 2.

Accordingly, as described herein, we conceived an approach designed to "hide" the majority of the adapter and UID sequences in the forward primer by creating primers with a stemloop (hairpin) structure designed to be closed at the anneal/extend temperature used in the first round of PCR but open in the second round of PCR (see, e.g., FIG. 1). We found that this approach greatly reduced the amount of non-specific PCR products generated, compared with standard UID primers while increasing the relative abundance of the desired PCR products (FIG. 2, $h_{14}$UID). Next, we decided to test a similar strategy on the reverse primer. Using the reverse hairpin primer with a standard UID forward primer (FIG. 2, $_{14}$UIDh) had little effect as we believe, without wishing to be bound or limited by theory, that it is the random 14-mer in the forward primer that causes problems. Similarly, when hairpins were included in both forward and reverse primers (FIG. 2, h$_{14}$UIDh), results were comparable with the forward hairpin only.

In some embodiments of the aspects described herein, additional strategies can be incorporated to increase the yield of desired products and minimize nonspecific products. For example, a multiplex of five PCR amplicons targeting known mutation hotspots in cancer-associated genes TP53, PI3KCA, KRAS and SMARCA4 can be used.

For example, the hairpins can be further modified for reducing non-specific PCR products by modifying the melting temperature of the stems, to ensure they are closed during the first round of a PCR cycle, i.e., melt at approximately 60-65° C., and open during the second round/phase of a PCR cycle, i.e., open at approximately 72° C. Such modification can be used to prevent/inhibit hairpin structures from persisting on the end of PCR products during the anneal/extend phase of the second PCR cycle, which can impact PCR efficiency.

Figure 3:
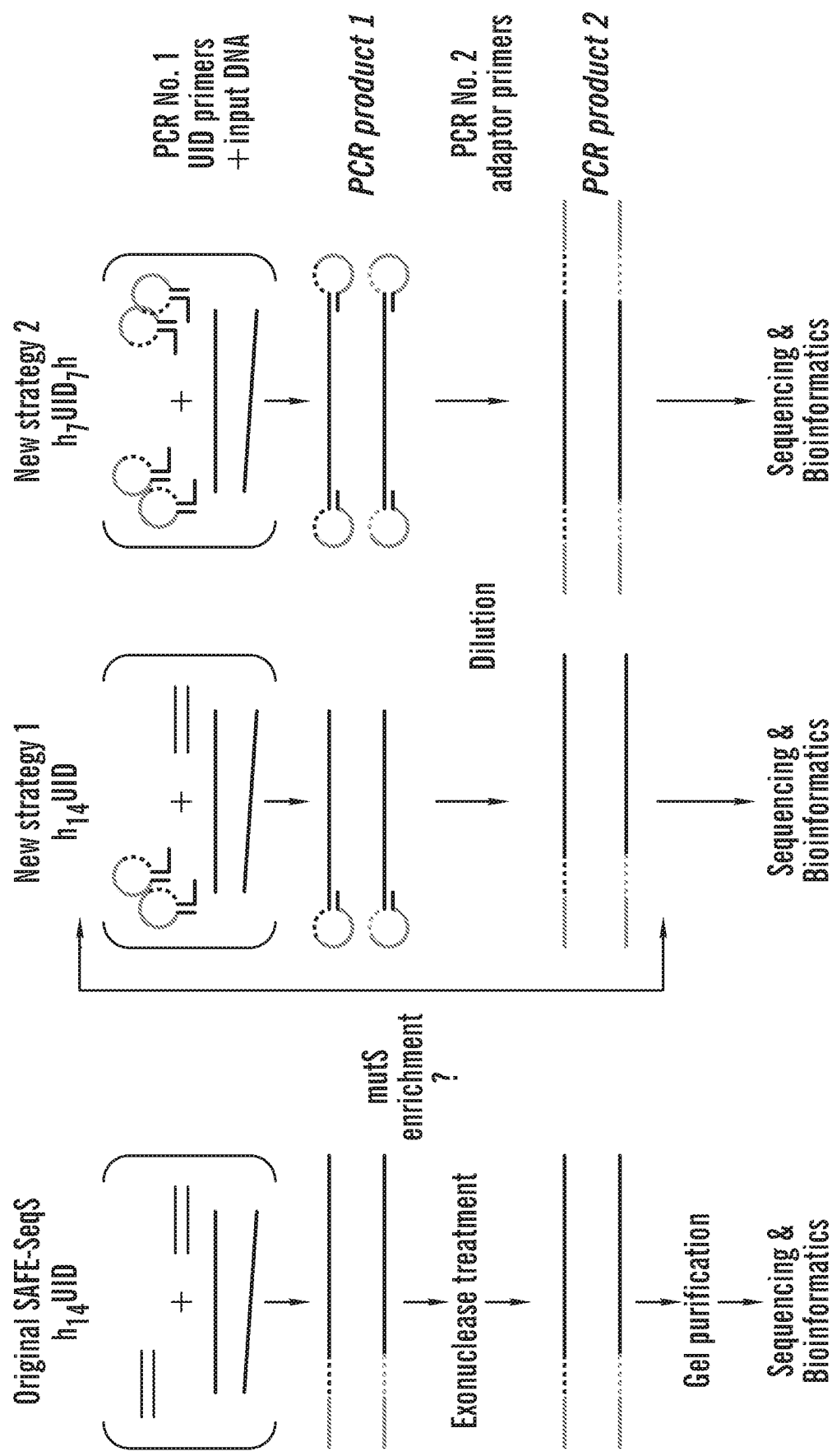
FIG. 3 depicts schematic representation of the three SS primer approaches to be tested. Blue=adapter primer sequences, dashed lines=UID sequences. UIDS are included in regular primers (original SS), forward hairpin primer only (strategy 1) or both forward and reverse hairpins (strategy 2). The adapter sequences double as Illumina sequencing primer sites and the Illumina flow-cell capture sequences are incorporated in the second PCR. Potential MutS enrichment opportunities are indicated. target (TFRC_DNA, TYE channel) were detected in a single reaction. Nucleic acids present in samples taken at stages during the PCR amplification were separated by capillary electrophoresis.

In some embodiments, different primer design approaches can be used (FIG. 3). For example, in some embodiments the entire UID is incorporated in the forward hairpin primer (h$_{14}$UID). In some embodiments, the UID can be split between the forward and reverse primers, both with hairpins (h$_7$UID$_7$h). Splitting the UID such that 7 random bases are included in both forward and reverse primers results in the same diversity of barcodes available for labeling of original target molecules ($4^{14}$ different UID's) but can have additional advantages. For example, even though the UID is in the loop structure of the hairpin primers, it is still possible that it is somewhat accessible for mis-priming, which can be minimized with only 7 random bases in each primer. This also makes it harder to generate mis-priming at the 60° C. anneal/extend temperature used in the first PCR cycle. Thus, in those embodiments where the UID is split between the forward and reverse primers, further reduction of non-specific product formation can be achieved.

To test the various embodiments of the methods described herein, for example, 3-5 cycles of first round PCR can be performed starting with 50 ng (approx. 15,000 haploid genome copies) of genomic DNA, diluting the products 2-10 fold (to maintain approximately two UID's per original target molecule and also eliminate the need for exonuclease treatment, and then performing 25 cycles of second round PCR with adapter primers. Formation of specific and non-specific products can be evaluated in a variety of ways. For example, gel electrophoresis can be used to visually examine products and fluorescently labeled adapter primers and capillary electrophoresis can be used if better quantification and size resolution are required. Quantitative real-time PCR can be used to quantify both total PCR product and yield of desired PCR product. Total product can be quantified by performing the second round PCR in real-time with SYBR green detection of products. Specific product yield can be determined by performing real-time PCR on a dilution of the second round PCR, but using internal primers specific to the desired targets. If necessary, hybridization probes can be utilized instead of SYBR green as a detection method for specific products. Finally, if it is determined that adequate specific product is being generated for a use described herein, sequencing of selected libraries can be performed on an Illumina MiSeq instrument. By mapping reads to the human genome and quantifying expected sequences (corresponding to amplicons) and unexpected sequences (consisting of off target priming events, primer dimers, and unmappable reads), a very precise estimate of the yield of specific versus non-specific products generated in each library can be made. Furthermore, these data provide information regarding representation of UID's when different numbers of UID PCR cycles are performed and aids in optimizing the methods for the applications described herein.

In some embodiments, another strategy to increase specific product yield is to perform a size-selection clean-up to remove non-specific product after the UID PCR, prior to the adapter primer PCR. While this is a standard technique in sequencing library construction, it is made more challenging using the methods described herein, due to the larger size of the non-specific products. A variety of clean-up approaches can be used, such as, for example, magnetic bead-based size selection using AGENCOURT AMPURE XP from BECKMAN COULTER and magnetic nanoparticle selection using MAGVIGEN products from NVIGEN inc. For the AMPURE approach, a range of bead dilutions can be evaluated to achieve the desired size cut-off, and for the MAGVIGEN approach, the >100 bp, >150 pb and >200 bp kits can be tested. Following clean-up, a second round of PCR can be performed using the adapter primers and the most effective clean-up approach can be determined by, for example, gel electrophoresis, quantitative PCR, and/or library sequencing on a MiSeq.

In some embodiments, another strategy to increase specific product yield is to evaluate the use of picoliter droplet PCR (dPCR) during library construction. Specifically, the RainDrop digital PCR system from Raindance Technologies can be utilized to dropletize the UID PCR step in a manner similar to that used in the ThunderBolts cancer panel being developed by Raindance (http://raindancetech.com/thunderbolts/).

In the droplet PCR workflow, the complete 25-50 µl PCR reaction mix is first converted into 5-10 million, 5 picoliter droplets, each now comprising an independent PCR reaction. dPCR is performed as usual following which the droplets are broken and the aqueous phase can be used directly for downstream applications. With input DNA amounts in the 50-100 ng range (15-30,000 copies of each target), >90% of the droplets contain no target DNA, while those that do contain DNA only have a single copy of one target on a fragment of DNA. Thus, the target complexity is greatly reduced in each droplet compared with the original PCR reaction mix and this reduces non-specific PCR product. This can be particularly helpful in the UID PCR cycles when formation of non-specific product is initiated. However, an additional advantage of dPCR is the lack of competition between different PCR amplicons, as each droplet only contains one target. This allows each PCR reaction to achieve maximal yield and could result in more uniform depth of sequence coverage if used in the second round of PCR with adapter primers. Therefore, inclusion of a dPCR step can be evaluated in both PCR rounds and outcome measures are the yield of specific versus non-specific product and uniformity of sequence depth across target amplicons.

Also provided herein are data analysis pipelines and methods thereof. Reads for individual samples are assigned to amplicons by the primer sequences contained at the sequence ends. Reads, or read-pairs, with primer pairs inconsistent with amplicon designs are discarded. After reads for each amplicon are identified, the UID contained in each read is extracted and used to group reads by UID. The reads within each group are used to generate a consensus sequence for each UID-amplicon comprising the most likely base at each position in the amplicon for a given UID. The initial mapping to amplicons allows the use of the same UID across multiple amplicons and reduces the chance of reads from multiple reference molecules of being grouped together.

After consensus reads are constructed, they are mapped to the genome and analyzed for variants using standard bioinformatics tools and pipelines (Novoalign/bwa for alignment; GATK/MuTect/Strelka for variant calling) with minor modifications. Appropriate settings for variant callers are identified as necessary to cope with the low allele frequencies detectable by the sequencing protocol being developed.

Also provided herein are methods for multiplex scale-up and validation of sensitive mutation detection in mixtures of tumor DNA with previously identified mutations to samples comprising, for example, >100 PCR amplicons. To increase success, and maximize value for research, the PCR targets and primers used are initially drawn from the ThunderBolts Cancer Panel developed by Raindance. The Cancer Panel is comprised of 230 amplicons, split into two pools, and targets mutation hotspots in 50 known oncogenes and tumor suppressor genes. By selecting one amplicon pool, primer sequences and amplicons that have been rigorously tested and validated to work well together in a multiplex are utilized. Primers can be modified to include UID hairpin approaches and then perform library construction using any know method known in the art, for example, clean-up, droplet PCR etc.

To identify desired libraries, the level of sequence depth and coverage across all amplicons can be measured, with uniformity being ideal. Specifically, libraries can be generated starting with 10-100 ng of normal genomic DNA and sequencing performed on the Illumina HiSeq instrument. Library quality can be assessed by comparing total number of mapped reads, average read depth across all amplicons and read depth of each individual amplicon relative to the average across all amplicons. Average read depth can be influenced by the level of sample multiplexing, obtaining 100% coverage of all amplicons at a minimum of 20% of the mean amplicon read depth is preferred. To ensure PCR performance, amplicons can be separated into pools of 10×10, 4×25 or 2×50 and UID PCR products combined prior to library construction.

The approaches described herein can be validated by mixing DNA from tumor samples so that the final DNA pools contain 10-12 unique mutations in the target amplicons at allele fractions ranging from 0.05-5%. For example, DNA from esophageal adenocarcinoma specimens can be used on which whole exome sequencing has been performed and mutations identified. Once pooled, mutation frequency can be verified by digital PCR on the RainDrop instrument and adjusted if necessary prior to library construction. Replicate analyses of 3-5 DNA pools can be run order to estimate the reliability with which mutations present at different allele frequencies can be detected.

The sequencing mode chosen can depend on the primer configuration selected. For example, if a 14mer barcode is utilized single and paired end sequencing can be used, but if two 7mer barcodes are used, paired end libraries can be used. Appropriate read lengths can be chosen based on the size of amplicons, the sequencing mode and the sequencing platform. Required sequencing read depth is determined by several factors and minimally should be: # amplicons×# target copies×# UIDs/target×required reads/UID. For example, if there are 5 amplicons, 15,000 target copies and ~2 UIDs/target, assuming that approximately 20 reads per UID is sufficient to determine the consensus sequence, each library requires ~3 million mapped reads. Therefore, the MiSeq instrument with 4 to 5 libraries per lane (12-15 million reads) can be used. For example, if there are 100 amplicons, the number of reads required is ~60 million and for this 3 to 4 libraries are multiplexed per lane of a HiSeq instrument (200-250 million reads).

Also provided herein are agnostic mutation enrichment methods that increase mutation detection sensitivity and also greatly reduce the sequencing read depths (and cost) required for rare mutation detection. These methods for agnostic mutation enrichment specifically identify and capture heteroduplex DNA fragments using the DNA repair protein MutS and magnetic beads. Incorporation of this enrichment into sequencing library construction impacts mutation detection sensitivity and sequencing cost across broad applications.

The approaches described herein are based, in part, on the ability of MutS protein, a component of the DNA repair system, to identify and bind to mismatches (heteroduplexes) in double stranded DNA fragments. This includes recognition of single base mismatches and small insertions/deletions up to ~3 bases. Heteroduplexes can be induced simply by denaturing a mixture of wild type (WT) and mutant (Mut) DNA fragments or PCR products and then allowing them to cool slowly to room temperature. Furthermore, heteroduplex formation is favored specifically under conditions when the mutant fraction is low. Similar approaches have been described previously for mutation detection using MutS binding followed by gel retardation analysis or DNAse protection assays to identify presence of mutations. This approach has also been used to remove Taq polymerase-induced errors from PCR products prior to downstream analysis. Herein, we describe methods that use MutS binding to identify and then capture DNA heteroduplexes from a pool of normal, homoduplex DNA fragments. When applied to next-generation sequencing libraries created using PCR (directly or following initial target capture) this enriches for mutations, thus increasing sensitivity while reducing the sequencing depth required to detect rare mutations.

We envision that this approach can be used either pre or post PCR steps in library construction (FIG. 3) and each has advantages and disadvantages. Used pre-PCR, errors induced by Taq polymerase are not as important, but efficient recovery is critical as the number of mutant target molecules can be very low. Used post-PCR, recovery is not a concern, but Taq-induced errors are enriched. A combination of the methods using UID's and UID superfamily analysis in addition to the methods comprising MutS enrichment can be used, in some aspects.

Figure 4:
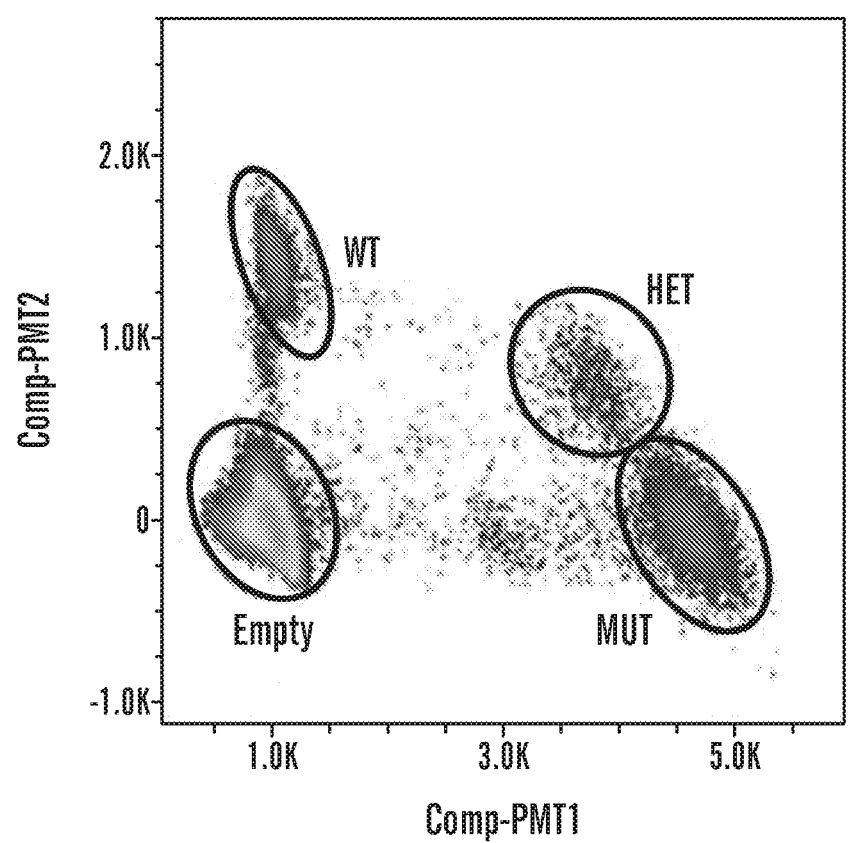
FIG. 4 depicts quantification of heteroduplex formation by picoliter digital PCR.
Figure 5:
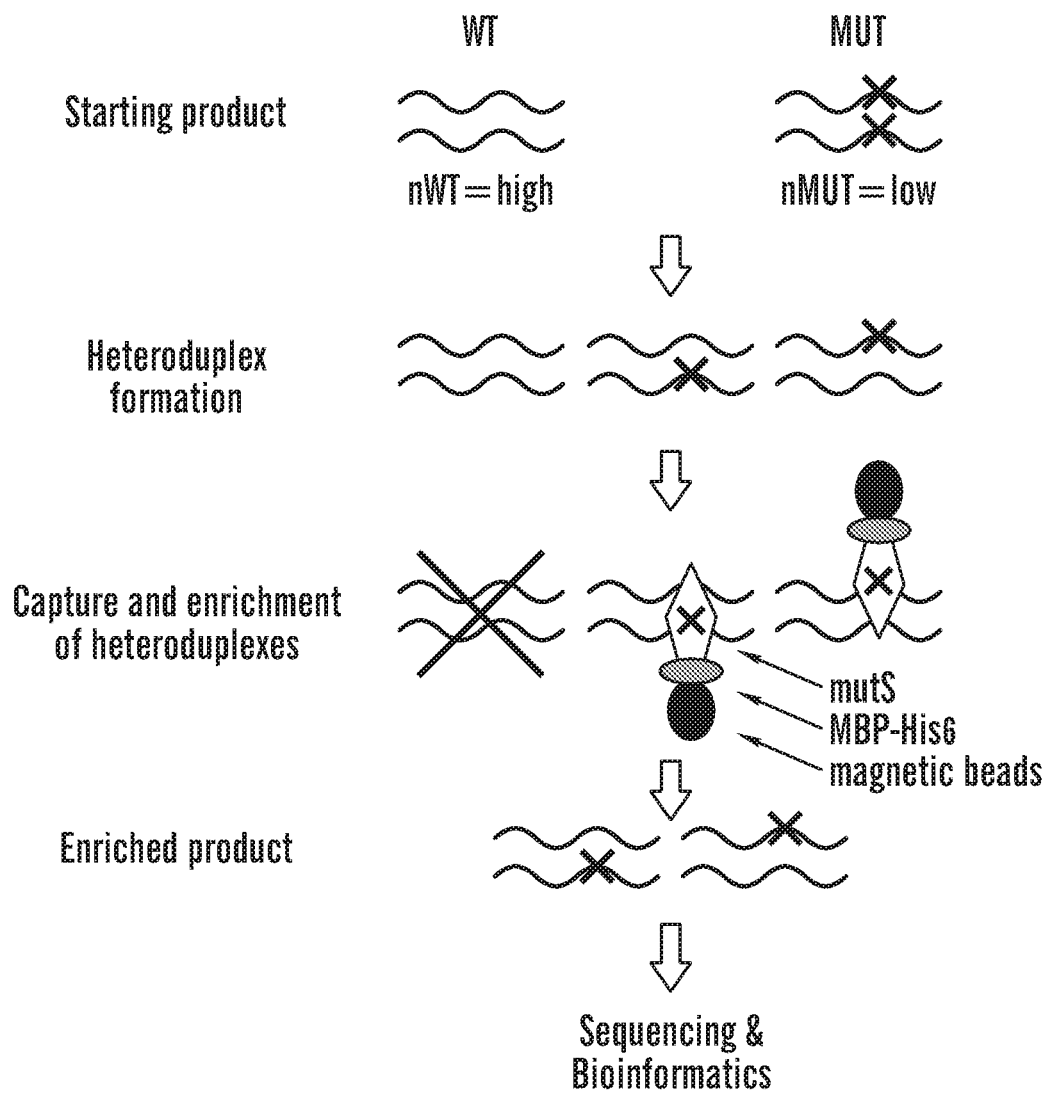
FIG. 5 depicts a schematic representation of the workflow for development of the MutS enrichment approach, as described herein.

In some embodiments, accurate quantification of WT/WT and Mut/Mut homoduplexes and Mut/WT heteroduplexes both before and after attempted MutS enrichment is performed using the RainDrop digital PCR system as shown in FIG. 4. This allows calculation of both enrichment and absolute recovery of mutant DNA at each step in the MutS assay. Development of the MutS enrichment assay can proceed as shown in FIG. 5. First, heteroduplex formation is optimized to achieve, for example, at least ~60% heteroduplex formation at 100:1 ratio. For example, synthetic oligonucleotides matching the 5 amplicons in the UID methods can be designed and purchased with novel PCR primer sequences (to avoid contamination issues). Oligos can be either WT or can include artificial point mutations introduced in the sequence. WT and MUT oligos are PCR amplified individually, column purified and quantified using digital PCR with probes specific to WT and MUT sequences.

Mixtures of WT/MUT at different ratios (eg. 10:1, 100:1, 1000:1) are created and heteroduplex formation quantified using different protocols. Variables include cooling rate following denaturation, multiple denature/cool cycles, different ionic strength buffers and inclusion of destabilizing agents (e.g., DMSO). The protocol that results in maximal heteroduplex formation over a range of DNA concentrations and WT/MUT ratios can be determined.

MutS binding and capture of heteroduplexes can also be optimized. In some embodiments, MutS from Excellgen can be used, which is modified to have both His6 and MBP tags. The His6 tag can be used to detect MutS protein in western blots, while the MBP tag can be used to bind to magnetic beads to allow MutS capture.

Alternatively, MutS can be biotinylated and streptavidin coated magnetic beads used for capture. MutS binding and capture is essentially a Co-IP experiment and can be optimized as such. For example, addition of MutS directly to DNA can be evaluated, followed by bead capture versus initial binding of MutS to beads followed by DNA capture. In addition, different MutS/DNA ratios can be tested and the use of blocking agents in the capture buffer evaluated, use of different ionic strength buffers and different incubation times and temperatures also evaluated (the MutS is from a thermostable bacterium and may function better at higher temperature). In all cases, enrichment and recovery can be quantified precisely using digital PCR. Efficient capture of MutS can be determined by western blot of the captured MutS and the supernatant using antibodies to the His6 tag on MutS, for example.

Finally, different wash procedures to remove any weakly bound homoduplex DNA from the captured beads are evaluated taking into account variables such as the number of washes, ionic strength of the wash buffer, and inclusion of blocking agents. Digital PCR can be used to quantify hetero and homoduplexes retained on the beads and released into the wash buffer to determine the optimal wash conditions. Similarly, western blots can be used to ensure that wash conditions are not releasing the MutS from the beads.

An optimized MutS protocol can be applied to sequencing libraries generated using the methods described herein comprising, for example, tumor DNA mixtures and targets. Sequencing libraries can be generated using the standard Thunderbolts approach, and also with the multiplex UID approaches described herein. MutS enrichment can be performed pre and/or post PCR (FIG. 3) depending on results from the MutS development. If necessary, an additional PCR step can be performed post-enrichment to generate enough product to load on the sequencer. Sequencing results can be compared with and without MutS enrichment to determine the effect of enrichment on mutant allele fraction, mutation calling, background sequencing noise, and read depth requirements for sensitive mutation detection.

Example 2

Detection of cell-free DNA in liquid biopsies offers great potential for use in non-invasive prenatal testing and as a biomarker in patients with cancer. Fetal and tumor DNA fractions however can be extremely low in these samples and ultra-sensitive methods are required for their detection. As described herein, we report an extremely simple and fast method for introduction of barcodes into DNA libraries made from as little as 5 ng of DNA. Barcoded adapter primers are designed with an oligonucleotide hairpin structure to protect the molecular barcodes during the first rounds of PCR and prevent them from participating in mispriming events. This approach enables high-level multiplexing and next-generation sequencing library construction with flexible library content. Utilizing the barcodes to generate consensus reads for each original DNA molecule greatly reduces background sequencing noise and allows detection of variant alleles at or below 0.1% frequency in biologically challenging samples. Thus, the approaches described herein bridge the gap between the highly sensitive but specific capabilities of digital PCR, which only allows a limited number of variants to be analyzed, with the broad target capability of next-generation sequencing which traditionally lacks the sensitivity to detect rare variants.

The ability of massively-parallel, next-generation DNA sequencing (NGS) to identify low prevalence mutations in heterogeneous samples has revolutionized basic and translational research in cancer and many other fields (1). However, detection of sequence variants below 1% frequency remains a challenge with standard NGS protocols due to background noise, much of which is introduced by polymerases during library construction (2). This background noise is problematic in many clinical and research applications, including detection of rare sequence variants in liquid biopsies for non-invasive prenatal diagnostics (NIPD) or for biomarker applications in cancer.

Detection and analysis of fetal DNA in maternal plasma has led to a revolution in non-invasive prenatal diagnostics for Downs Syndrome and other disorders involving large chromosomal abnormalities (3,4). Moving forward, detection of single nucleotide variants specific to the fetus offers the potential to diagnose monogenic disorders early on in pregnancy without the risks associated with chorionic villus sampling or amniocentesis (5-7). In cancer, applications of rare mutation detection in liquid biopsies include analysis of tumor heterogeneity and identification of therapy resistant clones (8), monitoring clonal evolution and response to therapy (9) and early cancer diagnosis using blood/plasma, sputum, urine or other bodily fluids (10-12). In many cases, these scenarios potentially require detection of variant allele fractions of 0.1% or less.

In both NIPT and cancer biomarker research, the introduction of digital PCR technology has enabled detection and quantification of ultra-rare sequence variants in liquid biopsies (13,14). However, digital PCR assays are specific for both nucleotide position and the specific base change. Combined with the fact that multiplexing capability is limited, digital PCR is most useful in situations where a known variant is being sought or where disease-related variants are well characterized and limited in number. For recessive disorders, mutations in tumor suppressor genes and even recurrent mutations in many oncogenes, de novo detection of variants at many base positions is typically required and digital PCR is not the answer. Instead, as described herein, digital sequencing approaches using molecular barcodes offers an attractive alternative.

Figure 10:
FIG. 10 depicts principle of barcoding. Each target DNA molecule is barcoded with a unique sequence. All PCR amplified molecules that are generated from the same original molecule receive the same barcode. Hence, if a PCR error is introduced in the library construction, only a fraction of all DNA molecules with the same barcode will amplify that specific error (left, barcode). Conversely, if a mutation is present in the original molecule all downstream generated amplicons with that particular barcode will have the same mutation and can therefore be called a true mutant (right barcode).

Introduction of molecular barcodes (random oligonucleotide sequences, e.g., N12-14) to uniquely tag individual target DNA molecules can be used to identify and reduce sequencing errors introduced during NGS library construction (FIG. 10) and enables robust detection of ultra-rare variants (15,16). Ligation of barcodes onto target DNA followed by target capture and amplification is inefficient and risks missing rare variants when using low DNA inputs such as those obtained from liquid biopsies. Introduction of barcodes by PCR can be achieved with low DNA inputs (16) but the random barcode sequences behave promiscuously resulting in formation of non-specific PCR products. Consequently, multiplexing is challenging and library construction requires complex, multi-step workflows that include gel purification of PCR products (16). Herein, we report development of a library construction approach that uses hairpin-protected barcode primers to enable Simple, Multiplexed, PCR-based barcoding of DNA for Sensitive mutation detection using Sequencing (SiMSen-Seq). SiMSen-Seq facilitates detection of sequence variants at or below 0.1% allele frequency, works with low DNA input (<50 ng) and can be used to interrogate multiple genome loci covering >1 Kb of target sequence if desired.

Material and Methods

DNA

Wild-type genomic DNA was extracted from a clonally derived Barrett's esophageal cell line, CP-A, using the QIAAMP DNA Mini kit (Qiagen). Wild-type circulating, cell-free DNA (ccfDNA) was extracted from pooled patient plasma (Innovative Research) using QIAAMP Circulating Nucleic Acid kit (Qiagen). DNA concentrations were quantified with the QUBIT 2.0 FLUOROMETER (Life Technologies) and stored at −20° C. Genomic DNA was sheared using a M220 focused-ultrasonicator (Covaris).

Melting Curve Analysis

Hairpin stability was analyzed by melting curve analysis using VARIAN CARY 300 UV-Vis spectrophotometer (Varian, Inc). Primers were analyzed at a concentration of 1 µM in PCR buffer (10 mM Tris-HCl (pH 8.0), 50 mM KCl and 5 mM MgCl2). Samples were degased using preheating at 90° C. for 10 min. The absorbance was measured at 260 nm with a temperature gradient from 25° C. to 90° C., increasing the temperature stepwise, 0.4° C./min. Data were recorded every 0.4° C.

Barcoding and Library Construction

Barcoding of DNA was performed with PCR in 10 µL using 1× ACCUPRIME PCR Buffer II, 0.2 U ACCUPRIME TAQ DNA Polymerase High Fidelity (both Invitrogen, Thermo Fisher Scientific), 40 nM of each primer (IDT, Inc) and 10-100 ng DNA. Primer sequences are shown in Table 1. The temperature profile was 98° C. for 3 min followed by 3 cycles of amplification (98° C. for 10 sec, 62° C. for 6 min and 72° C. for 30 sec), 65° C. for 15 min and 95° C. for 15 min. Twenty µL TE buffer, pH 8.0 (Ambion, Thermo Fisher Scientific) with final concentration of 30 ng/µL protease (*Streptomyces griseus*, Sigma Aldrich) was added to inactivate the Taq DNA polymerase at the 65° C. for 15 min step. The second round of PCR was performed in 40 µL using 1×Q5 HOT START HIGH-FIDELITY Master Mix (New England BioLabs), 400 nM of each Illumina adaptor primer and 10 µL PCR products from the first round of PCR. The temperature profile was 95° C. for 3 min followed by 18-30 cycles of amplification (98° C. for 10 sec, ramping from 80° C. down to 72° C. and up 76° C., 0.2° C. per 1 sec increments, 76° C. for 30 sec). Thirty-six µL PCR products were purified using the AGENCOURT AMPURE XP system (Beckman Coulter, Inc.) according to the manufacturers' instruction. The applied volume ratio between beads and PCR products ranged from 0.83 to 1.0, depending on amplicon length. The purified product was eluted in 20 µL TE buffer, PH 8.0.

Sequencing

Prior to sequencing, libraries were assessed by a Fragment Analyzer (Advanced Analytic Technology, Inc.; Ames, Iowa, USA). For quality assessment, some libraries were initially run on a MISEQ using the NANO KIT V2, single-end 150 and either MISEQ single-end 150 or HISEQ2500 paired-end 150 were used for library sequencing (Illumina, Inc.; San Diego, Calif., USA).

Sequence Analysis

FASTQ files were aligned to hg19 using bwa mem (0.7.12) with output sorted and indexed using samtools (0.1.19). A custom pipeline was used to build consensus sequences as follows: The N most frequent amplicons were identified in the bamfile according to the library plexity and indexed by start position. Valid reads within each amplicon were then defined as those containing the 12 nucleotides random barcode in the correct location relative to the hairpin stem. Valid reads were grouped into families by start position and barcode ID. For each family, raw read alignments were used to determine the identity of bases (including indels) at each genomic position. Non-reference bases were reported if they composed 100% of the reads in families with 10-20 reads, or at least 90% of reads in families with >20 reads.

Results

NGS Library Primers can be Designed to be in Open or Closed Configuration Using a Temperature-Dependent Hairpin Structure The major obstacle in PCR multiplexing is unwanted interactions between primers forming non-specific PCR products. The amount of non-specific PCR products depends on the number of primers multiplexed, but also on their length and sequence (17). Randomized sequences, such as barcodes, are potentially more prone to form non-specific PCR products, since they can interact promiscuously with adapter and target portions of all primers in the reaction. To solve this issue, as described herein, we designed a universal hairpin structure that protects the barcode and adapter sequences from spurious interaction, while leaving the target portion of the primer available for hybridization during the first steps of library construction (FIGS. 6A-6B). The hairpin protected barcode primer consists of: (i) standard target primer sequence, (ii) 12 randomized nucleotides used as barcode, (iii) adaptor primer sequence and (iv) 14 nucleotides forming a hairpin stem. The stem sequence was designed to be in a closed hairpin configuration at the PCR annealing temperature (60-62° C.), but in an open state at the PCR elongation temperature (72-76° C.). To minimize the primer length and hairpin size we used nucleotides in the sequencing adaptor region as a backbone to design the stem. Two additional guanine bases 5' of the adaptor sequence (GG hairpin stabilizer) allowed us to increase the hairpin melting temperature. Furthermore, we included 2 nucleotides 3' of the barcode (AT hairpin destabilizer) separating the barcode from the stem sequence. These nucleotides create two forced mismatches, ensuring that bases in the barcode do not strengthen the stem stability in a sub-fraction of the primers. To evaluate the hairpin melting temperature and its variability between primers we analyzed 36 primers with different DNA target sequences using melting curve analysis in a temperature controlled spectrophotometer (FIG. 6C). All primers with the same hairpin-stem structure displayed almost identical melting temperature demonstrating a stable and robust hairpin design (mean±SD=74.0° C., ±0.3° C.; FIG. 6D).

Figure 7:
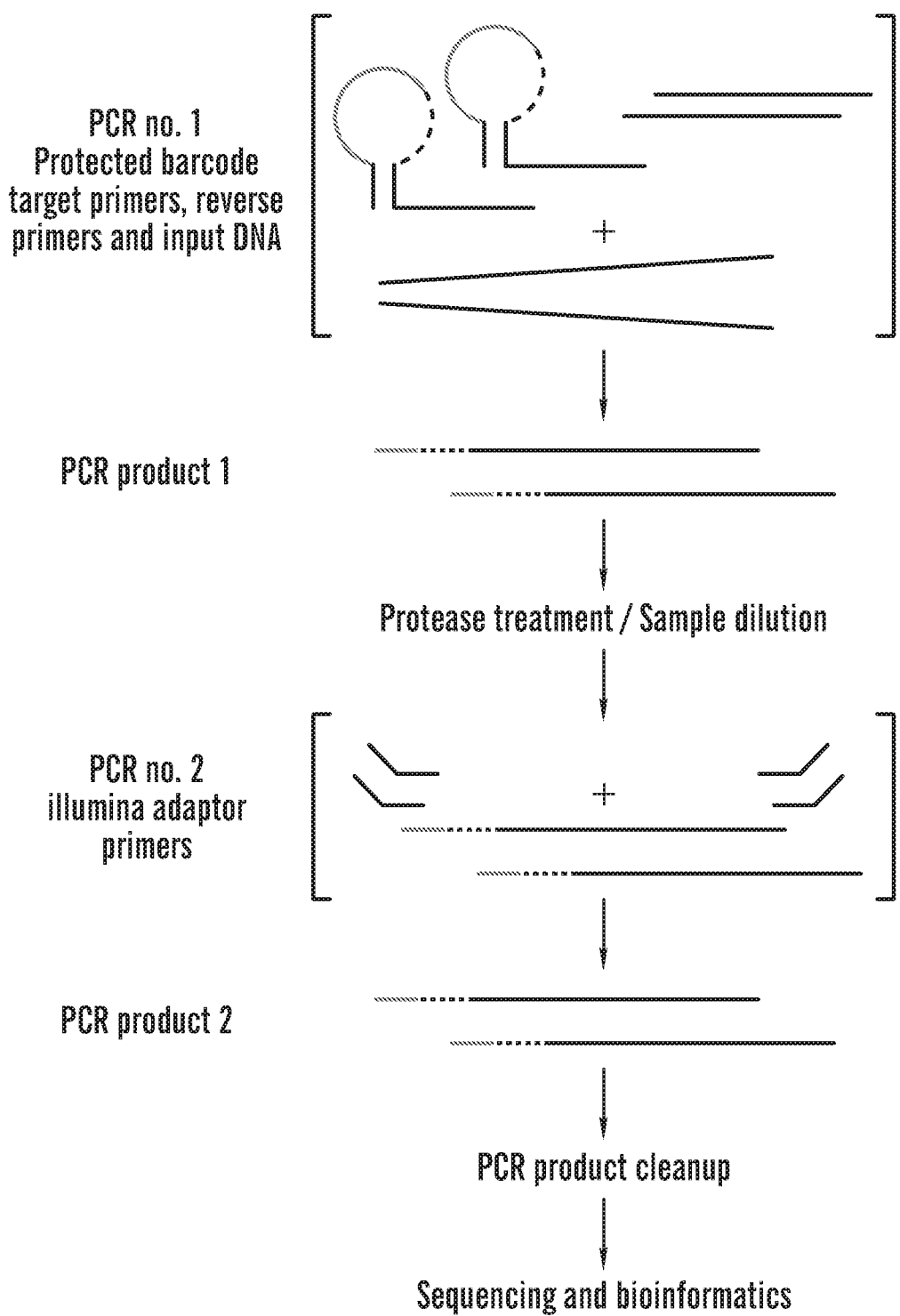
FIG. 7 depicts an exemplary schematic library construction workflow. In the first PCR consisting of 3 cycles, target DNA is amplified with hairpin protected barcode primers. The reaction is terminated with an incubation step that is a combined dilution and protease treatment step. In the second PCR that consists of 18-30 cycles, all individual amplicons are amplified to generate PCR products with Illumina adapter primers. Final libraries are purified with magnetic beads, normalized for concentration differences between samples and sequenced.
Figures 8A, 8B:
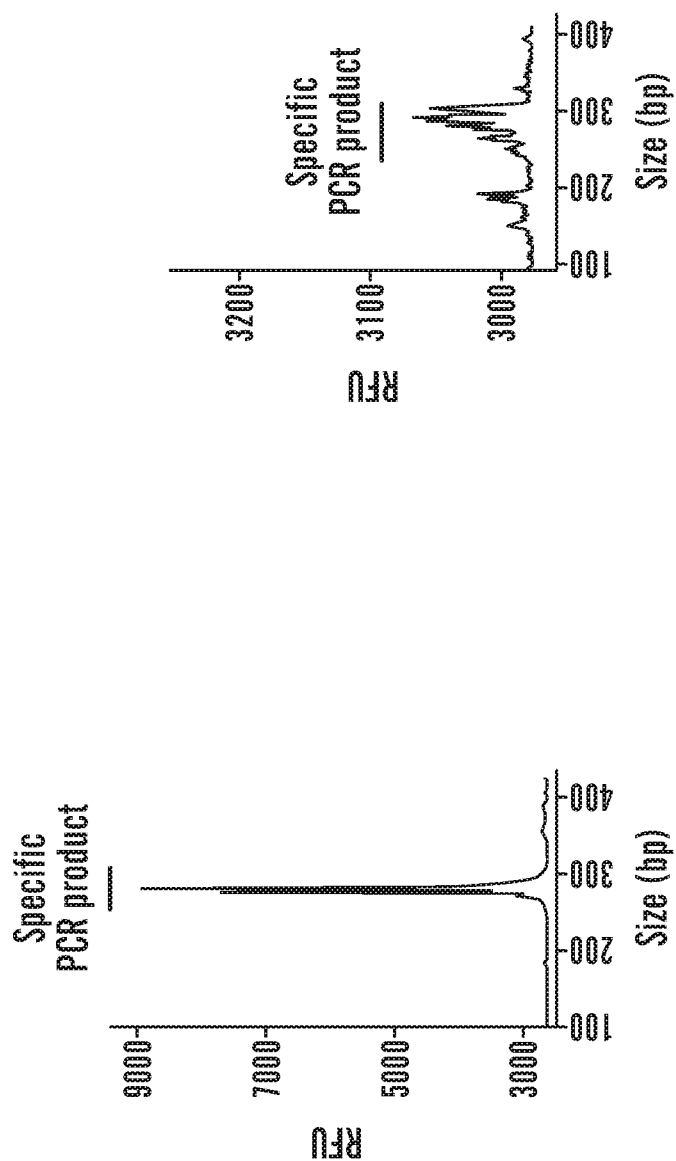
FIGS. 8A-8C demonstrate library purity and uniformity.
Figure 8C:
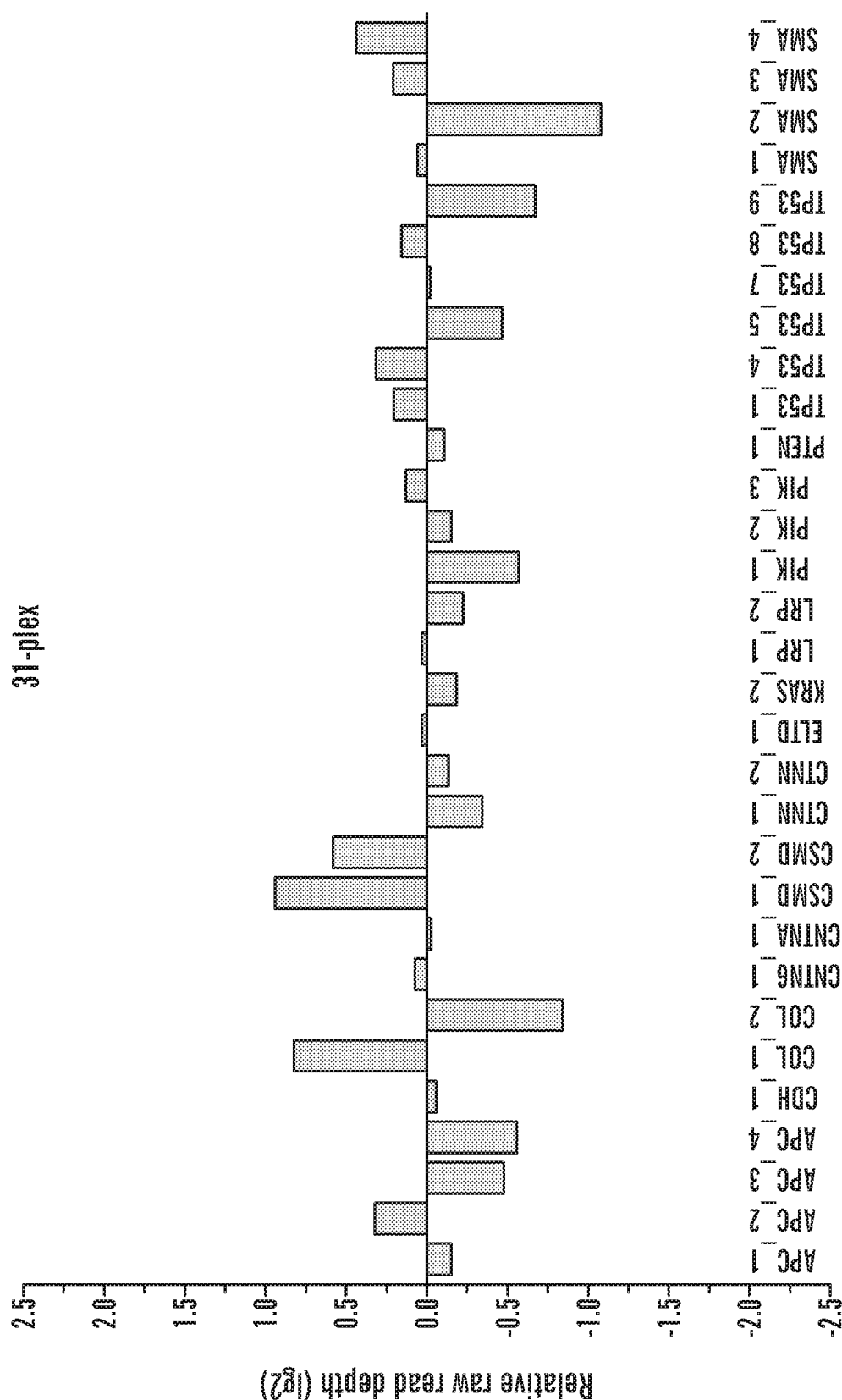
Figure 11:
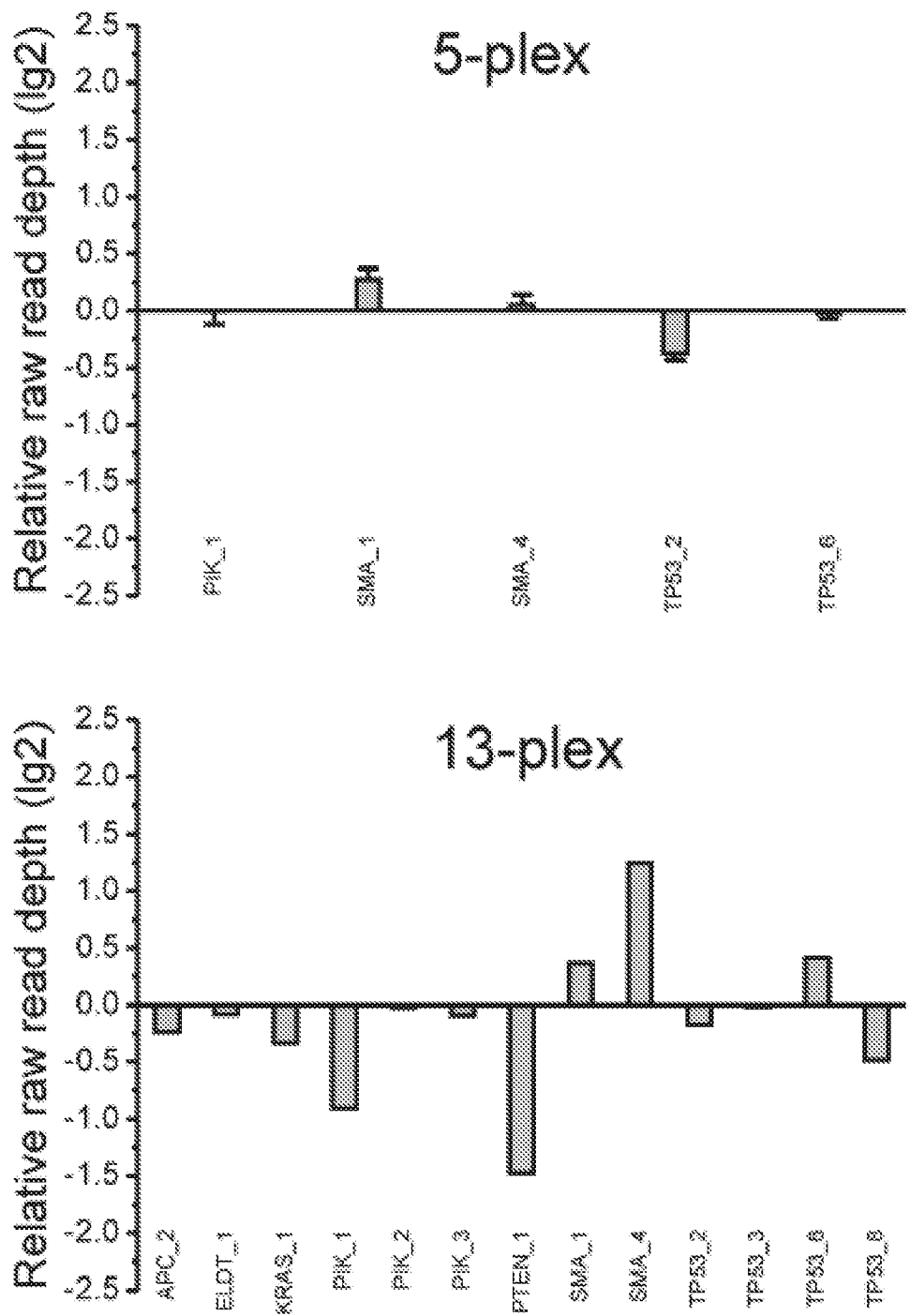
FIG. 11 depicts relative raw reads uniformity between individual amplicons using SiMSen-Seq. Relative raw read depth of 5 and 13 multiplexed amplicons were analyzed. DNA from tumor cell line CP-A was used for all experiments. Mean±SD is shown for the 5 multiplexed amplicons (Top panel; n=12).

Determination of a Simple, Robust and Fast Library Protocol Using Barcoding: SiMSen-Seq Provided herein are novel methods termed SiMSen-Seq (Simple, Multiplexed, PCR-based barcoding of DNA for Sensitive mutation detection using Sequencing), such approaches comprises two series of PCR amplification using high fidelity DNA polymerases (FIG. 7). In the first PCR or the "pre-amplification PCR," each target DNA is barcoded using the hairpin-protected barcode primers. To further reduce the formation of non-specific PCR products in the first PCR, we applied a standard multiplex pre-amplification strategy using 40 nM primer concentrations (10-20 times lower than in a standard PCR) and to compensate the annealing time was extended to 6 minutes. The reaction was then terminated using a combined dilution and protease treatment step at 65° C. for 15 min, to minimize the formation of non-specific PCR products in downstream handling, followed by protease inactivation at 95° C. for 15 min. The resulting products were used directly in the second PCR step or "amplification PCR step" in which barcoded DNA molecules were amplified with Illumina adaptor primers to generate complete libraries. A PCR product clean-up was then performed with the AGENCOURT AMPURE XP magnetic bead system. Using SiMSen-Seq we have successfully generated libraries targeting from 1 up to 31 different genomic DNA sequences in a single reaction (FIGS. 8A-8B). Relative raw read uniformity between individual amplicons was evaluated for 5, 13 and 31 multiplexed amplicons (FIG. 11 and FIG. 8C) and the relative read depth for each amplicon was within 1.4-fold of the mean with high reproducibility (SD<0.12; n=12) for the 5-plex libraries. For the 13- and 31-plex libraries, the relative read depth for each amplicon was within 1.5-fold and 1.4-fold of the mean, respectively.

SiMSen-Seq Reduces Sequencing Errors of all Nucleotides

Figure 9C:
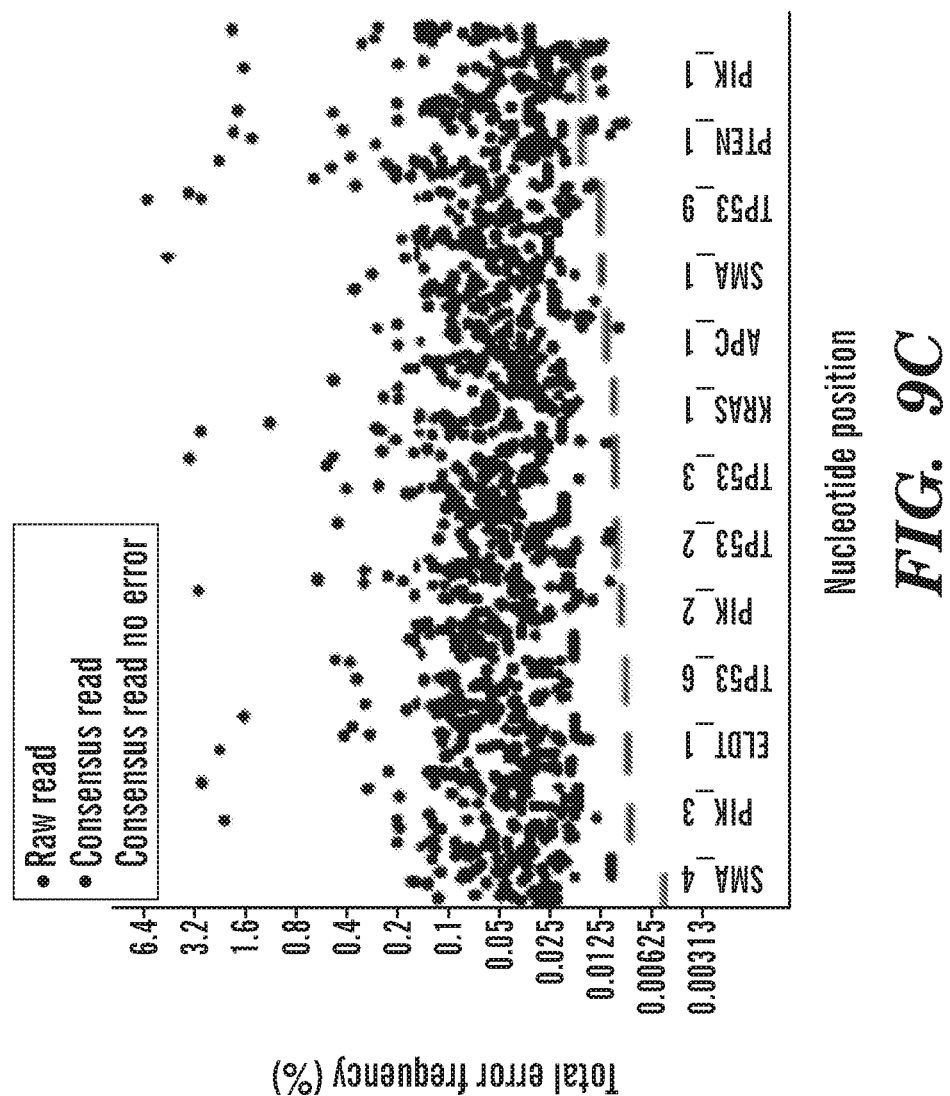
Figure 12:
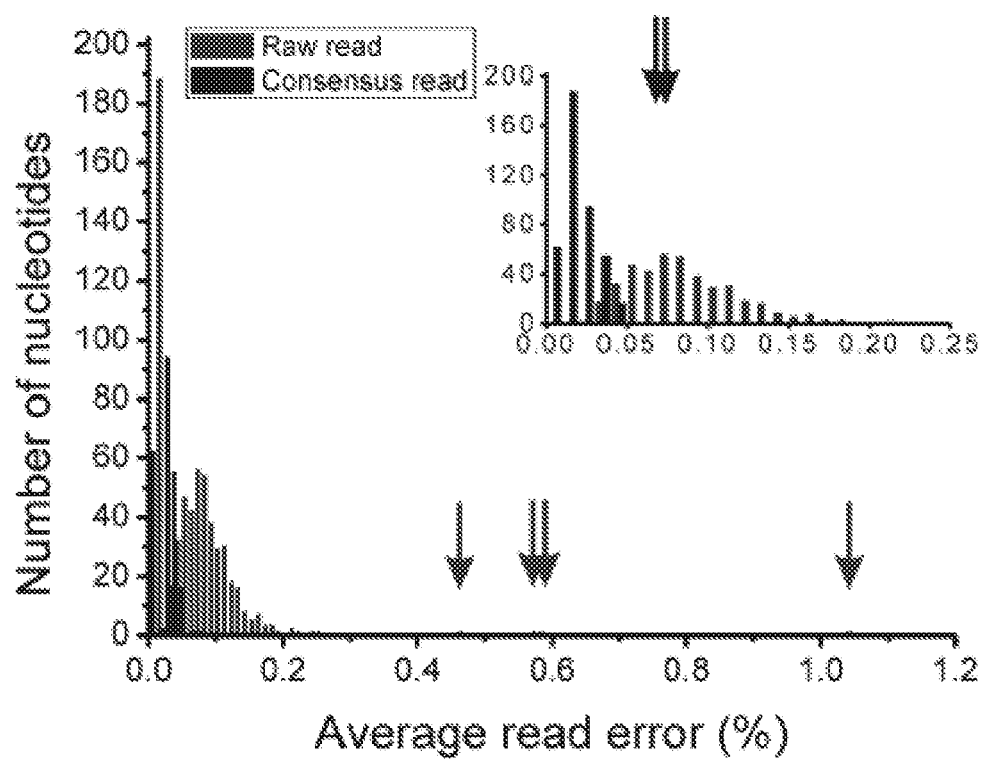
FIG. 12 depicts read error parameters. Distribution of average read errors for total raw and consensus reads. Arrows indicate single nucleotides.
Figure 13A:
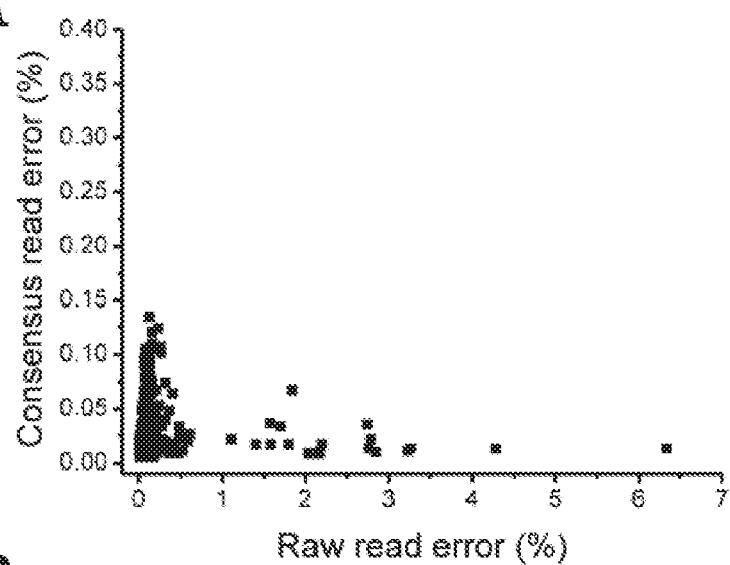
FIGS. 13A-13B depict read error parameters.
Figure 13B:
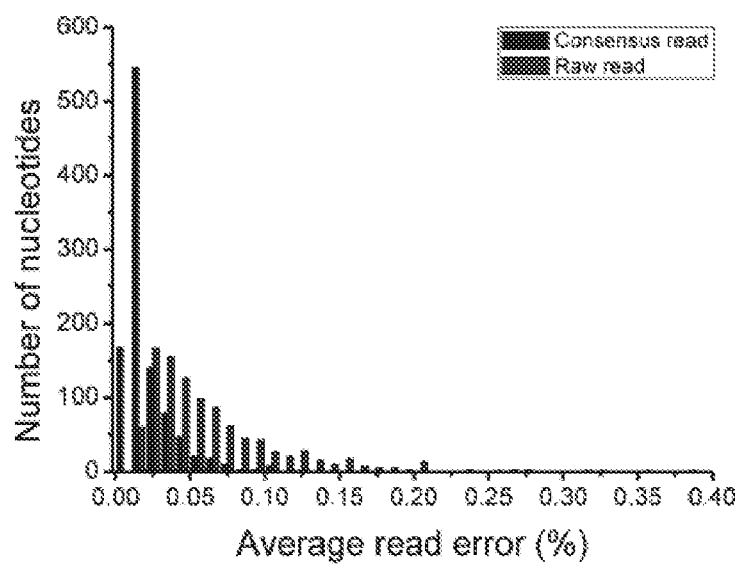

For sequencing error correction using SiMSen-Seq, raw reads mapping to the same amplicon position, and with the same unique barcode, were grouped into barcode families. Barcode families containing a minimum of 10 or 30 raw reads (depending on raw read depth) were then used to compute consensus reads. Consensus was determined for each base in the amplicons and we required 100% identical reads for families with 10-20 reads and >90% identical reads for families with >20 reads. FIG. 9A shows the uniform reduction of total error frequency using barcoding for 417 nucleotides across 5 amplicons analyzed in 12 replicates. The average error correction using consensus reads was 7.3-fold and the maximum correction for any nucleotide was 135-fold. 40.2% of all nucleotides (2014 out of 5004 nucleotides) displayed no consensus read error and 99.3% of nucleotides showed a consensus error <0.1% with 95% confidence (FIG. 9B and FIG. 12). Four hot spot nucleotides (0.96% of all nucleotides) with raw read errors >0.4% were identified and all were corrected to <0.05% error with barcoding Next, we increased the multiplexing to 13 amplicons that covered 1042 nucleotides (FIG. 9C). Data were consistent with the 5-plex experiment. Here, the average error correction was 7.2-fold, 59.5% of all nucleotides showed no consensus read error and 98.9% of all nucleotides showed a consensus error <0.1%. Thirty nucleotides (30/1042; 2.9%) were hot spot positions for raw sequencing error (FIGS. 13A-13B) and all were corrected to <0.07% error with barcoding (maximum correction factor was 475-fold). The 5 multiplexed amplicons analyzed above were also included in the 13-plex analysis and once again, 4 hot spot nucleotides were observed. However, only 1 hot spot nucleotide was common to both runs, while 7 hot spot positions were different in the two experimental setups. This data also serves to illustrate that barcoding can eliminate sequencing errors that occur even with extremely deep sequencing (minimum read depth at hotspots in our study was $5.5 \times 10^5$). In all of the above analyses, DNA from the same clonally derived cell line, CP-A, were used. In all experiments, consensus read error was <0.15% for all base positions.

SiMSen-Seq Allows Rare Mutations to be Detected in Blood Plasma Samples

Figure 9D:
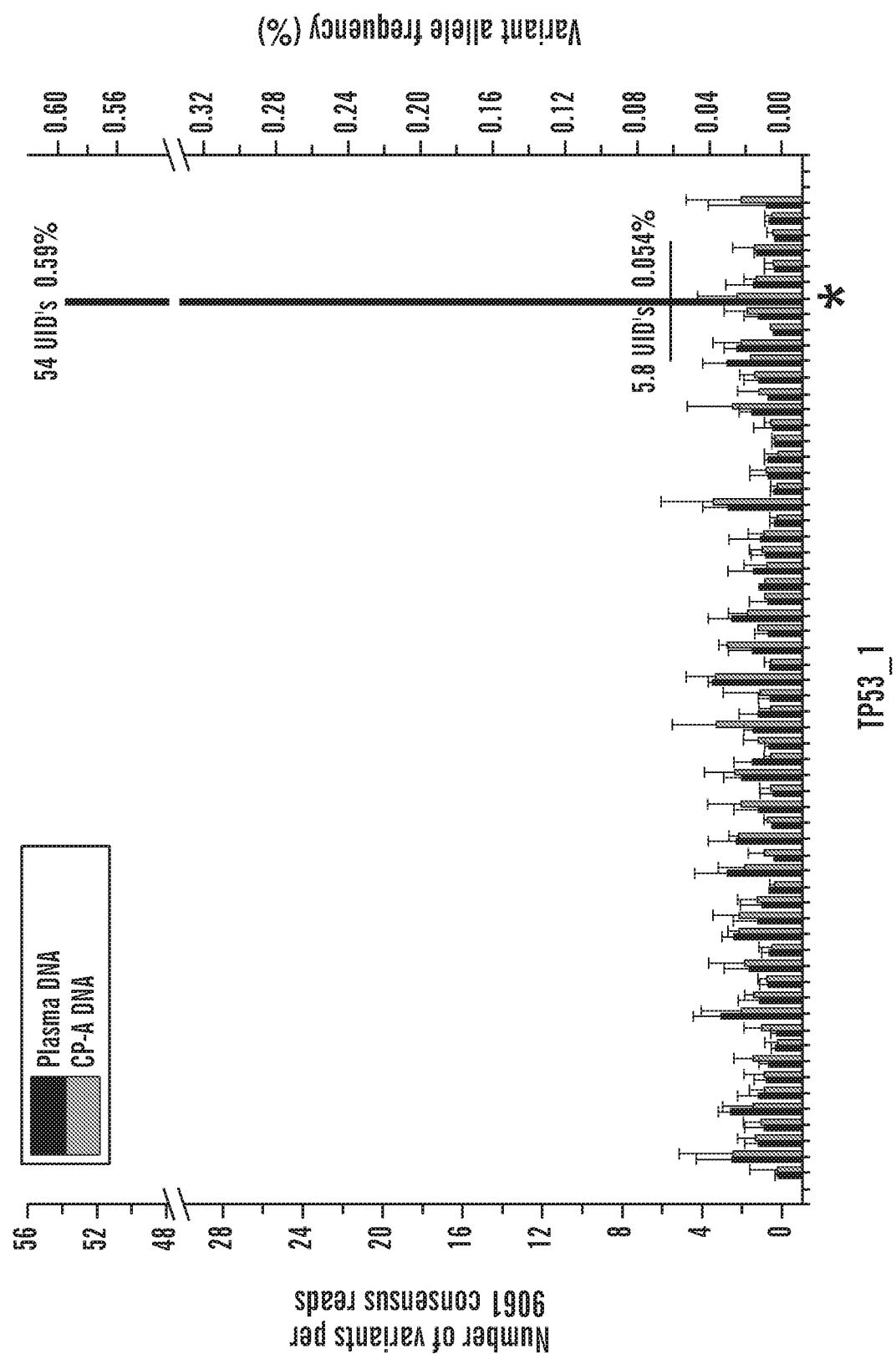
Figure 14:
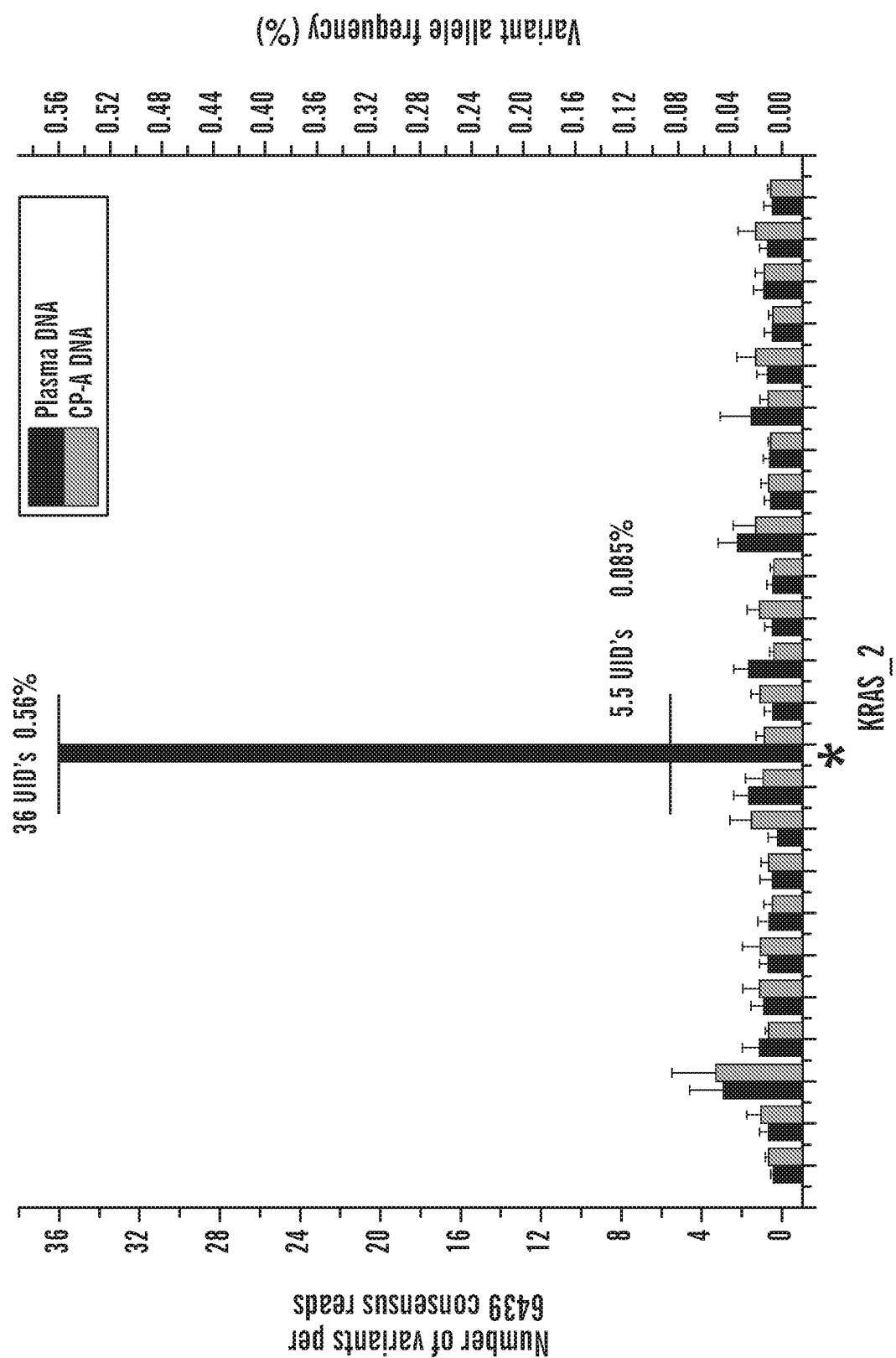
FIG. 14 demonstrates rare mutation detection in APC, KRAS and TP53. Number of variants per nucleotide is shown with corresponding variant allele frequency on the right side y-axis. Pooled plasma DNA from more than 10 individuals and DNA from a clonal derived cell line (CP-A) were analyzed with SiMSen-Seq (n=3-4). Primary tumor DNA with known mutations (marked *) were spiked into the plasma DNA using different mutated DNA concentrations using 10-fold dilution. Additional variants are indicated by number. These variants most likely originated from the plasma DNA and not the spiked in tumor DNA, since their frequencies remained almost constant regardless the amount of spiked in primary tumor DNA. Detailed variant analysis is shown in TABLE 3. For most experiments, clonally derived cell line DNA was used in order to minimize the amount of true, low-level mutations. Interestingly, when it was changed to plasma DNA for spike-in experiments, several base positions were identified with consistent variant allele frequencies above background (0.10-0.64%). Plasma used for this experiment was purchased from a commercial provider and is allegedly pooled from blood of healthy individuals. The data described herein indicates that there may be biological background (true low-level variations) in plasma DNA that occur at variable allele frequency. If true, understanding this background among individuals is important for applications such as early cancer detection.
Figure 14:
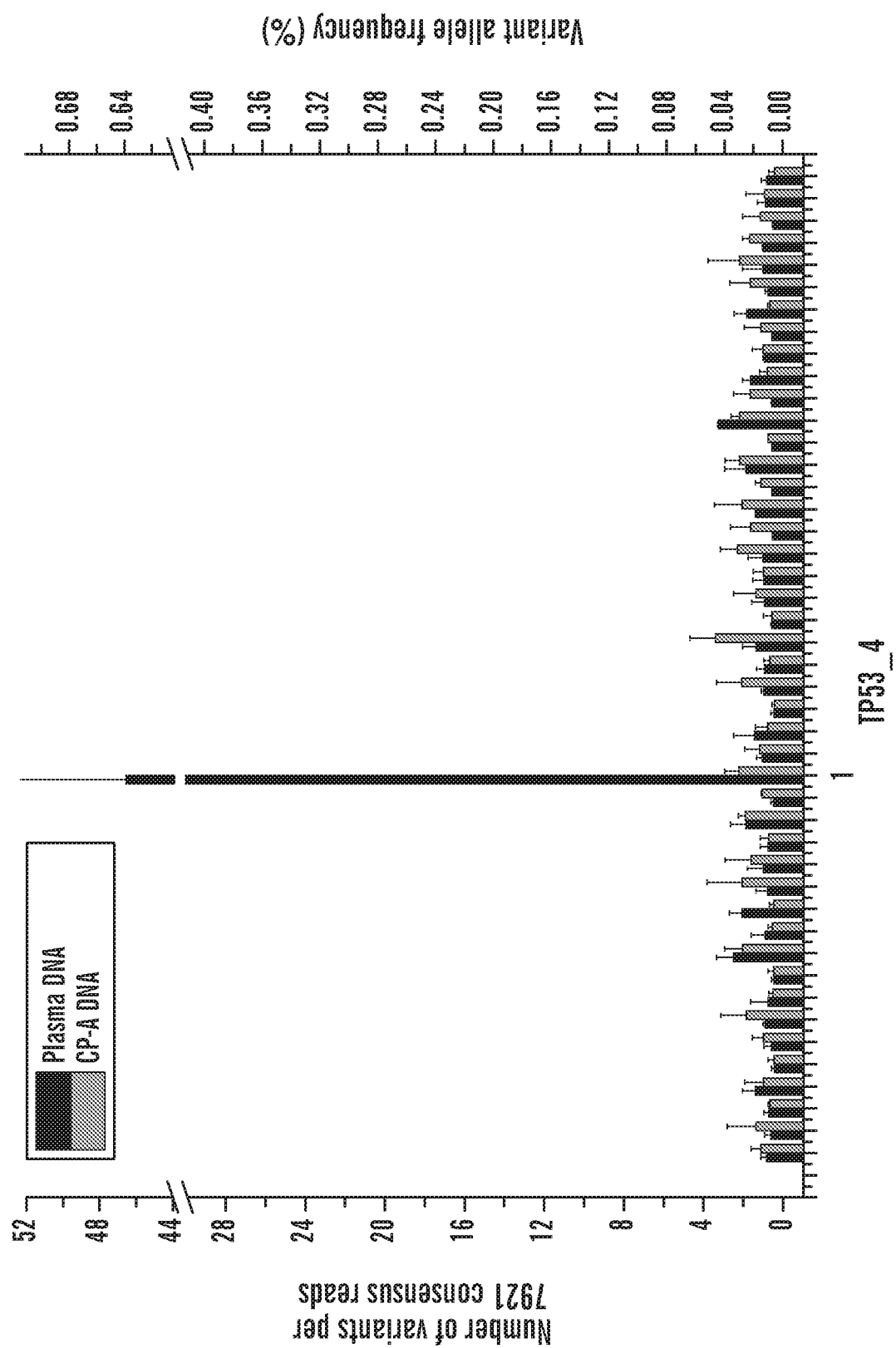
Figure 14:
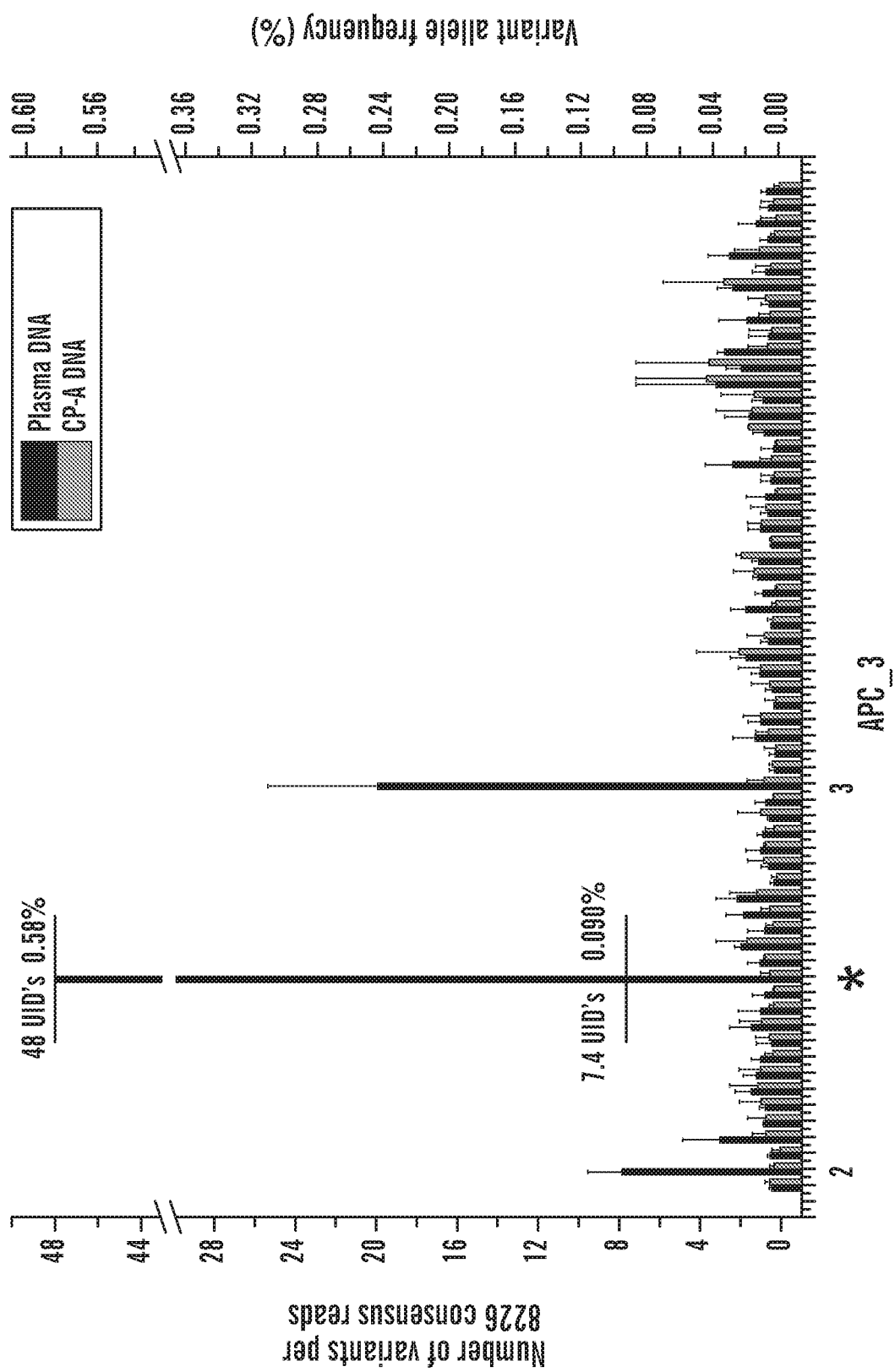
Figure 14:
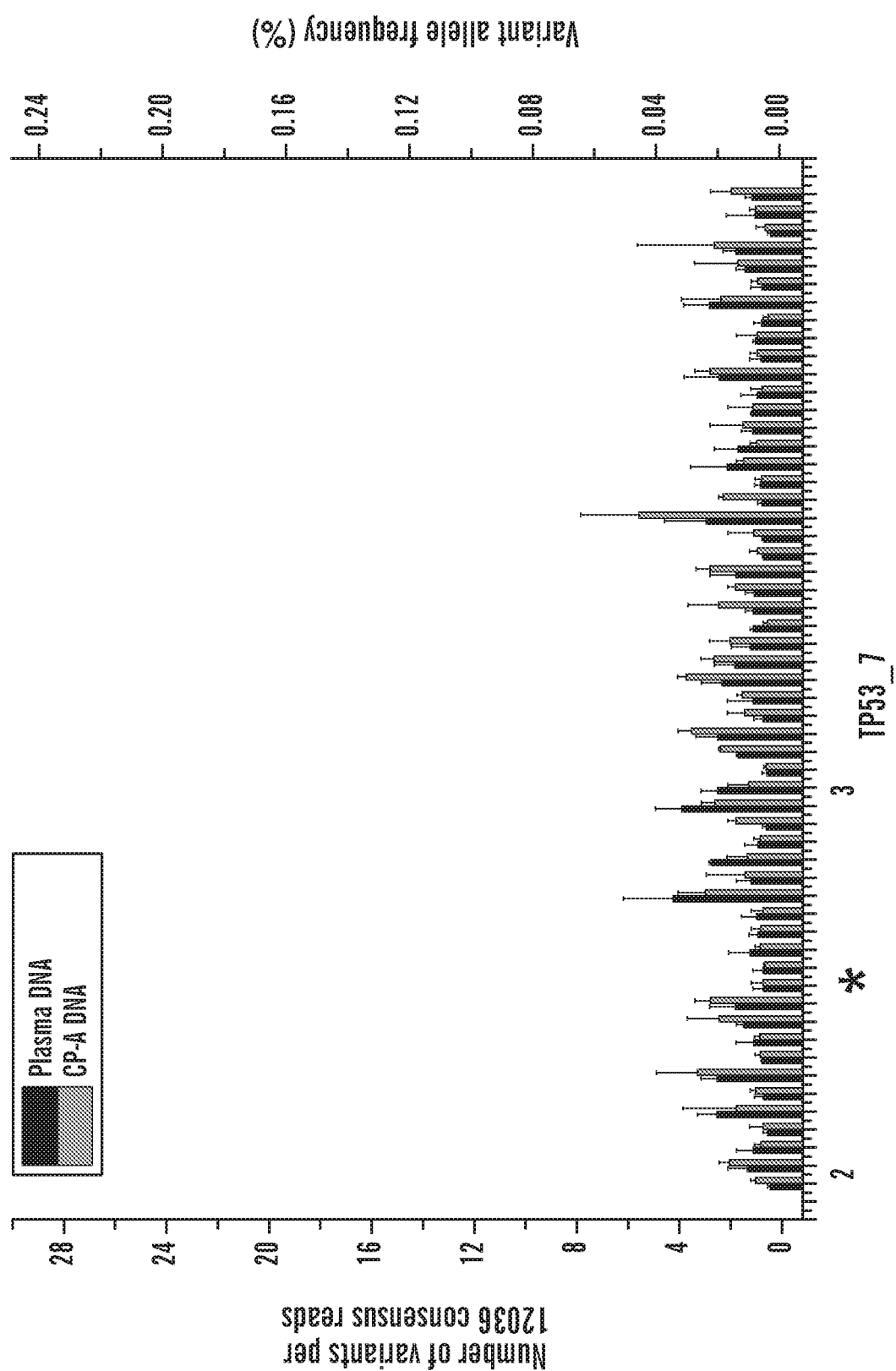

To evaluate SiMSen-Seq sensitivity, we spiked primary tumor DNA with known mutations into pooled plasma DNA prepared from >10 individuals without any known disease. For comparison, we also analyzed DNA from the cell line CP-A. Five short amplicons (≤107 base pairs) targeting 252 nucleotides were analyzed (Table 1). FIG. 9D shows detection of a spiked in TP53 mutation at two different frequencies (0.59% and 0.064%, respectively). In addition to frequency, the absolute number of variants per nucleotide is also indicated in the plot. The upper 95% confidence interval of the control CP-A DNA for that given nucleotide was 0.065%. Two additional spike in mutations are shown in FIG. 14. In addition to the known spike in mutations we also observed several variants in the plasma DNA at frequencies between 0.10% and 0.64% that did not originate from the primary tumor DNA (FIG. 14 and TABLE 3).

Discussion

Incorporating barcodes into NGS libraries using PCR permits background noise reduction and sensitive mutation detection with low DNA inputs. PCR-introduced barcoding applied to a single target sequence was first reported by Kinde et al. using an approach named Safe-SeqS (16). However, SafeSeqS has not found widespread use and we were unable to reliably reproduce the Safe-Seqs protocol in our laboratory due to non-specific PCR that eliminated formation of the desired product. SiMSen-seq solves this issue by protecting the barcodes in a molecular hairpin during the initial round of PCR. This prevents the barcodes from participating in mis-priming events, minimizes non-specific PCR products and enables robust formation of the desired product. In doing so, SimSen-seq also enables high-level multiplexing and eliminates the need for gel-purification of PCR products as in the SafeSeqS approach. Importantly, as long as the target primer sequence is designed with standard criteria (primer annealing temperature 58-62° C. and 20-80% GC content) the hairpin structure is universal for all forward primers. In our experience, failure of any SiMSen-Seq assay could always be traced back to poorly functioning target primers and this can be easily ascertained prior to purchasing primers that incorporate hairpins. When good target primers are selected, we found that all amplicons performed well in SiMSen-Seq, providing reasonably uniform raw read depths and consensus read depths. This was true in the 5-plex, 13-plex and 31-plex data and there is no reason to believe that higher order multiplexing would not perform similarly. However, error reduction by barcoding requires very high sequencing depth (400,000-800,000 reads per target) and thus can get very expensive depending on the number of targets analyzed. This highlights a major advantage of SiMSen-Seq over both SafeSeqS and, any potential ligation and capture approach, in that it is very flexible and amplicons can be used in combinations with varying levels of multiplexing Thus, sequencing costs can be minimized by the use of appropriately sized panels designed for specific uses or even for specific samples, such as analysis of plasma DNA in cancer patients where mutations in the tumor are already known. In addition, SimSes-seq uses an extremely simple library preparation workflow that is completed within three hours, eliminating several enzymatic and purification steps that are associated with most NGS protocols, including the Safe-Seqs protocol. Furthermore, the library preparation is highly cost-efficient, since primers and reagents can be purchased individually as needed.

As with any barcoding approach, SiMSen-Seq cannot correct for polymerase-induced errors introduced in the first PCR extension as all daughter molecules will contain the same error and barcode. Furthermore, although SiMSen-Seq does work with two cycles of PCR barcoding (data not shown), we choose to use three cycles as it results in the production of more barcoded template molecules and allows us to inactivate the first PCR with a combined TE buffer dilution and protease digestion step instead of performing a more labor intensive PCR clean-up. Using three cycles does however potentially reduce error correction as polymerase errors in the second PCR extension, initiated by a new barcoded primer, will also be incorporated into all subsequent daughter strands with that barcode. Thus, additional uncorrectable errors (background noise) are introduced using three cycles versus two, but with the benefit of an easier workflow. However, sequencing errors may also be introduced by factors other than the polymerase, including chemically modified nucleotides present in the template DNA and base calling errors that are not dependent on the number of initial PCR cycles (12). Regardless, our experimental setup with SiMSen-Seq was able to clean-up all raw-read hot spot nucleotides, demonstrating that the applied approach is suitable to accurately detect rare sequence variants down to ~0.1%. This corresponds to 10 molecules or less in most of our analyses.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A method of amplifying a target nucleic acid in a sample comprising:
    a. contacting a sample comprising a target nucleic acid with a target-specific hairpin barcode forward primer and a target-specific reverse primer, wherein the hairpin barcode forward primer comprises, in a 5' to 3' direction: a 5' stem sequence, an adaptor sequence, a barcode sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature;
    b. amplifying the target nucleic acid by performing 2-5 cycles of PCR pre-amplification on the target nucleic acid, wherein the 2-5 cycles of PCR pre-amplification have an annealing temperature less than or equal to the closed annealing temperature of the hairpin barcode forward primer, to generate a plurality of pre-amplification target nucleic acids;
    c. contacting the plurality of pre-amplification target nucleic acids with an adaptor-specific forward primer and an adaptor-specific reverse primer; and
    d. amplifying the pre-amplification target nucleic acid by performing at least 10 cycles of PCR amplification on the pre-amplification target nucleic acids, wherein at least 3 of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.
2. The method of paragraph 1, wherein the 3' stem sequence is 12-15 nucleotides.
3. The method of any one of paragraphs 1-2, wherein the 3' stem sequence and the adaptor sequence each comprise sequence complementary to each other and the complementary sequences hybridize to each other at a closed annealing temperature and do not hybridize to each other at an open annealing temperature.
4. The method of paragraph 3, wherein the 3' stem sequence and the adaptor sequence comprise 10-12 nucleotides of sequence completely complementary to each other.
5. The method of any one of paragraphs 1-4, wherein the hairpin barcode forward primer further comprises at least two destabilizing nucleotides 3' of the barcode sequence.

6. The method of any one of paragraphs 1-5, wherein the closed annealing temperature is equal to or less than 60° C.
7. The method of any one of paragraphs 1-6, wherein the open annealing temperature is at least 65° C.
8. The method of any one of paragraphs 1-7, wherein the barcode sequence is 6-18 nucleotides.
9. The method of any one of paragraphs 1-8, wherein the barcode sequence is 14 nucleotides.
10. The method of any one of paragraphs 1-9, wherein the hairpin barcode forward primer comprises one or more non-conventional nucleotides.
11. The method of any one of paragraphs 1-10, wherein the target-specific reverse primer is a hairpin barcode reverse primer, wherein the hairpin barcode reverse primer comprises, in a 5' to 3' direction: a 5' stem sequence, an adaptor sequence, a barcode sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature.
12. The method of any one of paragraphs 1-11, wherein the method further comprises a step of detecting or sequencing the plurality of target nucleic acid amplicons.
13. A method of pre-amplifying a target nucleic acid in a sample comprising:
    a. contacting a sample comprising a target nucleic acid with a target-specific hairpin barcode forward primer and a target-specific reverse primer, wherein the hairpin barcode forward primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other, and the complementary sequences hybridize to each other under a closed annealing temperature and do not hybridize to each other at an open annealing temperature; and
    b. pre-amplifying the target nucleic acid by performing at least one cycle of PCR pre-amplification on the target nucleic acid, wherein the at least one cycle of PCR pre-amplification has an annealing temperature less than or equal to the closed annealing temperature of the hairpin barcode forward primer, thereby generating a plurality of pre-amplification target nucleic acids.
14. A method of amplifying a target nucleic acid in a sample comprising:
    a. contacting a sample comprising a target nucleic acid with a target-specific hairpin barcode forward primer and a target-specific reverse primer, wherein the hairpin barcode forward primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other, and the complementary sequences hybridize to each other under a closed annealing temperature and do not hybridize to each other at an open annealing temperature;
    b. pre-amplifying the target nucleic acid by performing at least one cycle of PCR pre-amplification on the target nucleic acid, wherein the at least one cycle of PCR pre-amplification has an annealing temperature less than or equal to the closed annealing temperature of the hairpin barcode forward primer, to generate a plurality of pre-amplification target nucleic acids;
    c. contacting the plurality of pre-amplification target nucleic acids with an adaptor-specific forward primer and an adaptor-specific reverse primer; and
    d. amplifying the pre-amplification target nucleic acid by performing at least 10 cycles of PCR amplification on the pre-amplification target nucleic acids, wherein the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.
15. The method of any one of paragraphs 13 or 14, wherein the sequence to be protected comprises a barcode sequence.
16. The method of any one of paragraphs 13 or 14, wherein the sequence to be protected comprises an adaptor sequence.
17. The method of any one of paragraphs 13 or 14, wherein the sequence to be protected comprises, in the 5' to 3' direction, a barcode sequence and an adaptor sequence.
18. The method of any one of paragraphs 13-17, wherein the 3' stem sequence is 5-20 nucleotides.
19. The method of any one of paragraphs 13-17, wherein the 3' stem sequence is 12-15 nucleotides.
20. The method of any one of paragraphs 16-19, wherein the 3' stem sequence and the adaptor sequence each comprise sequence complementary to each other, and the complementary sequences are hybridized to each other at a closed annealing temperature and do not hybridize to each other at an open annealing temperature.
21. The method of paragraph 20, wherein the 3' stem sequence and the adaptor sequence comprise 10-12 nucleotides of sequence completely complementary to each other.
22. The method of any one of paragraphs 15 or 17-21, wherein the hairpin barcode forward primer further comprises at least two destabilizing nucleotides 3' of the barcode sequence.
23. The method of paragraph 22, wherein the at least two destabilizing nucleotides are T and A.
24. The method of any one of paragraphs 13-23, wherein the closed annealing temperature is equal to or less than 60° C.
25. The method of any one of paragraphs 13-24, wherein the open annealing temperature is at least 65° C.
26. The method of any one of paragraphs 15 or 17-25, wherein the barcode sequence is 6-18 nucleotides.
27. The method of any one of paragraphs 15 or 17-26, wherein the barcode sequence is 14 nucleotides.
28. The method of any one of paragraphs 13-27, wherein the hairpin barcode forward primer comprises one or more non-conventional nucleotides.
29. The method of any one of paragraphs 13-28, wherein the target-specific reverse primer is a hairpin barcode reverse primer, wherein the hairpin barcode reverse primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other and the complementary sequences hybridize to each other under a closed annealing temperature, and do not hybridize to each other at an open annealing temperature.

30. The method of any one of paragraphs 13-29, wherein the method further comprises a step of detecting or sequencing the plurality of target nucleic acid amplicons.

31. The method of any one of paragraphs 1-30, wherein the concentration of target-specific hairpin barcode primer used is less than or equal to 100 nM.

32. The method of any one of paragraphs 1-31, wherein the concentration or unit amount of a DNA polymerase used for pre-amplifying or amplifying is 4-10 fold lower than the concentration or unit amount recommended by the manufacturer.

REFERENCES 1. ten Bosch, J. R. and Grody, W. W. (2008) Keeping up with the next generation: massively parallel sequencing in clinical diagnostics. The Journal of molecular diagnostics: JMD, 10, 484-492.
2. Fox, E. J., Reid-Bayliss, K. S., Emond, M. J. and Loeb, L. A. (2014) Accuracy of Next Generation Sequencing Platforms. Next Gener Seq Appl, 1.
3. Lo, Y. M. and Chiu, R. W. (2012) Genomic analysis of fetal nucleic acids in maternal blood. Annu Rev Genomics Hum Genet, 13, 285-306.
4. Diaz, L. A., Jr. and Bardelli, A. (2014) Liquid biopsies: genotyping circulating tumor DNA. Journal of clinical oncology: official journal of the American Society of Clinical Oncology, 32, 579-586.
5. New, M. I., Tong, Y. K., Yuen, T., Jiang, P., Pina, C., Chan, K. C., Khattab, A., Liao, G. J., Yau, M., Kim, S. M. et al. (2014) Noninvasive prenatal diagnosis of congenital adrenal hyperplasia using cell-free fetal DNA in maternal plasma. J Clin Endocrinol Metab, 99, E1022-1030.
6. Chitty, L. S. and Lo, Y. M. (2015) Noninvasive Prenatal Screening for Genetic Diseases Using Massively Parallel Sequencing of Maternal Plasma DNA. Cold Spring Harb Perspect Med, 5.
7. Tsui, N. B., Kadir, R. A., Chan, K. C., Chi, C., Mellars, G., Tuddenham, E. G., Leung, T. Y., Lau, T. K., Chiu, R. W. and Lo, Y. M. (2011) Noninvasive prenatal diagnosis of hemophilia by microfluidics digital PCR analysis of maternal plasma DNA. Blood, 117, 3684-3691.
8. Murtaza, M., Dawson, S. J., Tsui, D. W., Gale, D., Forshew, T., Piskorz, A. M., Parkinson, C., Chin, S. F., Kingsbury, Z., Wong, A. S. et al. (2013) Non-invasive analysis of acquired resistance to cancer therapy by sequencing of plasma DNA. Nature, 497, 108-112.
9. Tie, J., Kinde, I., Wang, Y., Wong, H. L., Roebert, J., Christie, M., Tacey, M., Wong, R., Singh, M., Karapetis, C. S. et al. (2015) Circulating tumor DNA as an early marker of therapeutic response in patients with metastatic colorectal cancer. Annals of oncology: official journal of the European Society for Medical Oncology/ESMO.
10. Hogue, M. O., Lee, J., Begum, S., Yamashita, K., Engles, J. M., Schoenberg, M., Westra, W. H. and Sidransky, D. (2003) High-throughput molecular analysis of urine sediment for the detection of bladder cancer by high-density single-nucleotide polymorphism array. Cancer research, 63, 5723-5726.
11. Thunnissen, F. B. (2003) Sputum examination for early detection of lung cancer. Journal of clinical pathology, 56, 805-810.
12. Diehl, F., Schmidt, K., Durkee, K. H., Moore, K. J., Goodman, S. N., Shuber, A P, Kinzler, K. W. and Vogelstein, B. (2008) Analysis of mutations in DNA isolated from plasma and stool of colorectal cancer patients. Gastroenterology, 135, 489-498.
13. Barrett, A. N., McDonnell, T. C., Chan, K. C. and Chitty, L. S. (2012) Digital PCR analysis of maternal plasma for noninvasive detection of sickle cell anemia. Clinical chemistry, 58, 1026-1032.
14. Taly, V., Pekin, D., Benhaim, L., Kotsopoulos, S. K., Le Cone, D., Li, X., Atochin, I., Link, D. R., Griffiths, A. D., Pallier, K. et al. (2013) Multiplex picodroplet digital PCR to detect KRAS mutations in circulating DNA from the plasma of colorectal cancer patients. Clinical chemistry, 59, 1722-1731.
15. Bettegowda, C., Sausen, M., Leary, R. J., Kinde, I., Wang, Y., Agrawal, N., Bartlett, B. R., Wang, H., Luber, B., Alani, R. M. et al. (2014) Detection of circulating tumor DNA in early- and late-stage human malignancies. Science translational medicine, 6, 224ra224.
16. Kinde, I., Wu, J., Papadopoulos, N., Kinzler, K. W. and Vogelstein, B. (2011) Detection and quantification of rare mutations with massively parallel sequencing. Proceedings of the National Academy of Sciences of the United States of America, 108, 9530-9535.
17. Andersson, D., Akrap, N., Svec, D., Godfrey, T. E., Kubista, M., Landberg, G. and Stahlberg, A. (2015) Properties of targeted preamplification in DNA and cDNA quantification. Expert review of molecular diagnostics, 15, 1085-1100.

TABLE 1

Primers for SaferSeq

| Assay | gene | 5-plex | 13-plex | 31-plex | Plasma 5-plex | chromosome | chr start | chr end | fwd primer (SEQ ID NO: 2-36) | rev primer (SEQ ID NO: 37-71) | ampl icon length | Notes |
|---|---|---|---|---|---|---|---|---|---|---|---|---|
| APC_1 | APC | | | x | | chr5 | 112177482 | 112177614 | GTCCCAGAAATATGGGTGGCATA | GCACCTTCCTGAATAGCTTTCCAA | 133 | |
| APC_2 | APC | x | x | | | chr5 | 112175555 | 112175689 | GATCTTCCAGATAGCCCTGGAC | TCCACTCTCTCTCTTTTCAGCAGTA | 135 | |
| APC_3 | APC | | | x | x | chr5 | 112175606 | 112175712 | CCTCCACCACCTCCTCAAAC | GCATTTACTGCAGCTTGCTTAGGT | 107 | |

TABLE 1-continued

Primers for SaferSeq

| Assay | gene | 5-plex | 13-plex | 31-plex | Plasma 5-plex | chromosome | chr start | chr end | fwd primer (SEQ ID NO: 2-36) | rev primer (SEQ ID NO: 37-71) | amplicon length | Notes |
|---|---|---|---|---|---|---|---|---|---|---|---|---|
| APC_4 | APC | | | x | | chr5 | 112103000 | 112103139 | CTGTTCCTATGGGTTCATTTCCAAGA | AACAATAAACTGGAGTACACAAGGCA | 140 | |
| CDH_1 | CDH11 | | | x | | chr16 | 64981730 | 64981868 | TGTTGATGAAGTCATCGACATCCA | GATATTGCCACCCTCCAGAATCC | 139 | |
| CNTN6_1 | CNTN6 | | | x | | chr3 | 1424734 | 1424870 | TCAAGGTTTGTCTACAGAAATGAAAGCA | GACAACTTACCATCTTCCCCAGA | 137 | |
| CNTNA_1 | CNTNAP5 | | | x | | chr2 | 125660512 | 125660639 | GGATGCATGTCTTCCGTCCA | GAGTCCACCATGAAGCCACA | 128 | |
| COL_1 | COL11A1 | | | x | | chr1 | 103347239 | 103347358 | AGGTAATAACATACCAGTTTTCCCCTCT | TCACCTACTCACTAACTTTTCTGTTCCT | 120 | |
| COL_2 | COL11A1 | | | x | | chr1 | 103345233 | 103345370 | ACTCACCGCACAACCATCAT | CATCAGTCAGCAGCCTGGTA | 138 | |
| CSMD_1 | CSMD3 | | | x | | chr8 | 113246583 | 113246694 | ACTATACTTACAAAGCCATCCATTGCC | GCCAGGAAGCTCGCCTAAT | 112 | |
| CSMD_2 | CSMD3 | | | x | | chr8 | 113988224 | 113988359 | CGCTGTTCCTCGGAAAGTCTAT | ACACTACCTCCACTGGTGAGT | 136 | |
| CTNN_1 | CTNNB1 | | | x | | chr3 | 41277155 | 41277287 | TTGTTCCTCAAACTTTACAGAGGAG | TGTGAACATCCCGAGCTAGGA | 133 | |
| CTNN_2 | CTNNB1 | | | x | | chr3 | 41275630 | 41275769 | GCTACTGTTGGATTGATTCGAAATCTT | CCACCCATGGACGTACGG | 140 | |
| ELTD_1 | ELTD1 | | x | x | | chr1 | 79387338 | 79387468 | AGGTGATTACAGCGGCATGA | ACAGATAGGTATAGGAGTCTATGTGCATTT | 131 | |
| KRAS_1 | KRAS | | x | | | chr12 | 25398203 | 25398329 | TTTACCTCTATTGTTGGATCATATTCGTCCA | GCCTGCTGAAAATGACTGAATATAAACTTGTG | 127 | |
| KRAS_2 | KRAS | | | x | x | chr12 | 25398252 | 25398329 | GCCTGCTGAAAATGACTGAATATAAACTTG | GCTGTATCGTCAAGGCACTCTT | 78 | |
| LRP_1 | LRP1B | | | x | | chr2 | 141356209 | 141356332 | GGATCCATCGTATTCACACCTTTCAATT | TCAAGTGGTGGTCAGTACAGACATA | 124 | |
| LRP_2 | LRP1B | | | x | | chr2 | 141526818 | 141526936 | CTGATATAGGCATCAAAGCATCCATTTG | CTTATCTCCGGCCCTGCATTTA | 119 | |
| PIK_1 | PIK3CA | x | x | x | | chr3 | 178935992 | 178936131 | TTACAGAGTAACAGACTAGCTAGAGAC | AGCACTTACCTGTGACTCCATAGA | 140 | |
| PIK_2 | PIK3CA | | x | x | | chr3 | 178952004 | 178952125 | CATACATTCGAAAGACCCTAGCCTTAG | GTGGAAGATCCAATCCATTTTGTTGT | 122 | |
| PIK_3 | PIK3CA | | x | x | | chr3 | 178916824 | 178916957 | GTAAGTGTTACTCAAGAAGCAGAAAGG | CGATTGAGGATCTTTTCTTCACGGTT | 134 | |
| PTEN_1 | PTEN | | x | x | | chr10 | 89717700 | 89717823 | AGTTCCCTCAGCCGTTACCT | TCTGTCCTTATTTTGGATATTTCTCCCAATG | 124 | |

TABLE 1-continued

Primers for SaferSeq

| Assay | gene | 5-plex | 13-plex | 31-plex | Plasma 5-plex | chromosome | chr start | chr end | fwd primer (SEQ ID NO: 2-36) | rev primer (SEQ ID NO: 37-71) | amplicon length | Notes |
|---|---|---|---|---|---|---|---|---|---|---|---|---|
| SMA_1 | SMARCA4 | x | x | x |  | chr19 | 11132395 | 11132494 | CCGCAGATCCG TTGGAAGTA | GTGCCACATAG TGCGTGTT | 100 | no GG hairpin stabilizer |
| SMA_2 | SMARCA4 |  |  | x |  | chr19 | 11132521 | 11132630 | CCGCTGCAGAA CAAGCTTC | ATGGCAAAGGG TGCGTTAAAC | 110 | 3 G's in GG hairpin stabilizer |
| SMA_3 | SMARCA4 |  |  | x |  | chr19 | 11134161 | 11134292 | AACGCTTGCTT CTCCTGTCTT | GGCCTCGACTT CCTTCTTGA | 132 |  |
| SMA_4 | SMARCA4 | x | x | x |  | chr19 | 11168903 | 11169016 | GGTGATAGCCG CCGGTTC | GCTTGCGGATG AGCTCGTA | 114 | no GG hairpin stabilizer |
| TP_1 | TP53 |  |  | x | x | chr17 | 7577047 | 7577146 | GTGGTGAGGCT CCCCTTT | ACTGGGACGGA ACAGCTTTG | 100 |  |
| TP_2 | TP53 | x | x |  |  | chr17 | 7578174 | 7578312 | GACCTCAGGCG GCTCATAG | GATTCCTCACT GATTGCTCTTA GGT | 139 |  |
| TP_3 | TP53 |  |  | x |  | chr17 | 7578412 | 7578543 | ACAACCTCCGT CATGTGCTG | CCTCAACAAGA TGTTTTGCCAA CTG | 132 |  |
| TP_4 | TP53 |  |  | x | x | chr17 | 7578173 | 7578260 | AGACCTCAGGC GGCTCATAG | GTGGAAGGAAA TTTGCGTGTGG A | 88 |  |
| TP_5 | TP53 |  |  | x |  | chr17 | 7577479 | 7577595 | GGTGGCAAGTG GCTCCTGAC | GTACCACCATC CACTACAACTA CATGTGTAA | 117 |  |
| TP_6 | TP53 | x | x |  |  | chr17 | 7577010 | 7577146 | CTTGCTTACCT CGCTTAGTGCT | ACTGGGACGGA ACAGCTTTG | 137 |  |
| TP_7 | TP53 |  |  | x | x | chr17 | 7577498 | 7577599 | CCTGGAGTCTT CCAGTGTGATG | GACTGTACCAC CATCCACTACA AC | 102 |  |
| TP_8 | TP53 |  |  | x | x | chr17 | 7579500 | 7579625 | CTTCATCTGGA CCTGGGTCTTC | CTGGTCCTCTG ACTGCTCTTT | 126 |  |
| TP_9 | TP53 |  |  | x |  | chr17 | 7579266 | 7579365 | CCAGGCATTGA AGTCTCATGGA | GGTTTCCGTCT GGGCTTCTT | 100 |  |

Universal fwd primer SEQ ID NO: 72 GGACACTCTTTCCCTACACGACGCTCTTCCGATCTNNNNNNNNNNNNATGGGAAAGAGTGTCC-fwd target primer
Universal Rev primer SEQ ID NO: 73 GTGACTGGAGTTCAGACGTGTGCTCTTCCGATCT-rev target primer
Illumina fwd primer SEQ ID NO: 74 AATGATACGGCGACCACCGAGATCTACACTCTTTCCCTACACGACGCTCTTCCGATCT
Illumina rev primer with index SEQ ID NO: 75 CAAGCAGAAGACGGCATACGAGATNNNNNNGTGACTGGAGTTCAGACGTGTGCTCTTCCGATCT
Index primer SEQ ID NO: 76 GATCGGAAGAGCACACGTCTGAACTCCAGTCAC

TABLE 2

SEQ ID NOs: 78-126
INDEX SEQUENCES

| | |
|---|---|
| 1 | ATCACG |
| 2 | CGATGT |
| 3 | TTAGGC |
| 4 | TGACCA |
| 5 | ACAGTG |
| 6 | GCCAAT |
| 7 | CAGATC |
| 8 | ACTTGA |
| 9 | GATCAG |
| 10 | TAGCTT |

TABLE 2-continued

SEQ ID NOs: 78-126
INDEX SEQUENCES

| | |
|---|---|
| 11 | GGCTAC |
| 12 | CTTGTA |
| 13 | AGTCAA |
| 14 | AGTTCC |
| 15 | ATGTCA |
| 16 | CCGTCC |
| 17 | GTAGAG |
| 18 | GTCCGC |
| 19 | GTGAAA |
| 20 | GTGGCC |
| 21 | GTTTCG |
| 22 | CGTACG |
| 23 | GAGTGG |
| 24 | GGTAGC |
| 25 | ACTGAT |
| 26 | ATGAGC |
| 27 | ATTCCT |
| 28 | CAAAAG |
| 29 | CAACTA |
| 30 | CACCGG |
| 31 | CACGAT |
| 32 | CACTCA |
| 33 | CAGGCG |
| 34 | CATGGC |
| 35 | CATTTT |
| 36 | CCAACA |
| 37 | CGGAAT |
| 38 | CTAGCT |
| 39 | CTATAC |
| 40 | CTCAGA |
| 41 | GACGAC |
| 42 | TAATCG |
| 43 | TACAGC |
| 44 | TATAAT |
| 45 | TCATTC |
| 46 | TCCCGA |
| 47 | TCGAAG |
| 48 | TCGGCA |

TABLE 3

| chr-coordinate | Gene | codon change | aa change | HotSpot | DNA source | ID in FIG. |
|---|---|---|---|---|---|---|
| chr17: 7578210 | TP53 | CGA > CGG | R -> R | Known polymorphism in dbSNP | Plasma | 1 |
| chr17: 7577120 | TP53 | CGT > CAT | R -> H | COSMIC | Spike in | * |
| chr5: 112175627 | APC | GCT > ACT | A -> T | Known polymorphism in dbSNP | Plasma | 2 |
| chr5: 112175639 | APC | CGA > TGA | R -> Stop | COSMIC | Spike in | * |
| chr5: 112175651 | APC | AAA > GAA | K -> E | COSMIC | Plasma | 3 |

Genomic location at respective chromosome using the hg19 genome.

---

We claim:

1. A method of amplifying a target nucleic acid in a sample comprising:
   a. contacting a sample comprising a target nucleic acid with a target-specific hairpin barcode forward primer and a target-specific reverse primer,
      wherein the hairpin barcode forward primer comprises, in a 5' to 3' direction: a 5' stem sequence, an adaptor sequence, a barcode sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature;

b. amplifying the target nucleic acid by performing 2-5 cycles of PCR pre-amplification on the target nucleic acid, wherein the 2-5 cycles of PCR pre-amplification have an annealing temperature less than or equal to the closed annealing temperature of the hairpin barcode forward primer, to generate a plurality of pre-amplification target nucleic acids;
c. contacting the plurality of pre-amplification target nucleic acids with an adaptor-specific forward primer and an adaptor-specific reverse primer; and
d. amplifying the pre-amplification target nucleic acid by performing at least 10 cycles of PCR amplification on the pre-amplification target nucleic acids, wherein at least 3 of the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

2. The method of claim 1, wherein the 3' stem sequence is 12-15 nucleotides.

3. The method of claim 1, wherein the 3' stem sequence and the adaptor sequence each comprise sequence complementary to each other and the complementary sequences hybridize to each other at a closed annealing temperature and do not hybridize to each other at an open annealing temperature.

4. The method of claim 3, wherein the 3' stem sequence and the adaptor sequence comprise 10-12 nucleotides of sequence completely complementary to each other.

5. The method of claim 1, wherein the hairpin barcode forward primer further comprises at least two destabilizing nucleotides 3' of the barcode sequence.

6. The method of claim 1, wherein the closed annealing temperature is equal to or less than 60° C.

7. The method of claim 1, wherein the open annealing temperature is at least 65° C.

8. The method of claim 1, wherein the barcode sequence is 6-18 nucleotides.

9. The method of claim 1, wherein the target-specific reverse primer is a hairpin barcode reverse primer, wherein the hairpin barcode reverse primer comprises, in a 5' to 3' direction: a 5' stem sequence, an adaptor sequence, a barcode sequence, a 3' stem sequence, and a 3' target-specific sequence, wherein the 5' stem sequence and the 3' stem sequence each comprise sequence complementary to each other and the complementary sequences hybridize to each other under a closed annealing temperature and do not hybridize to each other at an open annealing temperature.

10. The method of claim 1, wherein the method further comprises a step of detecting or sequencing the plurality of target nucleic acid amplicons.

11. A method of pre-amplifying a target nucleic acid in a sample prior to amplification comprising:
a. contacting a sample comprising a target nucleic acid with a target-specific hairpin barcode forward primer and a target-specific reverse primer,
wherein the hairpin barcode forward primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other, and the complementary sequences hybridize to each other under a closed annealing temperature and do not hybridize to each other at an open annealing temperature, and
wherein the sequence to be protected comprises, in the 5' to 3' direction, a barcode sequence and an adaptor sequence; and
b. pre-amplifying the target nucleic acid by performing at least one cycle of PCR pre-amplification on the target nucleic acid, wherein the at least one cycle of PCR pre-amplification has an annealing temperature less than or equal to the closed annealing temperature of the hairpin barcode forward primer, thereby generating a plurality of pre-amplification target nucleic acids.

12. A method of amplifying a target nucleic acid in a sample comprising:
a. contacting a sample comprising a target nucleic acid with a target-specific hairpin barcode forward primer and a target-specific reverse primer,
wherein the hairpin barcode forward primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other, and the complementary sequences hybridize to each other under a closed annealing temperature and do not hybridize to each other at an open annealing temperature, and
wherein the sequence to be protected comprises, in the 5' to 3' direction, a barcode sequence and an adaptor sequence;
b. pre-amplifying the target nucleic acid by performing at least one cycle of PCR pre-amplification on the target nucleic acid, wherein the at least one cycle of PCR pre-amplification has an annealing temperature less than or equal to the closed annealing temperature of the hairpin barcode forward primer, to generate a plurality of pre-amplification target nucleic acids;
c. contacting the plurality of pre-amplification target nucleic acids with an adaptor-specific forward primer and an adaptor-specific reverse primer; and
d. amplifying the pre-amplification target nucleic acid by performing at least 10 cycles of PCR amplification on the pre-amplification target nucleic acids, wherein the at least 10 cycles of PCR-based amplification have an annealing temperature greater than or equal to the open annealing temperature of the hairpin barcode forward primer, to generate a plurality of target nucleic acid amplicons, wherein the target nucleic acid amplicons comprise the adaptor sequence and the barcode sequence.

13. The method of claim 11, wherein the 3' stem sequence is 5-20 nucleotides.

14. The method of claim 11, wherein the 3' stem sequence and the adaptor sequence each comprise sequence complementary to each other, and the complementary sequences are hybridized to each other at a closed annealing temperature and do not hybridize to each other at an open annealing temperature.

15. The method of claim 14, wherein the 3' stem sequence and the adaptor sequence comprise 10-12 nucleotides of sequence completely complementary to each other.

16. The method of claim 11, wherein the hairpin barcode forward primer further comprises at least two destabilizing nucleotides 3' of the barcode sequence.

17. The method of claim 11, wherein the closed annealing temperature is equal to or less than 60° C.

18. The method of claim 11, wherein the open annealing temperature is at least 65° C.

19. The method of claim 11, wherein the barcode sequence is 6-18 nucleotides.

20. The method of claim 11, wherein the target-specific reverse primer is a hairpin barcode reverse primer, wherein the hairpin barcode reverse primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other and the complementary sequences hybridize to each other under a closed annealing temperature, and do not hybridize to each other at an open annealing temperature.

21. A method of producing a pre-amplified target nucleic acid comprising:
  a. contacting a sample comprising a target nucleic acid with a target-specific hairpin barcode forward primer and a target-specific reverse primer,
    wherein the hairpin barcode forward primer comprises, in a 5' to 3' direction: a 5' stem sequence, a sequence to be protected, a 3' stem sequence, and a 3' target-specific sequence, wherein the 5' stem sequence and the 3' stem sequence each comprise sequence complementary to each other, and the complementary sequences hybridize to each other under a closed annealing temperature and do not hybridize to each other at an open annealing temperature, and
    wherein the sequence to be protected comprises, in the 5' to 3' direction, a barcode sequence and an adaptor sequence; and
  b. pre-amplifying the target nucleic acid by performing at least one cycle of PCR pre-amplification on the target nucleic acid, wherein the at least one cycle of PCR pre-amplification has an annealing temperature less than or equal to the closed annealing temperature of the hairpin barcode forward primer, thereby generating a plurality of pre-amplification target nucleic acids.

* * * * *